United States Patent
Looby

(10) Patent No.: US 11,732,027 B2
(45) Date of Patent: *Aug. 22, 2023

(54) PROTEASE-ACTIVATED RECEPTOR-2 MODULATORS

(71) Applicant: Oasis Pharmaceuticals, LLC, Lexington, MA (US)

(72) Inventor: Richard J. Looby, Reading, MA (US)

(73) Assignee: Oasis Pharmaceuticals, LLC, Lexington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/926,304

(22) Filed: Jul. 10, 2020

(65) Prior Publication Data

US 2021/0061883 A1 Mar. 4, 2021

Related U.S. Application Data

(63) Continuation of application No. 15/349,364, filed on Nov. 11, 2016, now Pat. No. 11,091,533.

(60) Provisional application No. 62/255,334, filed on Nov. 13, 2015.

(51) Int. Cl.
*A61K 38/00* (2006.01)
*C07K 14/72* (2006.01)
*C07K 14/705* (2006.01)

(52) U.S. Cl.
CPC .......... *C07K 14/723* (2013.01); *C07K 14/705* (2013.01); *A61K 38/00* (2013.01)

(58) Field of Classification Search
CPC combination set(s) only.
See application file for complete search history.

(56) References Cited

U.S. PATENT DOCUMENTS

| | | |
|---|---|---|
| 5,716,789 A | 2/1998 | Sundelin et al. |
| 6,464,975 B2 | 10/2002 | Millis |
| 6,503,511 B1 | 1/2003 | Wizemann et al. |
| 6,562,958 B1 | 5/2003 | Breton et al. |
| 6,703,491 B1 | 3/2004 | Homburger et al. |
| 6,747,137 B1 | 6/2004 | Weinstock et al. |
| 6,773,893 B1 | 8/2004 | Tall |
| 6,815,200 B1 | 11/2004 | Krasnykh et al. |

(Continued)

FOREIGN PATENT DOCUMENTS

| | | |
|---|---|---|
| JP | 2003-530875 A | 10/2003 |
| JP | 2013-504577 A | 2/2013 |

(Continued)

OTHER PUBLICATIONS

Shanks et al., "Are animal models predictive for humans?," Philosophy, Ethics, and Humanities in Medicine 2009, 4:2 (pp. 1-20) (Year: 2009).*

(Continued)

*Primary Examiner* — Julie Ha
*Assistant Examiner* — Kristina M Hellman
(74) *Attorney, Agent, or Firm* — Wolf, Greenfield & Sacks, P.C.

(57) ABSTRACT

Provided herein are peptides comprising a mutated fragment of a wild-type protease-activated receptor-2 (PAR2). The peptides comprising a hydrophobic moiety can penetrate the cell membrane and act as an antagonist of PAR2. Also provided herein are compositions and cells comprising the peptides and methods of using the peptides.

35 Claims, 6 Drawing Sheets

Specification includes a Sequence Listing.

(56) References Cited

U.S. PATENT DOCUMENTS

| | | | |
|---|---|---|---|
| 6,864,229 | B2 | 3/2005 | Kuliopulos et al. |
| 7,189,691 | B2 | 3/2007 | Hemenway |
| 7,214,786 | B2 | 5/2007 | Kovalic et al. |
| 7,319,142 | B1 | 1/2008 | Goldman et al. |
| 7,368,531 | B2 | 5/2008 | Rosen et al. |
| 7,527,933 | B2 | 5/2009 | Sahin et al. |
| 7,696,168 | B2 | 4/2010 | Kuliopulos et al. |
| 7,718,762 | B2 | 5/2010 | Coggin, Jr. et al. |
| 7,739,055 | B2 | 6/2010 | Stephanopoulos et al. |
| 7,834,146 | B2 | 11/2010 | Kovalic et al. |
| 7,862,826 | B2 | 1/2011 | Murphy et al. |
| 7,972,993 | B2 | 7/2011 | Slootstra et al. |
| 8,067,671 | B2 * | 11/2011 | Boukharov ........ C12N 15/8285 800/285 |
| 8,071,732 | B2 | 12/2011 | Gaiger et al. |
| 8,303,962 | B2 | 11/2012 | Eckert et al. |
| 8,324,172 | B2 | 12/2012 | Kuliopulos et al. |
| 8,354,378 | B2 | 1/2013 | Kuliopulos et al. |
| 8,389,480 | B2 | 3/2013 | Kuliopulos et al. |
| 8,389,679 | B2 | 3/2013 | Eckert et al. |
| 8,440,627 | B2 | 5/2013 | Kuliopulos et al. |
| 8,501,930 | B2 | 8/2013 | Rozema et al. |
| 8,563,519 | B2 | 10/2013 | Kuliopulos et al. |
| 8,575,070 | B2 | 11/2013 | Watt et al. |
| 8,586,006 | B2 | 11/2013 | Hood et al. |
| 8,697,349 | B2 | 4/2014 | Hoshino et al. |
| 9,012,723 | B2 | 4/2015 | Guo et al. |
| 9,029,636 | B2 | 5/2015 | Wu et al. |
| 9,056,905 | B2 | 6/2015 | Olson et al. |
| 9,096,646 | B2 | 8/2015 | McMurry et al. |
| 9,266,930 | B1 | 2/2016 | Sette et al. |
| 9,464,124 | B2 | 10/2016 | Bancel et al. |
| 11,091,533 | B2 | 8/2021 | Looby |
| 2003/0148449 | A1 | 8/2003 | Kuliopulos et al. |
| 2006/0166274 | A1 | 7/2006 | Kuliopulos et al. |
| 2007/0179090 | A1 | 8/2007 | Kuliopulos et al. |
| 2008/0234183 | A1 | 9/2008 | Hallbrink et al. |
| 2009/0270322 | A1 | 10/2009 | Kuliopulos et al. |
| 2010/0137207 | A1 | 6/2010 | Kuliopulos et al. |
| 2011/0059095 | A1 | 3/2011 | MacDonald et al. |
| 2012/0028888 | A1 | 2/2012 | Janz et al. |
| 2014/0087993 | A1 | 3/2014 | Kuliopulos et al. |
| 2014/0227718 | A1 | 8/2014 | Kuliopulos et al. |

FOREIGN PATENT DOCUMENTS

| | | |
|---|---|---|
| JP | 2014-511866 A | 5/2014 |
| WO | 1998/016552 A1 | 4/1998 |
| WO | 2001/081408 A2 | 11/2001 |
| WO | 2012/139137 A2 | 10/2012 |
| WO | 2013/096862 A2 | 6/2013 |

OTHER PUBLICATIONS

Shearer et al., "Protease activated receptor 2 (PAR2)—a novel therapeutic target and nonalcoholic steatohepatitis (NASH)," Hepatology 60(4):587A AASLD abstract #803 (Oct. 2014) (Year: 2014).*
National Institute of Cancer—understanding and related topics, accessed Aug. 21, 2014 at URL: cancer.gov/cancertopics/understandingcancer, 63 pages (Year: 2014).*
Merck Manuals Lung Carcinoma accessed Mar. 12, 2017 at URL merckmanuals.com/professional/pulmonary-disorders/tumors-of-the-lungs/lung-carcinoma, 18 pages (Year: 2017).*
Merck Manual Colorectal Cancer accessed Aug. 21, 2014 at URL merckmanuals.com/home/digestive_disorders/tumors_of_the_digestive_system/colorectal_cancer.htm, 5 pages (Year: 2014).*
Merck Manual Bladder Cancer accessed Aug. 21, 2014 at URL: merckmanuals.com/home/kidney_and_urinary_tract_disorders/cancers_of_the_kidney_and_genitourinary_tract/bladder_cancer.html, 2 pages (Year: 2014).*
Thyroid cancer accessed Mar. 12, 2017 at URL www.merckmanuals.com/professional/endocrine-and-metabolic-disorders/thyroid-disorders/thyroid-cancers, 4 pages (Year: 2017).*
Renal cell carcinoma, accessed Mar. 12, 2017 at URL merckmanuals.com/professional/genitourinary-disorders/genitourinary-cancer/renal-cell-carcinoma, 6 pages (Year: 2017).*
Merck Manual Prostate Cancer accessed Aug. 21, 2014 at URL: merckmanuals.com/home/kidney_and_urinary_tract_disorders/cancers_of_the_kidney_and_genitourinary_tract/prostate_cancer.html?qt=prostate cancer&alt=sh, 8 pages (Year: 2014).*
Merck Manuals Neuroblastoma accessed Mar. 12, 2017 at URL merckmanuals.com/professional/ pediatrics/pediatric-cancers/neuroblastoma, 4 pages (Year: 2017).*
Cholangiocarcinoma accessed Mar. 12, 2017 at URL surgery.usc.edu/divisions/tumor/pancreasdiseases/web%20pages/BILIARY%20SYSTEM/cholangiocarcinoma, 2 pages (Year: 2017).*
Inflammatory disorders from Merck Manual, pp. 1-4. Accessed Aug. 30, 2020. (Year: 2020).*
Dermatitis from Merck Manual, pp. 1-4. Accessed Aug. 30, 2020. (Year: 2020).*
Inflammation from Merck Manual, pp. 1-3. Accessed Aug. 30, 2020. (Year: 2020).*
Drumm et al, Genetic Variation and Clinical Heterogeneity in Cystic Fibrosis, Annu. Rev. Pathol. Meeh. Dis., 2012, 7, pp. 267-282 (Year: 2012).*
Yampolsky et al, The Exchangeability of Amino Acids in Proteins, Genetics, 2005, 170, pp. 1459-1472 (Year: 2005).*
U.S. Appl. No. 15/349,364, filed Nov. 11, 2016, Looby.
PCT/US2016/061489, dated Apr. 3, 2017, *International Search Report and Written Opinion.
PCT/US2016/061489, dated May 24, 2018, International Preliminary Report on Patentability.
[No Author Listed], Obesity. MedlinePlus. 2013. Retreived from http://www.nlm.nih.gov/medlineplus/obesity.html. 1 page.
Baumgart et al., The diagnosis and treatment of Crohn's disease and ulcerative colitis. Dtsch Arztebl Int. Feb. 2009; 106(8): 123-33. doi: 10.3238/arztebl.2009.0123. Epub Feb. 20, 2009.
Cornier et al., The metabolic syndrome. Endocr Rev. Dec. 2008;29(7):777-822. doi: 10.1210/er.2008-0024. Epub Oct. 29, 2008.
Gonzalez, Atopic Dermatitis (Eczema). Merck Manual Professional Version. Aug. 2019. 8 pages. Accessed on Nov. 20, 2020 at merckmanual.com.
Herrine, Nonalcoholic Steatohepatitis (NASH). Merck Manual Professional Version. Access on Jul. 29, 2016 at merckmanual.com. 3 pages.
Kontzias, Rheumatoid Arthritis (RA). Merck Manual Professional Version. Accessed Oct. 24, 2017 at merckmanual.com. 26 pages.
Lee, Idiopathic Pulmonary Fibrosis. Merck Manual Professional Version. Sep. 2019. Accessed on Nov. 30, 2020 at merckmanual.com. 3 pages.
Weiner, Multiple sclerosis is an inflammatory T-cell-mediated autoimmune disease. Arch Neurol. Oct. 2004;61(10):1613-5. doi: 10.1001/archneur.61.10.1613.
Yau et al., Toward drugs for protease-activated receptor 2 (PAR2). J Med Chem. Oct. 10, 2013;56(19):7477-97. doi: 10.1021/jm400638v. Epub Jul. 30, 2013.
Deshpande et al., Epidemiology of diabetes and diabetes-related complications. Phys Ther. Nov. 2008;88(11):1254-64. doi: 10.2522/ptj.20080020. Epub Sep. 18, 2008.
Rosenberger et al., Challenges of neuropathic pain: focus on diabetic neuropathy. J Neural Transm (Vienna). Apr. 2020;127(4):589-624. doi: 10.1007/s00702-020-02145-7. Epub Feb. 8, 2020.
Shearer et al., Targeting Liver Fibrosis with a Cell-penetrating Protease-activated Receptor-2 (PAR2) Pepducin. J Biol Chem. Oct. 28, 2016;291(44):23188-23198. doi: 10.1074/jbc.M116.732743. Epub Sep. 9, 2016.
Ossovskaya et al., Protease-activated receptors: contribution to physiology and disease. Physiol Rev. Apr. 2004;84(2):579-621. doi: 10.1152/physrev.00028.2003.
Sevigny et al., Interdicting protease-activated receptor-2-driven inflammation with cellpenetrating pepducins. Proc Natl Acad Sci USA. May 17, 2011;108(20):8491-6. doi: 10.1073/pnas. 1017091108. Epub May 2, 2011. Supporting Information, 6 pages.

(56) References Cited

OTHER PUBLICATIONS

Shearer et al., Targeting Liver Fibrosis with a Cell-penetrating Protease-activated Receptor-2 (PAR2) Pepducin. J Biol Chem. Oct. 28, 2016;291(44):23188-23198. doi: 10.1074/jbc.M116.732743. Epub Sep. 9, 2016.
Tellez et al., Role and regulation of the thrombin receptor (PAR-1) in human melanoma. Oncogene. May 19, 2003;22(20):3130-7. doi: 10.1038/sj.onc.1206453.
Yang et al., Blockade of PAR1 signaling with cell-penetrating pepducins inhibits Akt survival pathways in breast cancer cells and suppresses tumor survival and metastasis. Cancer Res. Aug. 1, 2009;69(15):6223-31. doi: 10.1158/0008-5472.CAN-09-0187. Epub Jul. 21, 2009.
International Search Report and Written Opinion, dated Apr. 3, 2017, in connection with PCT/US2016/061489.
International Preliminary Report on Patentability, dated May 24, 2018, in connection with PCT/US2016/061489.
Antoniak et al., Protease-activated receptor 2 deficiency reduces cardiac ischemia/reperfusion injury. Arterioscler Thromb Vasc Biol. Nov. 2010;30(ll):2136-42. doi: 10.1161/ATVBAHA.110.213280. Epub Aug. 19, 2010.
Antoniak et al., Protease-activated receptor 2 deficiency reduces cardiac ischemia/reperfusion injury. Arterioscler Thromb Vasc Biol. Nov. 2010;30(11):2136-42. doi: 10.1161/ATVBAHA.110.213280. Epub Aug. 19, 2010.
Badeanlou et al., Tissue factor-protease-activated receptor 2 signaling promotes diet-induced obesity and adipose inflammation. Nat Med 2011; 17: 1490-7.
Briot et al., Kallikrein 5 induces atopic dermatitis-like lesions through PAR2-mediated thymic stromal lymphopoietin expression in Netherton syndrome. J Exp Med 2009;206:1135-47.
Buddenkotte et al., Agonists of proteinase-activated receptor-2 stimulate upregulation of intercellular cell adhesion molecule-1 in primary human keratinocytes via activation of NF-kappa B. (2005) J Invest Dermatol 124: 38-45).
Cederqvist et al., High expression of pulmonary proteinase-activated receptor 2 in acute and chronic lung injury in preterm infants. (2005) Pediatr Res 57: 831-6.
Cenac et al., Induction of intestinal inflammation in mouse by activation of proteinaseactivated receptor-2. Am J Pathol. Nov. 2002;161(5):1903-15.
Covic et al., Activation and inhibition of G protein-coupled receptors by cell-penetrating membrane-tethered peptides. Proc Natl Acad Sci USA. Jan. 22, 2002;99(2):643-8.
Covic et al., Pepducin-based intervention of thrombin-receptor signaling and systemic platelet activation. Nat. Med. 2002;8:1161-1165.
Duchatelet et al., Genetics of Atopic Dermatitis: Beyond Filaggrin-the Role of Thymic Stromal Lymphopoietin in Disease Persistence. JAMA Dermatol 2014; 150: 248-50.
Ferrell et al., Essential role for proteinase-activated receptor-2 in arthritis. J Clin Invest. Jan. 2003;111(1):35-41.
Foord et al., International Union of Pharmacology. XLVI. G protein-coupled receptor list. Pharmacol Rev. Jun. 2005;57(2):279-88.
Frateschi et al., PAR2 absence completely rescues inflammation and ichthyosis caused by altered CAP1/Prss8 expression in mouse skin. Nat Commun. 2011;2:161.
Genbank Access No. CBW25083.1. Crossman et al. Mar. 21, 2015.
Genbank Accession No. NM003950.3. Lee et al. Sep. 11, 2017.
Genbank Accession No. NM004101. Tillery et al. Oct. 3, 2017.
Grandaliano et al., Protease-activated receptor-2 expression in IgA nephropathy: a potential role in the pathogenesis of interstitial fibrosis. J Am Soc Nephrol. 2003;14:2072-83.
Hopkins et al., The druggable genome. Nat Rev Drug Discov. Sep. 2002;1(9):727-30. doi: 10.1038/nrd892.
Ikeda et al., Expression of proteinase-activated receptor-2 in human pancreatic cancer: a possible relation to cancer invasion and induction of fibrosis. Int J Oncol 2003;22:295-300.
Jacoby et al., The 7 TM G-protein-coupled receptor target family. ChemMedChem. Aug. 2006;1(8):761-82.
Kaneider et al., 'Role reversal' for the receptor PAR1 in sepsis-induced vascular damage. Nat Immunol. Dec. 2007;8(12):1303-12. Epub Oct. 28, 2007.
Kaneider et al., Reversing systemic inflammatory response syndrome with chemokine receptor pepducins. Nat Med. Jun. 2005;11(6):661-5. Epub May 8, 2005.
Kheir et al., Radicals Formed in N-Acetyl-Proline by Electron Attachment: ESR Spectroscopy and Computational Studies. J Phys Chem B. Dec. 1, 20115; 115(49): 14846-14851. EPub Nov. 21, 2011. doi: 10.1021/jp207841m.
Knight et al., Protease-activated receptor 2 promotes experimental liver fibrosis in mice and activates human hepatic stellate cells. Hepatology 2012;55:879-87.
Kwapiszewska et al., PAR-2 inhibition reverses experimental pulmonary hypertension. Circ Res 2012;110:1179-91.
Lam et al., Serine proteases and protease-activated receptor 2-dependent allodynia: a novel cancer pain pathway. Pain. May 2010;149(2):263-72. doi: 10.1016/j.pain.2010.02.010. Epub Mar. 1, 2010.
Lee et al., Protease and protease-activated receptor-2 signaling in the pathogenesis of atopic dermatitis. (2010) Yonsei Med J 51: 808-22.
Michael et al., Phaunacological inhibition of PAR2 with the pepducin P2pal-18S protects mice against acute experimental biliary pancreatitis. Am J Physiol Gastrointest Liver Physiol 2013;304: G516-26.
Noorbakhsh et al., Proteinase-activated receptor 2 modulates neuroinflammation in experimental autoimmune encephalomyelitis and multiple sclerosis. J Exp Med. Feb. 20, 2006;203(2):425-35. Epub Feb. 13, 2006.
Park et al., Clinical implication of protease-activated receptor-2 in idiopathic pulmonary fibrosis. Respir Med 2012; 107: 256-6.
Pierce et al., Seven-transmembrane receptors. Nat Rev Mol Cell Biol. Sep. 2002;3(9):639-50.
Rattenholl et al., Proteinase-activated receptor-2 in the skin: receptor expression, activation and function during health and disease. Drug News Perspect 2008;21: 369-81.
Schmidlin et al., Protease-activated receptor 2 mediates eosinophil infiltration and hyperreactivity in allergic inflammation of the airway. J Immunol. Nov. 1, 2002;169(9):5315-21.
Seeliger et al., Proinflammatory role of proteinase-activated receptor-2 in humans and mice during cutaneous inflammation in vivo. FASEB J. 2003;17:1871-85.
Sevigny et al., Interdicting protease-activated receptor-2-driven inflammation with cellpenetrating pepducins. Proc Natl Acad Sci U S A. May 17, 2011;108(20):8491-6. doi: 10.1073/pnas.1017091108. Epub May 2, 2011.
Shi et al., Protease-activated receptors (PAR1 and PAR2) contribute to tumor cell motility and metastasis. Mol Cancer Res. Jul. 2004;2(7):395-402.
Steinhoff et al., Proteinaseactivated receptor-2 in human skin: tissue distribution and activation of keratinocytes by mast cell tryptase. (1999) Exp Dermatol 8: 282-94.
Vergnolle et al., Characterization of the inflammatory response to proteinase-activated receptor-2 (PAR2)-activating peptides in the rat paw. Br J Pharmacol. Jul. 1999; 127(5):1083-90.
Vergnolle et al., Proteinase-activated receptor-2 and hyperalgesia: A novel pain pathway. Nat Med. Jul. 2001;7(7):821-6.
Wilson et al., The epithelial cell-derived atopic dermatitis cytokine TSLP activates neurons to induce itch. Cell 2013;155:285-95.
Wygrecka et al., Mast cells and fibroblasts work in concert to aggravate pulmonary fibrosis: role of transmembrane SCF and the PAR-2/PKC-alpha/Raf-1/p44/42 signaling pathway. Am J Pathol 2013;182:2094-108.

\* cited by examiner

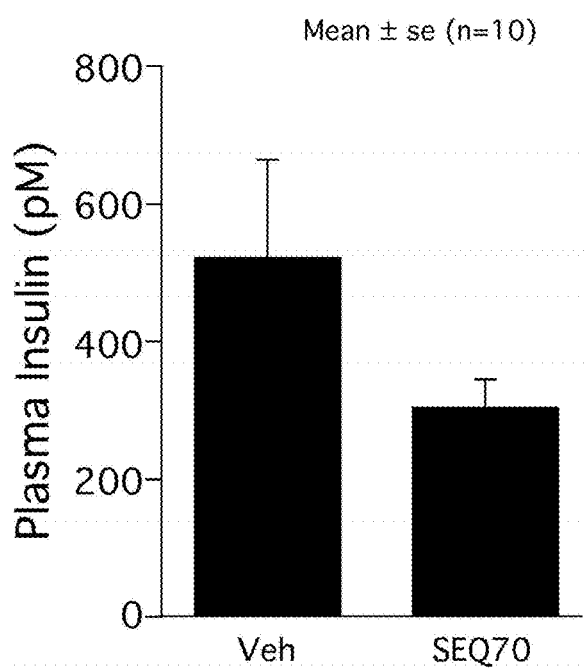 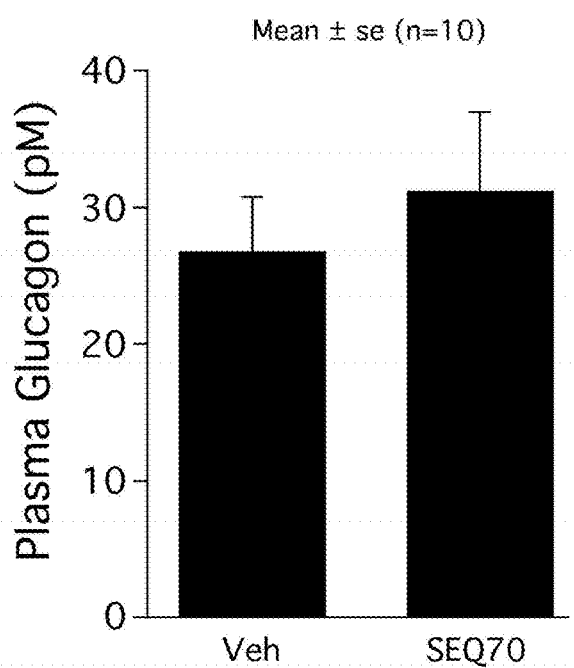
Figure 4A                    Figure 4B

PROTEASE-ACTIVATED RECEPTOR-2 MODULATORS

RELATED APPLICATIONS

This application is a divisional of and claims priority under 35 U.S.C. § 120 to U.S. patent application, U.S. Ser. No. 15/349,364, filed Nov. 11, 2016, which claims priority under 35 U.S.C. § 119(e) to U.S. Provisional Application, U.S. Ser. No. 62/255,334, filed Nov. 13, 2015, each of which is incorporated herein by reference.

GOVERNMENT SUPPORT

This invention was made with government support under grant number R42DK101240 awarded by the National Institutes of Health-National Institute of Diabetes and Digestive and Kidney Diseases. The government has certain rights in the invention.

BACKGROUND

A variety of hormones, neurotransmitters and biologically active substances control, regulate, or adjust the functions of organisms via specific receptors located in cell membranes. In eukaryotes including yeasts and mammals, many of these receptors mediate the transmission of intracellular signals by activating guanine nucleotide-binding proteins (G proteins), to which the receptor is coupled. Such receptors are generically referred to as G protein-coupled receptors (GPCRs), also known as G protein-linked receptors (GPLR) or seven-transmembrane domain receptors. Binding of a specific signaling molecule, i.e., a ligand, to the GPCR can cause a conformational change in the receptor, resulting in a form that is able to bind and activate a G protein, thereby triggering a cascade of intracellular events that eventually leads to a biological response. Typically, GPCRs interact with G proteins to regulate the synthesis of intracellular second messengers, such as cyclic AMP, inositol phosphates, diacylglycerol, and calcium ions.

Known and uncharacterized GPCRs have been major targets for drug action and development as they are implicated in many diseases (Jacoby et al., *Chem. Med. Chem.* 2006, 1:760-782). GPCRs usually share a common structural motif of seven transmembrane helical domains (TM1 to TM7) connected by three intracellular (IL-1/i1 to IL-3/i3) loops and three extracellular (EL-1/e1 to EL-3/e3) loops. The seven transmembrane helices form a barrel-like cavity within the plasma membrane, and it is the conformational change in this structure triggered by extracellular interaction with a ligand that further activates domains for G-protein coupling inside the cell. GPCRs play a vital role in the signaling processes that control cellular metabolism, fibrosis, tissue remodeling, cell growth and motility, adhesion, inflammation, neuronal signaling, and blood coagulation.

GPCRs, along with G-proteins and effectors (intracellular enzymes and proteins, and channels modulated by G-proteins), are the components of a modular signaling system that connects the state of intra-cellular second messengers to extra-cellular inputs (Pierce et al., *Nature Rev Mole Cell Bio* 2002, 3, 639-650). The superfamily of GPCRs is large, and sequencing of the human genome has revealed over 850 genes that encode them (Hopkins and Groom *Nature Reviews Drug Discovery* 2002, 1, 727-730). GPCRs can be divided into six classes based on sequence homology and functional similarity (Foord et al., *Pharmacol Rev* 2005, 57(2): 279-88): Class A (or 1) (Rhodopsin-like), Class B (or 2) (Secretin receptor family), Class C (or 3) (Metabotropic glutamate/pheromone), Class D (or 4) (Fungal mating pheromone receptors), Class E (or 5) (Cyclic AMP receptors), and Class F (or 6) (Frizzled/Smoothened).

Among Rhodopsin-like GPCRs (class A or 1) are protease-activated receptors (PARs), which are a subfamily of seven-transmembrane GPCRs and are activated through cleavage of part of their extracellular domains and act as sensors of extracellular protease gradients, allowing cells to react to the proteolytic microenvironment during tissue remodeling in fibrosis, cancer, coagulation, and a myriad of other processes such as those involved in acute and chronic inflammation. Members of the PAR family act as sensors of extracellular protease gradients, enabling cells to react to the proteolytic microenvironment during a wide range of physiological activities such as tissue remodeling. To date, four different PARs have been identified: PAR1, PAR2, PAR3 and PAR4. They are expressed throughout the human body. Proteases such as trypsin, thrombin, Xa, VIIa, matriptase, hepsin, tryptase and MMP-1 cleave the N-terminal extracellular domain of individual PAR members, thereby unmasking a tethered ligand that binds to the outer surface of the receptor to activate transmembrane signaling to intracellular G proteins. PAR1 was originally discovered on platelets and serves as the prototype for this specialized class of GPCRs. PAR1 is activated when it is cleaved by thrombin between residues R41-S42 located within the N-terminal extracellular domain of the receptor. PAR3 and PAR4 are also activated by thrombin, whereas PAR2 is best known as a trypsin/tryptase/Xa/VIIa receptor. Proteolytic cleavage exposes a new N-terminus that binds to the body of the receptor in an unusual intra-molecular mode. Synthetic peptides that correspond to the first few amino acids of the freshly cleaved N-terminus of the PARs (e.g., SFLLRN$^{PAR1}$ (SEQ ID NO: 80), TFLLRN$^{PAR1}$ (SEQ ID NO: 71), PRSFLLRN$^{PAR1}$ (SEQ ID NO: 72), SLIGRL$^{PAR2}$ (SEQ ID NO: 73), AYPGKF$^{PAR4}$ (SEQ ID NO: 74) can also function as selective soluble inter-molecular agonists to PARs.

PAR1, the major thrombin receptor, has been shown to influence a wide range of physiological and pathological processes of the cardiovascular system, including endothelial barrier function, vasoreactivity, intimal hyperplasia, inflammation, and hemostasis (Ossovskaya et al., *Physiol Rev* 2004, 84:579-621). PAR1 is a mediator of proliferation and migration of endothelial cells in vitro and is essential for angiogenesis in the developing mouse. PAR1-deficient mice result in lethality of half the embryos at midgestation (E9.5) due to defective blood vessel formation. Surprisingly, PAR1-deficient mice do not have altered platelet function phenotypes leading to the discovery of PAR4. Unlike in humans, PAR4 is the major thrombin receptor on mouse platelets, and PAR4-deficient mice do not signal to thrombin. PAR2, a cell surface receptor for trypsin-like proteases, is widely expressed in inflammatory cells, mesenchymal cells (e.g. fibroblasts, myofibroblasts, smooth muscle cells), stromal cells, endothelium, hepatocytes, stellate cells, keratinocytes, pancreatic cells, nerve cells, cardiac cells, and epithelia including lung, intestinal, and hepatobiliary. PAR2 plays a key role in a number of acute and chronic inflammatory diseases of the skin, joints, lungs, brain, gastrointestinal tract and liver, and vascular systems, and has been implicated in the progression of liver, lung, kidney and other fibrotic diseases, atopic dermatitis, chronic and acute pain conditions, itch, and pulmonary arterial hypertension. The functional role of PAR3 is unclear and the synthetic PAR3 tethered ligand TFRGAP (SEQ ID NO: 75) does not stimulate detectable downstream signaling. PARs have also been shown to form functional homodimers/oligomers, and heterodimers/oligomers. PAR1 and PAR3 can serve as cofactors for PAR4, and PAR1 can transactivate PAR2 (Kaneider et al., *Nat. Immunol.* 2007, 8:1303-12).

Each PAR couples to a distinct subset of G proteins. For instance, PAR1 couples with Gα-subunits $G_q$, $G_i$ and $G_{12/13}$ that are differentially activated by different proteases. Thrombin can concomitantly activate all three heterotrimeric subunits whereas MMP-1 more selectively activates $G_{12/13}$ signaling. PAR1-$G_q$ stimulates phospholipase C-β generatation of InsP$_3$, which mobilizes $Ca^{2+}$, and diacylglycerol (DAG), which activates protein kinase C-α (PKCα). These in turn activate phospholipase A$_2$ and phospholipase D. $G_{12/13}$ plays a major role in cell shape change, migration, and rho-dependent oncogenesis. PAR2 can stimulate Gq, Gi and beta-arrestin signaling. Previously it has been shown that a switch in G-protein signaling from $G_{12/13}$ to $G_i$ occurs in the context of PAR1-PAR2 heterodimers is involved in the maintenance of endothelial barrier function. $G_i$ is involved in activation of rac, PI3K, and inhibition of adenylate cyclase and suppression of cAMP. It is still not well understood how PAR1 and PAR2 regulates the MAP kinase cascade members, such as ERK1/2.

SUMMARY OF THE INVENTION

Cell-penetrating peptides called PEPDUCINS™ have been devised by attaching a membrane-penetrating, hydrophobic moiety to peptides derived from a wild-type GPCR, thereby producing man-made agonists and/or antagonists against specific receptor-G protein signaling pathways (Covic L. et al. 2002, *PNAS* 99: 643-48; U.S. Pat. Nos. 6,864,229; 7,696,168; 8,389,480, each of which are incorporated herein by reference). These lipidated peptides or polypeptides ("lipopeptides") have the ability to rapidly flip or cross across the membrane and interfere with receptor-G protein signaling in a highly specific manner, i.e., with high selectivity for their cognate receptors by an allosteric mechanism. Lipopeptides for PARs, e.g., PAR1, PAR2, and PAR4, cholecystokinins A and B (CCKA, CCKB), somatostatin-2 (SSTR2), melanocortin-4 (MC4R), glucagon-like peptide-1 receptor (GLP-1R), and P2Y$_{12}$ ADP receptor have been made that act as agonists and/or antagonists for the receptors from which they are derived. These compositions are useful for activating or inhibiting the activity of a broad range of GPCRs, including protein family PARs. Human PARs include PAR1 (Genbank Accession Number AF019616), PAR2 (Genbank Accession Number XM003671), PAR5 (Genbank Accession Number NM004101), and PAR4 (Genbank Accession Number NM003950.1), which are incorporated herein by reference.

While PEPDUCINs™ have been used as effective antagonists without significant or substantial agonist effect for members of the PAR family, there remains a need for more effective PAR2 antagonists both for further studying the mechanism of receptor-G protein coupling and its implications on the selective contacts between receptors and G proteins, and to make therapeutic agents for the treatment and/or prevention for various diseases and conditions where GPCRs are implicated. Candidate pepducins are constructed by attaching a hydrophobic second domain to a first domain which includes more or less the GPCR segment most likely responsible for either an interface contact such as an i3 loop, and its neighboring regions including TM6 and TM5, and/or potentially replacing/inserting into an analogous loop/TM segment in the receptor to thereby modulate receptor-G protein signaling.

The present disclosure provides new peptides based on modification of full-length PAR2 or fragments thereof. In certain embodiments, the peptides are chimeric polypeptides. The new peptides are useful for targeting the signaling events regulated by PAR2s as well as the treatment and/or prevention of PAR2-associated diseases and conditions. For example, the peptides and compositions herein are used to treat diseases or conditions associated with increased or aberrant PAR2 activity or signaling or associated with increased or aberrant PAR2 protease activity. The peptides and compositions herein can also be used to treat constitutive PAR2 activity.

In one aspect, provided are peptides and compositions thereof with substantial antagonistic effect and no substantial agonistic effect against PAR2. In certain embodiments, the peptides comprise one or more point mutations in a region of the peptide corresponding to amino acid positions 270-290 of the human PAR2 sequence. The point mutation may be one of substitution, addition, or deletion, where the addition or deletion comprises adding or deleting up to eight consecutive residues at the point of mutation in the wild type sequence. The wild-type human PAR2 sequence is provided below as SEQ ID NO: 69. As used herein, the phrase "wild-type human PAR2" refers to the human PAR2 sequence of SEQ ID NO: 69

```
                                                           (SEQ ID NO: 69)
  1 MRSPSAAWLL GAAILLAASL SCSGTIQGTN RSSKGRSLIG KVDGTSHVTG KGVTVETVFS

61 VDEFSASVLT GKLTTVFLPI VYTIVFVVGL PSNGMALWVF LFRTKKKHPA VIYMANLALA

121 DLLSVIWFPL KIAYHIHGNN WIYGEALCNV LIGFFYGNMY CSILFMTCLS VQRYWVIVNP

181 MGHSRKKANI AIGISLAIWL LILLVTIPLY VVKQTIFIPA LNITTCHDVL PEQLLVGDMF

241 NYFLSLAIGV FLFPAFLTAS AYVLMIRMLR SSAMDENSEK KRKRAIKLIV TVLAMYLICF

301 TPSNLLLVVH YFLIKSQGQS HVYALYIVAL CLSTLNSCID PFVYYFVSHD FRDHAKNALL

361 CRSVRTVKQM QVSLTSKKHS RKSSSYSSSS TTVKTSY.
```

In another aspect, the peptides are lipopeptides comprising a hydrophobic moiety (e.g., a lipid moiety, acyl moiety, steroid moiety, or an amino acid moiety) that enables the peptide's passage across a cell membrane.

In certain embodiments, the peptides comprise a sequence of: $X_4X_5X_6X_7X_8SEX_{11}X_{12}X_{13}X_{14}X_{15}X_{16}X_{17}KX_{19}$ (SEQ ID NO: 43), wherein the $X_4$ to $X_{19}$ variables are as defined herein and correspond to amino acid residues 273 to 288 of the wild-type human PAR2 sequence. Table 1, provided herein, lists exemplary peptide sequences. In certain embodiments, the peptide comprises an amino acid sequence selected from SEQ ID NO: 1-41. In certain embodiments, the peptide comprises a sequence that is about 50% to about 99% homologous to the amino acid sequence of SEQ ID NO: 1-41. In certain embodiments, the peptide comprises a sequence that is about 50% to about 99% identical to the amino acid sequence of SEQ ID NO: 1-41.

In certain embodiments, the peptide comprises a sequence that is about 50% to about 99% homologous to the amino acid sequence of SEQ ID NO: 43. In certain embodiments, the peptide comprises a sequence that is about 50% to about 99% identical to the amino acid sequence of SEQ ID NO: 43.

In certain embodiments, the peptide comprises a sequence of SEQ ID NO: 41, wherein the amino acid sequence comprises a mutation at positions $X_5$ and $X_{15}$; and wherein the peptide is at least 15 amino acids in length.

In certain embodiments, the peptide comprises a sequence of SEQ ID NO: 41, wherein the amino acid sequence comprises a mutation at positions $X_5$ and $X_{15}$, and additional amino acids at $X_{19}$ and $X_{20}$, wherein $X_{20}$ is a hydrophobic amino acid or a D-amino acid.

In certain embodiments, the peptide comprises a sequence of SEQ ID NO: 41, wherein the amino acid sequence comprises a mutation at positions $X_5$ and $X_{15}$, and additional amino acids at $X_{19}$ and $X_{20}$, wherein $X_{14}$ and $X_{20}$ are D-amino acids.

In another aspect, the peptides comprise a mutated fragment of a wild-type PAR2, wherein the peptide shares, in sequence, at least two sections of at least two contiguous amino acid residues with the wild-type PAR2 sequence. In certain embodiments, the at least two contiguous amino acid residues are found in positions of the peptide that correspond to amino acid positions 270-290 of a human PAR2 sequence, wherein at least one mutation in said mutated fragment of PAR2 is at the amino acid position corresponding to position 272, 273, 274, 275, 276, 277, 280, 282, 283, 284, 285, 286, 288, and/or 289 of the human PAR2 sequence. Additional sections of at least two contiguous amino acids are also contemplated. For example, the peptide can have 3 sections of at least 2 contiguous amino acids; a section of at least 2 and at least 3 contiguous amino acids; 2 sections of at least 3 contiguous amino acids; 3 sections of at least 3 contiguous amino acids; 2 sections of at least 3 contiguous amino acids and a section of at least 2 contiguous amino acids; a section of at least 3 contiguous amino acids and a section of at least 4 contiguous amino acids; a section of at least 3 contiguous amino acids, a section of at least 4 contiguous amino acids, and a section of at least 2 contiguous amino acids; 2 sections of at least 4 contiguous amino acids; a section of at least 4 contiguous amino acids, a section of at least 6 contiguous amino acids. The sections of contiguous amino acids are separated by at least 1, 2, 3, 4, 5, 6, 7, 8, 9, or 10 amino acid residues.

In certain embodiments, the peptide comprises a mutated fragment of a wild-type protease-activated receptor-2 (PAR2), wherein the peptide shares, in sequence, at least three contiguous amino acid residues with amino acid positions 270-290 of a human PAR2 sequence, wherein at least one mutation in said mutated fragment of PAR2 is at the amino acid position corresponding to position 272, 273, 274, 275, 276, 277, 280, 282, 283, 284, 285, 286, 288, and/or 289 of the human PAR2 sequence.

In another aspect, pharmaceutical compositions are provided comprising the peptides described herein and a pharmaceutically acceptable excipient. In certain embodiments, the pharmaceutical composition is suitable for oral, aerosol, nasal, topical, rectal, vaginal or parenteral administration, or intravenous, subcutaneous, intradermal, or intramuscular injection.

In yet another aspect, methods of treating various conditions or disorders are provided using the peptides and compositions described herein. In certain embodiment, a therapeutically effective amount of the peptide or composition thereof is administered to a subject in need thereof to treat and/or prevent a disorder or condition as described herein. For example, the peptides and compositions herein are used to treat diseases or conditions associated with increased or aberrant PAR2 activity or signaling or associated with increased or aberrant PAR2 protease activity. The peptides and compositions herein can also be used to treat constitutive PAR2 activity. Exemplary disorders or conditions include non-alcoholic steatohepatitis (NASH), idiopathic pulmonary fibrosis (IPF), atopic dermatitis (AD, eczema), kidney fibrosis, alcoholic steatohepatitis, organ fibrosis, kidney fibrosis, bone marrow fibrosis, pulmonary arterial hypertension (PAH), lung fibrosis, pruritis (itch), pancreatitis, chronic kidney disease, nephritis, multiple sclerosis, cancer, leukemia, melanoma, inflammatory disorders and conditions, sepsis, inflammation-related CNS disorders, bronchitis, asthma, diabetes, complications of diabetes and NASH, obesity, metabolic syndrome, fibrotic diseases, cardiac fibrosis, pulmonary fibrosis, inflammatory bowel disease, Crohn's disease, irritable bowel syndrome, cirrhosis, arthritis, arthrofibrosis, keloids, myelofibrosis, systemic fibrosis, scleroderma, psorasis, hives, impetigo, rashes, and rosacea.

The peptides can be combined with other pharmaceutical agents (e.g., peptides, small molecules) for use in treating various conditions or disorders.

In certain embodiments, the peptides described herein can be used in combination with glucagon-like peptide (GLP)-1 receptor agonists. Such a combination is useful, for example, for treating NASH, diabetes, complications of diabetes and NASH, and other metabolic disorders or are useful as an anti-inflammatory to suppress side effects of pancreatitis or inflammation. Non-limiting examples of GLP-1 receptor agonist include liraglutide (VICTOZA®), lixisenatide, and exenatide. In certain embodiments, the peptides described herein can be used in combination with liraglutide, lixisenatide, or exenatide.

In certain embodiments, the peptides described herein can be used in combination with pirfenidone or nintedanib. Such combinations are useful, for example, for treating idiopathic pulmonary fibrosis (IPF) or other fibrotic disorders.

In a further aspect, provided herein are kits comprising a peptide or composition as described herein.

The details of one or more embodiments of the invention are set forth in the accompanying description below. Other features, objects, and advantages of the invention will be apparent from the description. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification, including definitions, will control. In addition, the materials, methods, and examples are illustrative only and not intended to be limiting. All patents and publications cited in this specification are incorporated herein by reference to the extent permitted by applicable law.

BRIEF DESCRIPTION OF THE FIGURES

As shown in FIG. 2, there was a gradual increase in mean baseline (morning) glucose levels in the vehicle control group (19 mmol/L increased to 26 mmol/L). In the PZ-235 treatment cohort there was a relative reduction in morning blood glucose levels, consistent with the salutary effects on HbA1c observed in FIGS. 1A and 1B.

As shown in FIG. 3, there was a consistent lowering of mean blood glucose by 2 mmol/L during the first 6 h in the PZ-235 treated animals as compared to controls.

FIGS. 4A to 4B. Insulin resistance is the key etiologic defect that defines metabolic syndrome in the context of Type 2 Diabetes Mellitus (T2DM). Obesity-induced insulin resistance is the dominant factor underlying both metabolic syndrome and T2DM. Obese-diabetic db/db mice quickly become severely insulin resistant as reflected by large increases in plasma insulin with concomitant increases in glucose. Plasma from whole blood was collected from the diabetic mice at the termination of the 3 week experiment. As shown in FIGS. 4A and 4B, there was striking 45% drop in mean plasma insulin (FIG. 4A) and a 22% increase in glucagon levels (FIG. 4B) in the PZ-235 treated animals as compared to the control group. This unexpected result is the first demonstration that a PAR2 inhibitor, as exemplified by PZ-235, improves insulin levels in diabetic animals and similar PAR2 pepducins may provide salutary effects in improving insulin resistance in diabetic humans.

As shown in FIGS. 5A and 5B, there was a highly significant (P<0.01) lowering of mean plasma triglycerides (TG) by 0.7 mmol/L in the PZ-235 treated animals as compared to control animals.

As shown in FIG. 6, there was a significant (P<0.05) 15% lowering of liver triglycerides after 3 weeks of treatment of the diabetic mice with PZ-235 as compared to control animals.

DEFINITIONS

Figure 1A:
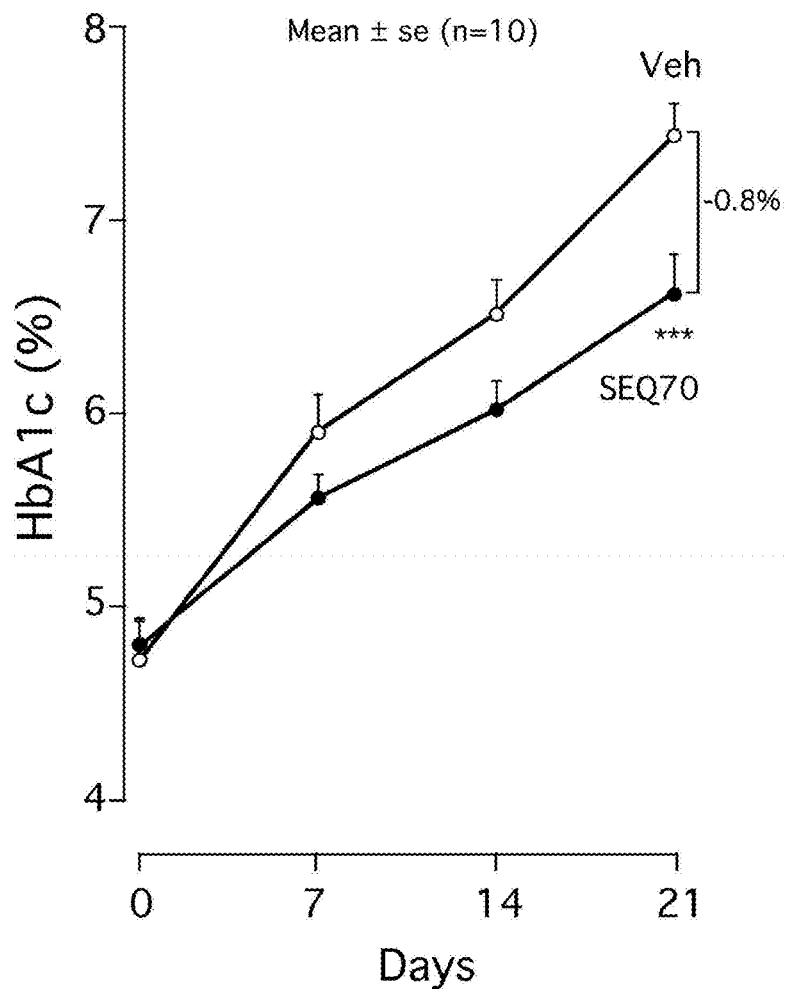
FIGS. 1A to 1B. Male obese-diabetic (db/db) mice, 6-8 weeks of age were purchase from Charles River Labs. The db/db mouse is a leptin-deficient animal which serves as a model for diabetes, obesity and dyslipidemia. Animals were randomized according to blood glucose and body weight on day −2 and were allowed to eat a normal chow diet ad libitum. Treatment was initiated from day 0 with mice receiving daily subcutaneous (SC) injections (5 mL/kg) at 7-10 AM. HbA1c was monitored on days 0, 7, 14 and 21. Mice (n=10) were treated daily with either 10 mg/kg N-palmitoylated-SEQ70 (PZ-235) or vehicle ("Veh"). Food intake (8±2 g/day/mouse) and weight gain (40±1 g at day 0 increased to 47±1 g at day 21) did not vary significantly between treatment groups over the 3 week period. Quite unexpectedly, diabetic mice treated with PZ-235 had a highly significant (P<0.001) 0.8% drop in mean glycosylated hemoglobin (HbA1c) levels as compared to the vehicle-group at the 3 week endpoint. The vehicle group animals had a mean increase in HbA1c from 4.7% to 7.4% in the vehicle-treated mice over the 3 week period, whereas the PZ-235 treated animals HbA1c levels increased from 4.8% to only 6.6%. HbA1c levels reflect long-term blood glucose levels. This unexpected result with PZ-235 would indicate that inhibition of PAR2 with a i3-loop derived pepducin may have a significant effect on reducing average glucose levels in the setting of severe diabetes in a relatively short period of time (e.g. 3 weeks of treatment).
Figure 1B:
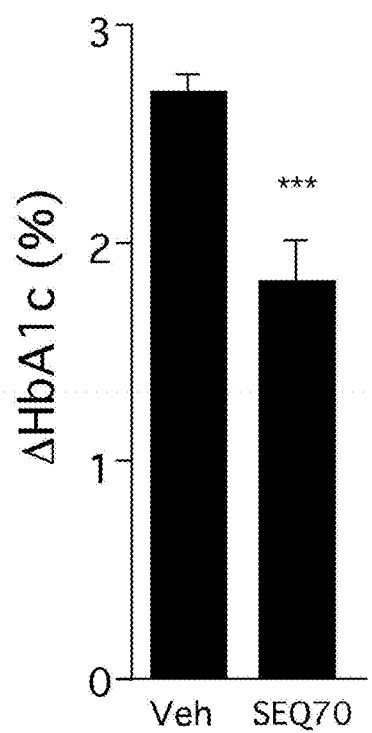
Figure 2:
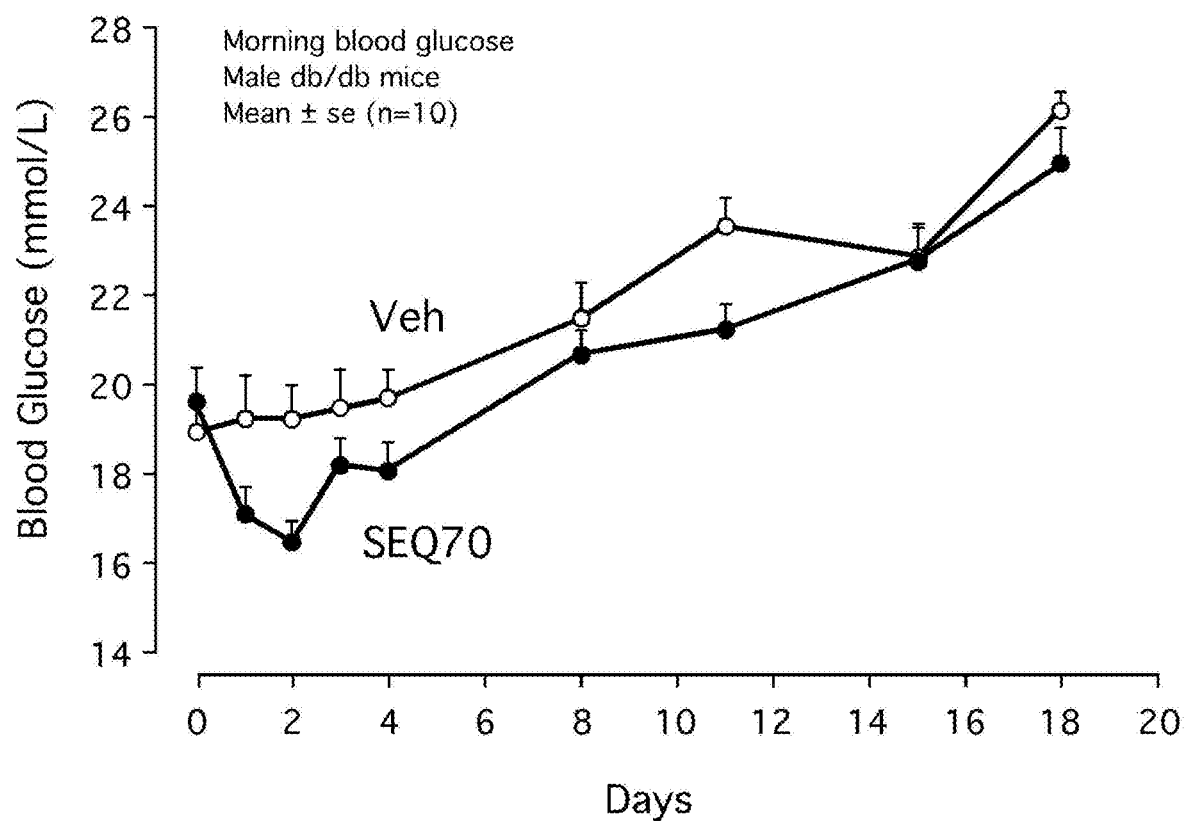
FIG. 2. Diabetic mice from the experiment in FIGS. 1A and 1B had their morning blood glucose measured thrice weekly.
Figure 3:
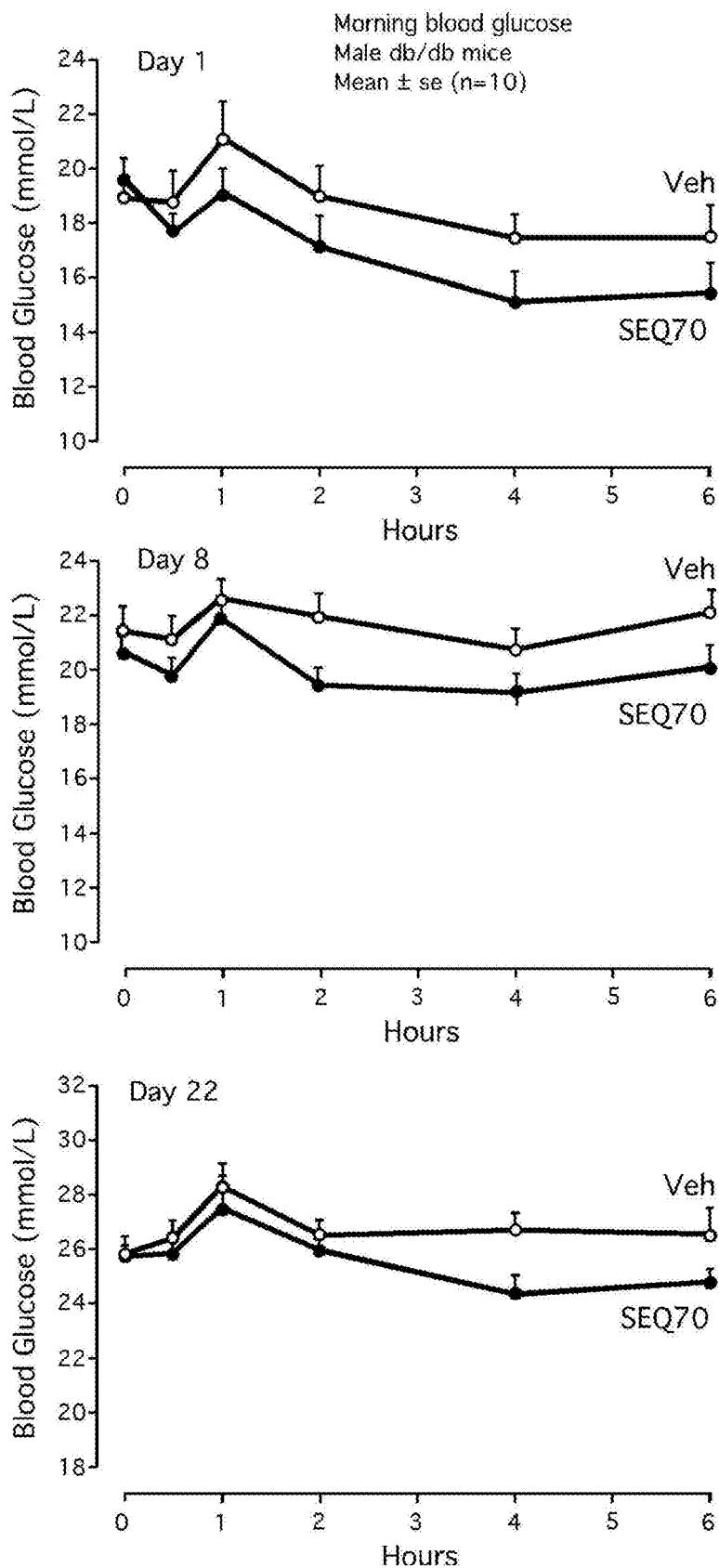
FIG. 3. Diabetic mice had their blood glucose profile monitored on days 1, 8 and 22.
Figure 5A:
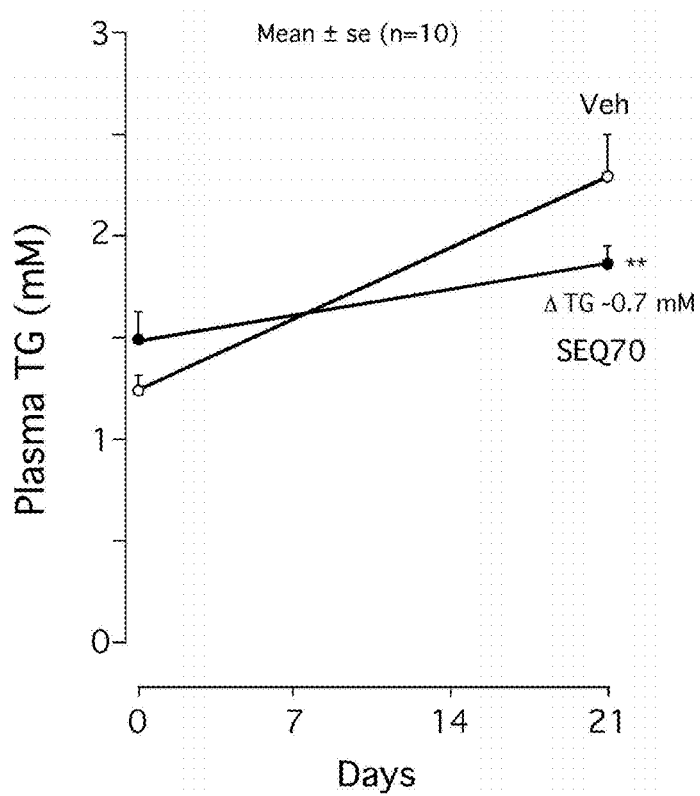
FIGS. 5A to 5B. Diabetic mice had their plasma triglyceride levels measured at baseline and after 3 weeks of treatment with PZ-235 versus vehicle.
Figure 5B:
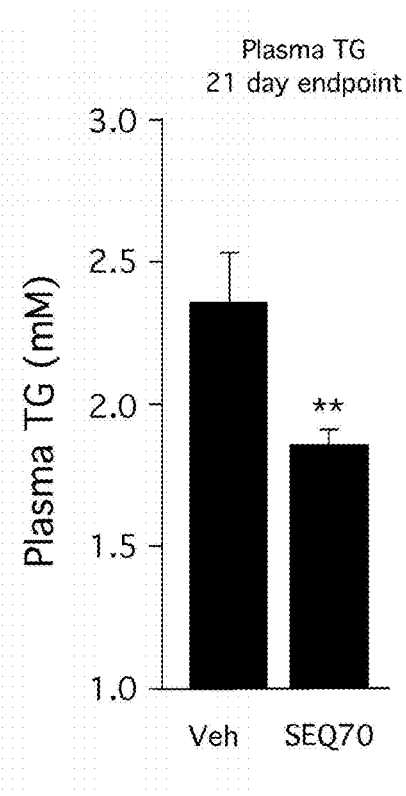
Figure 6:
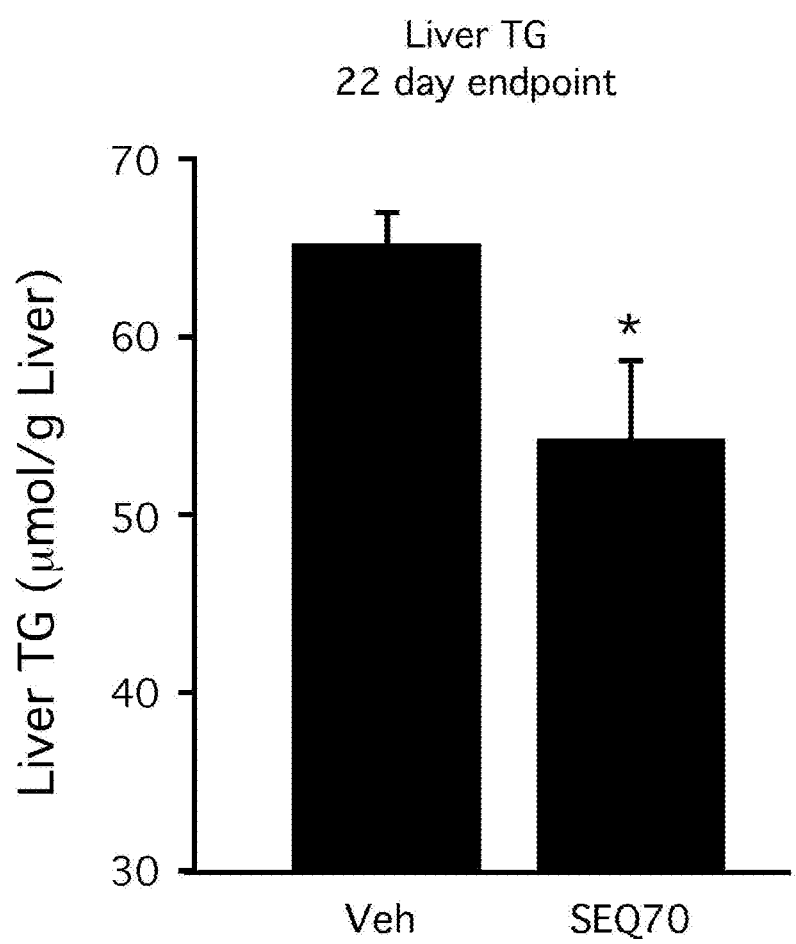
FIG. 6. Diabetic mice had their liver triglyceride levels measured after 3 weeks of treatment with PZ-235 versus vehicle. At termination of the 3 week experiment, livers were isolated from the diabetic mice, snap frozen and liver triglycerides measured.

Unless defined otherwise, all technical and scientific terms used herein have the same meaning as is commonly understood by one of skill in the art. The following definitions are provided to help interpret the disclosure and claims of this application. In the event a definition in this section is not consistent with definitions elsewhere, the definition set forth in this section shall control.

As used herein, the term "about" or "approximately" when used in conjunction with a number refers to any number within 1, 3, 5, 10 or 15% of the referenced number.

As used herein, "juxtamembrane" means close to the membrane.

As used herein, the term "peptide" or "polypeptide" refers to a molecule composed of monomers (amino acids) linearly linked by amide bonds (also known as peptide bonds). The term "polypeptide" refers to any chain or chains of two or more amino acids, and does not refer to a specific length of the product. A "peptide" or "polypeptide," as used herein, may be derived from a natural biological source or produced by recombinant technology, but is not necessarily translated from a designated nucleic acid sequence. It may be generated in any manner, including by chemical synthesis. One or more of the amino acids in an inventive polypeptide may be modified, for example, by the addition of a chemical entity such as a carbohydrate group, a phosphate group, a farnesyl group, an isofarnesyl group, a fatty acid group, an acyl group (e.g., acetyl group), a linker for conjugation, functionalization, or other known protecting or blocking groups. In certain embodiments, the modifications of the peptide lead to a more stable peptide (e.g., greater half-life in vivo).

The term "amino acid" refers to a molecule containing both an amino group and a carboxyl group. In certain embodiments, the amino acid is an alpha-amino acid. In certain embodiments, the amino acid is a natural amino acid. In certain embodiments, the amino acid is an non-natural amino acid. There are many known non-natural amino acids any of which may be included in the peptides of the present invention. See for example, S. Hunt, The Non-Protein Amino Acids: In Chemistry and Biochemistry of the Amino Acids, edited by G. C. Barrett, Chapman and Hall, 1985.

Exemplary amino acids include, without limitation, alpha-amino acids such as D- and L-isomers of the 20 common naturally occurring alpha amino acids found in peptides, natural amino acids which are not the 20 common naturally occurring amino acids, and unnatural alpha-amino acids. Amino acids used in the construction of peptides of the present invention may be prepared by organic synthesis, or obtained by other routes, such as, for example, degradation of or isolation from a natural source. Amino acids may be commercially available or may be synthesized. Amino acids with hydrophobic side chains include Gly, Pro, Ala, Ile, Leu, Val, Phe, Met, Trp, and Tyr. In certain embodiments, amino acids with hydrophobic side chains include Gly, Pro, Ala, Ile, Leu, Val, and Phe. In certain embodiments, amino acids with hydrophobic side chains include Ala, Ile, Leu, and Val. Amino acids with polar side chains include Gln, Asn, His, Ser, Thr, Tyr, Cys, Met, Trp. In certain embodiments, amino acids with polar side chains include Asn, Cys, Gln, Met, Ser, and Thr. Amino acids with aromatic side chains include Phe, Trp, Tyr, and His. Amino acids with hydrophobic aromatic side chains include Phe, Trp, and Tyr. Amino acids with charged side chains include Asp, Glu, Arg, His, and Lys. Negatively charged side chains include Asp and Glu. Positively charged side chains include Arg, His, and Lys. Neutral amino acids are selected from the group consisting of Ala, Ser, Val, Leu, Ile, Pro, Phe, Trp, Met, Gly, Thr, Cys, Tyr, Asn, and Gln.

As used herein, the terms "administration," "administering," or the like, when used in the context of providing a pharmaceutical composition to a subject, generally refers to providing to the subject one or more pharmaceutical compositions comprising the agent, e.g., an agonist or antagonist of the PAR2 signaling pathway, in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intra-peritoneal, transdermal, or buccal routes of delivery.

In one embodiment, "administration" of the agent, e.g., an agonist or antagonist of the PAR2 signaling pathway, to the patient may require controlled release, i.e., the release of the active ingredient from the formulation in a sustained and regulated manner over a longer period of time than an immediate release formulation containing the same amount of the active ingredient would release during the same time period. The dosage administered will be dependent upon the age, health, weight, and/or thrombotic disease state of the recipient and/or other associated risk factors, the kind of concurrent treatment, if any, the frequency of treatment, and/or the nature of the effect desired.

As used herein, an "agonist" refers to any natural or synthetic peptide, molecule, or combinations thereof that increases a biological activity above baseline of a control sample (e.g., buffer or a sample without peptide agonist) by at least about 1.5-fold, about 1.8-fold, about 2-fold, about 3-fold, about 4-fold, about 5-fold, about 7-fold, about 10 fold, about 20 fold, about 50 fold or about 100 fold or more in a standard bioassay or in vivo or when used in a therapeutically effective dose.

A "partial agonist" refers to any natural or synthetic peptide, molecule, or combinations thereof that increases a biological activity above baseline of a control sample by at least about 1.2-fold, about 1.3-fold, about 1.4-fold, or about 1.5-fold or more in a standard bioassay or in vivo or when used in a therapeutically effective dose.

An "antagonist" or "inhibitor" may be used interchangeably herein and refers to any any natural or synthetic peptide, molecule, or combinations thereof that interferes with a target's biological activity by at least about 10%, about 20%, about 30%, about 40%, about 50%, about 60%, about 70%, about 80%, about 85%, about 90%, about 95%, about 98%, or about 100% in a standard bioassay or in vivo or when used in a therapeutically effective dose.

As used herein, to "modulate" means to act as an antagonist, i.e., partially or fully inhibit, reduce, alleviate, block or prevent; or to increase or stimulate, i.e., to act as an agonist, partial agonist or inverse agonist. The modulation may be direct or indirect or allosteric.

Human wild-type PAR2 has the Genbank Accession Number XM-003671, which is hereby incorporated by reference. The sequence of human PAR2 is provided as SEQ ID NO: 33.

In this disclosure, reference to PAR family members in general or to any individual member of the PAR family member, such as PAR2, will be understood to refer to all splice variants, mutants (including, but not limited to, deletions, insertions, or polymorphisms or amino acid substitutions), isoforms, and homologues thereof.

The term, "patient" or "subject," as used herein, refers to any individual organism. For example, the organism may be a mammal such as a primate (i.e., for example, a human). Further, the organism may be a domesticated animal (i.e., for example, cats, dogs, etc.), livestock (i.e., for example, cattle, horses, pigs, sheep, goats, etc.), or a laboratory animal (i.e., for example, mouse, rabbit, rat, guinea pig, etc.).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "PEPDUCIN™" and "lipopeptide" are used interchangeably and are cell-penetrating peptides that act as intracellular inhibitors of signal transference from receptors to G proteins. Lipopeptides utilize lipidated fragments of intracellular G protein-coupled receptor loops to modulate GPCR action in targeted cell-signaling pathways. A lipopeptide comprises a short peptide derived from a GPCR intracellular loop tethered to a hydrophobic moiety. This structure allows lipopeptides to anchor in the cell membrane lipid bilayer and target the GPCR/G protein interface via a unique intracellular allosteric mechanism. Examples of PEPDUCIN™ lipopeptides are described in PCT Patent Publication No. WO2012/139137 and in U.S. Pat. Nos. 6,864,229; 8,324,172; 8,354,378; 8,389,480 ; 8,440,627; 8,563,519, each of which is incorporated here in by reference.

The term "therapeutically effective amount" as used herein means that amount of active peptide or composition thereof that elicits the biological or medicinal response in a tissue, system, animal, or human that is being sought by a researcher, veterinarian, medical doctor, or other clinician.

As used herein, "treating" or "treatment" cover the treatment of a thrombotic disease-state in a mammal, particularly in a human, and include, but not limited to: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The term "homologous," as used herein is an art-understood term that refers to nucleic acids or proteins that are highly related at the level of nucleotide or amino acid sequence. Nucleic acids or proteins that are homologous to each other are termed homologues. Homologous may refer to the degree of sequence similarity between two sequences (i.e., nucleotide sequence or amino acid). The homology percentage figures referred to herein reflect the maximal homology possible between two sequences, i.e., the percent homology when the two sequences are so aligned as to have the greatest number of matched (homologous) positions. Homology can be readily calculated by known methods such as those described in: Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. Methods commonly employed to determine homology between sequences include, but are not limited to those disclosed in Carillo, H., and Lipman, D., SIAM J Applied Math., 48:1073 (1988); incorporated herein by reference. Techniques for determining homology are codified in publicly available computer programs. Exemplary computer software to determine homology between two sequences include, but are not limited to, GCG program package, Devereux, J., et al., Nucleic Acids Research, 12(1), 387 (1984)), BLASTP, BLASTN, and PASTA Atschul, S. F. et al., J Molec. Biol., 215, 403 (1990)).

The term "homologous" refers to a comparison between two sequences. Two nucleotide sequences are considered to be homologous if the polypeptides they encode are at least about 50-60% identical, preferably about 70% identical, for at least one stretch of at least 20 amino acids. Preferably, homologous nucleotide sequences are also characterized by the ability to encode a stretch of at least 4-5 uniquely specified amino acids. Both the identity and the approximate spacing of these amino acids relative to one another must be considered for nucleotide sequences to be considered homologous. For nucleotide sequences less than 60 nucleotides in length, homology is determined by the ability to encode a stretch of at least 4-5 uniquely specified amino acids.

As used herein, the term "identity" refers to the overall relatedness between polymeric molecules, e.g., between nucleic acid molecules (e.g. DNA molecules and/or RNA molecules) and/or between polypeptide molecules. Calculation of the percent identity of two amino acid sequences, for example, can be performed by aligning the two sequences for optimal comparison purposes (e.g., gaps can be introduced in one or both of a first and a second amino acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The amino acids at corresponding positions are then compared. When a position in the first sequence is occupied by the same amino acid as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity can be calculated by optimal alignment of the sequences using a similarity-scoring matrix such as the Blosum62 matrix described in Henikoff S. and Henikoff J. G., *P.N.A.S. USA* 1992, 89: 10915-10919. Calculation of the percentage identity and optimal alignment of two sequences using the Blosum62 similarity matrix and the algorithm of Needleman and Wunsch (*J. Mol. Biol.* 1970. 48: 443-453) can be performed using the GAP program of the Genetics Computer Group (GCG, Madison, Wis., USA) using the default parameters of the program. Specific parameters for calculatimg percentage identity for protein sequences and nucleic acid sequences in respect of the present invention are described below.

A "rigidifier" or a "helix-breaker" moiety disrupts the regularity of the alpha-helical backbone conformation. Natural and unnatural amino acids can be a rigidifier/helix-breaker. Non-limiting examples of rigidifier/helix-breaker could be an amino acid such as Pro, Gly, Trp and Asn; a proline homolog with a 4, 5, 6 or 7 membered ring substituting for a proline side chain such as cyclo-butane, -pentane, -hexane, -heptane; an amino acid with a methyl-amino group at the peptide bond; 1-aminocyclopropanecarboxylic acid (ACC); para-aminobenzoic acid (Paba); alpha substituted Tyrosine analogues.

DETAILED DESCRIPTION

PEPDUCIN™ lipopeptides are cell-penetrating peptides or polypeptides developed to inhibit or activate GPCRs (see, e.g., U.S. Pat. Nos. 6,864,229 and 7,696,168). In certain embodiments, the lipopeptides inhibit GPCRs on the inside surface of the lipid bilayer. Provided herein are new peptides and lipopeptides targeting the protease-activated receptor 2 (PAR2) transmembrane receptor. The new peptides and lipopeptides provided herein include new mutations not previously taught in other PEPDUCIN™ literature. Studies have implicated PAR2 as playing a role in a wide range of diseases including asthma (Schmidlin et al., *J Immunol* 2002, 169: 5315-5321), arthritis (Ferrell et al., 2010), hyperalgesia (Vergnolle et al., 2001), neurogenic and cancer pain (Lam et al., 2010), cancer invasion (Shi et al., *Mol Cancer Res* 2004, 2: 395-402), non-alcoholic steatohepatitis (NASH), pulmonary arterial hypertension (PAH), atopic dermatitis (AD), pancreatitis, and IBD. A wide range of diseases involve PAR2 signaling, including many involving inflammatory, fibrotic, and metabolic reactions.

In certain embodiments, provided herein are chimeric polypeptides comprising: (a) a first domain comprising a mutated full-length or fragment of human protease-activated receptor-2 (PAR2); and (b) a second domain, attached to said first domain, wherein said second domain comprises a hydrophobic moiety; wherein said chimeric polypeptide is an effective PAR2 antagonist. In certain embodiments, the hydrophobic moiety is naturally occurring or non-naturally occurring.

In certain embodiments, the peptides described herein comprise a hydrophobic moiety. As used herein, the inventive peptides including at least one hydrophobic moiety are called lipopeptides. For example, the hydrophobic moiety attached to the peptides herein can be a lipid moiety, acyl moiety, steroid moiety, or an amino acid moiety, which are further described herein. The peptides and lipopeptides described herein typically target the intracellular surface of PAR2, resulting in modulation of signal transduction.

In certain embodiments, the peptide comprises a sequence of:

$X_4X_5X_6X_7X_8X_9X_{10}X_{11}X_{12}X_{13}X_{14}X_{15}X_{16}X_{17}X_{18}X_{19}X_{20}$ (SEQ ID NO: 42), wherein:

$X_4$ is absent, A, G, P, or an N-terminal linker;
$X_5$ is M, G, P, I, L, V, norleucine (J), methionine sulfoxide (M(SO)), or methionine sulfone (M(SO$_2$)), or absent when $X_4$ is absent;
$X_6$ is D, E, H, or absent when $X_4$ to $X_5$ are absent;
$X_7$ is D, E, H, or absent when $X_4$ to $X_6$ are absent;
$X_8$ is N, D, or E;
$X_9$ is any amino acid;
$X_{10}$ is any amino acid;
$X_{11}$ is any amino acid or D-amino acid thereof, 2-aminoisobutyric acid (B), hydroxyproline (Hyp), P, a proline homolog , G, or rigidifier/helix-breaker moiety;
$X_{12}$ is K, R, P or absent;
$X_{13}$ is any amino acid or citrulline (Cit);

$X_{14}$ is K or any amino acid that makes the peptide bond between $X_{13}$ and $X_{14}$ uncleavable, or any amino acid that reduces positive charge;

$X_{15}$ is any amino acid, or beta-A;

$X_{16}$ is A, S, T, G, Q, beta-A, 2-aminoisobutyric acid (B), or absent;

$X_{17}$ is I, A, L, or V;

$X_{18}$ is K, I, or F; and $X_{19}$ is a hydrophobic amino acid, a D-amino acid thereof, or absent.

In certain embodiments, the peptide comprises a sequence of:

$X_4X_5X_6X_7X_8SEX_{11}X_{12}X_{13}X_{14}X_{15}X_{16}X_{17}KX_{19}$(SEQ ID NO: 43), wherein:

$X_4$ is absent, A, G, P, or an N-terminal linker;

$X_5$ is M, G, P, I, L, V, norleucine (J), methionine sulfoxide (M(SO)), or methionine sulfone (M(SO$_2$)), or absent when $X_4$ is absent;

$X_6$ is D, E, H, or absent when $X_4$ to $X_5$ are absent;

$X_7$ is D, E, H, or absent when $X_4$ to $X_6$ are absent;

$X_8$ is N, D, or E;

$X_{11}$ is any amino acid or D-amino acid thereof, 2-aminoisobutyric acid (B), hydroxyproline (Hyp), P, a proline homolog , G, or rigidifier/helix-breaker moiety;

$X_{12}$ is K, R, P or absent;

$X_{13}$ is any amino acid or citrulline (Cit);

$X_{14}$ is K or any amino acid that makes the peptide bond between $X_{13}$ and $X_{14}$ uncleavable, or any amino acid that reduces positive charge;

$X_{15}$ is any amino acid, or beta-A;

$X_{16}$ is A, S, T, G, Q, beta-A, 2-aminoisobutyric acid (B), or absent;

$X_{17}$ is I, A, L, or V; and $X_{19}$ is a hydrophobic amino acid, a D-amino acid thereof, or absent.

In certain embodiments, the peptides comprise a sequence of SEQ ID NO: 43, wherein:

$X_4$ is absent, A, or an N-terminal linker;

$X_5$ is M, G, I, L, norleucine (J), M(SO), M(SO$_2$), or absent when $X_4$ is absent;

$X_6$ is D, E, H, or absent when $X_4$ to $X_5$ are absent;

$X_7$ is D, E, H, or absent when $X_4$ to $X_6$ are absent;

$X_8$ is N, D, or E;

$X_{11}$ is K, P, dP, 2-aminoisobutyric acid (B), hydroxyproline (Hyp), a proline homolog or rigidifier/helix-breaker moiety;

$X_{12}$ is K or absent;

$X_{13}$ is R, F, W, Y, citrulline (Cit), or another amino acid;

$X_{14}$ is K, dK, or another amino acid;

$X_{15}$ is Q, S, or beta-A;

$X_{16}$ is A, S, T, G, beta-A, 2-aminoisobutyric acid (B), or absent;

$X_{17}$ is I or A;

$X_{19}$ is a hydrophobic amino acid, a D-amino acid thereof; and $X_{20}$ is a hydrophobic amino acid, a D-amino acid thereof.

In certain embodiments, the peptide comprises a sequence of:

AIX$_6$X$_7$X$_8$SEX$_{11}$KX$_{13}$X$_{14}$X$_{15}$X$_{16}$X$_{17}$X$_{18}$X$_{19}$ (SEQ ID NO: 44), wherein the X variables are defined herein.

In certain embodiments, the peptide comprises a sequence of: AMX$_6$X$_7$X$_8$SEX$_{11}$KX$_{13}$X$_{14}$X$_{15}$X$_{16}$X$_{17}$X$_{18}$X$_{19}$ (SEQ ID NO: 45), wherein the X variables are defined herein.

In certain embodiments, the peptide comprises a sequence of: GLX$_6$X$_7$X$_8$SEX$_{11}$KX$_{13}$X$_{14}$X$_{15}$X$_{16}$X$_{17}$X$_{18}$X$_{19}$ (SEQ ID NO: 46), wherein the X variables are defined herein.

In certain embodiments, the peptide comprises a sequence of: GDENSEX$_{11}$KX$_{13}$X$_{14}$X$_{15}$X$_{16}$X$_{17}$X$_{18}$X$_{19}$ (SEQ ID NO: 47), wherein the X variables are defined herein.

In certain embodiments, the peptide comprises a sequence of: GDENX$_9$EX$_{11}$KX$_{13}$X$_{14}$X$_{15}$X$_{16}$X$_{17}$X$_{18}$X$_{19}$ (SEQ ID NO: 48), wherein the X variables are defined herein.

In certain embodiments, the peptide comprises a sequence of: GLHHDX$_9$EX$_{11}$KX$_{13}$X$_{14}$X$_{15}$X$_{16}$X$_{17}$X$_{18}$X$_{19}$ (SEQ ID NO: 49), wherein the X variables are defined herein.

In certain embodiments, the peptide comprises a sequence of: GLDENX$_9$EX$_{11}$KX$_{13}$X$_{14}$X$_{15}$X$_{16}$X$_{17}$X$_{18}$X$_{19}$ (SEQ ID NO: 50), wherein the X variables are defined herein.

In certain embodiments, the peptide comprises a sequence of: GLX$_6$X$_7$X$_8$X$_9$EX$_{11}$KX$_{13}$X$_{14}$X$_{15}$AIKX$_{19}$ (SEQ ID NO: 51), wherein the X variables are defined herein.

In certain embodiments, the peptide comprises a sequence of: GLHHDX$_9$EX$_{11}$KX$_{13}$X$_{14}$X$_{15}$AIKX$_{19}$ (SEQ ID NO: 52), wherein the X variables are defined herein.

In certain embodiments, the peptide comprises a sequence of: GLDENX$_9$EX$_{11}$KX$_{13}$X$_{14}$X$_{15}$AIKX$_{19}$ (SEQ ID NO: 53), wherein the X variables are defined herein.

In certain embodiments, the peptide comprises a sequence of: GLHHDSEX$_{11}$KX$_{13}$X$_{14}$X$_{15}$X$_{16}$X$_{17}$X$_{18}$X$_{19}$ (SEQ ID NO: 54), wherein the X variables are defined herein.

In certain embodiments, the peptide comprises a sequence of: GLDENSEX$_{11}$KX$_{13}$X$_{14}$X$_{15}$X$_{16}$X$_{17}$X$_{18}$X$_{19}$ (SEQ ID NO: 55), wherein the X variables are defined herein.

In certain embodiments, the peptide comprises a sequence of: GLX$_6$X$_7$X$_8$SEX$_{11}$KX$_{13}$X$_{14}$X$_{15}$AIKX$_{19}$(SEQ ID NO: 56), wherein the X variables are defined herein.

In certain embodiments, the peptide comprises a sequence of: GLHHDSEX$_{11}$KX$_{13}$X$_{14}$X$_{15}$AIKX$_{19}$(SEQ ID NO: 57), wherein the X variables are defined herein.

In certain embodiments, the peptide comprises a sequence of: GLDENSEX$_{11}$KX$_{13}$X$_{14}$X$_{15}$AIKX$_{19}$(SEQ ID NO: 58), wherein the X variables are defined herein.

In certain embodiments, the peptide comprises a sequence of: X$_4$X$_5$HHDX$_9$X$_{10}$X$_{11}$X$_{12}$X$_{13}$X$_{14}$X$_{15}$AIKX$_{19}$(SEQ ID NO: 59), wherein the X variables are defined herein.

In certain embodiments, the peptide comprises a sequence of: X$_4$X$_5$HHDSEX$_{11}$KX$_{13}$X$_{14}$X$_{15}$X$_{16}$X$_{17}$X$_{18}$X$_{19}$(SEQ ID NO: 60), wherein the X variables are defined herein.

In certain embodiments, the peptide comprises a sequence of: X$_4$X$_5$DENSEX$_{11}$X$_{12}$X$_{13}$X$_{14}$X$_{15}$X$_{16}$X$_{17}$X$_{18}$X$_{19}$ (SEQ ID NO: 61), wherein the X variables are defined herein.

In certain embodiments, the peptide comprises a sequence of: X$_4$X$_5$DENSEKX$_{12}$X$_{13}$X$_{14}$X$_{15}$X$_{16}$X$_{17}$X$_{18}$X$_{19}$ (SEQ ID NO: 62), wherein the X variables are defined herein.

In certain embodiments, the peptide comprises a sequence of: X$_4$X$_5$X$_6$X$_7$X$_8$X$_9$X$_{10}$X$_{11}$X$_{12}$X$_{13}$X$_{14}$X$_{15}$AIKX$_{19}$(SEQ ID NO: 63), wherein the X variables are defined herein.

In certain embodiments, the peptide comprises a sequence of: X$_4$X$_5$X$_6$X$_7$X$_8$SEX$_{11}$X$_{12}$X$_{13}$X$_{14}$X$_{15}$AIKX$_{19}$ (SEQ ID NO: 64), wherein the X variables are defined herein.

In certain embodiments, the peptide comprises a sequence of: X$_4$X$_5$X$_6$X$_7$X$_8$SEX$_{11}$X$_{12}$X$_{13}$X$_{14}$X$_{15}$X$_{16}$X$_{17}$X$_{18}$X$_{19}$ (SEQ ID NO: 65), wherein the X variables are defined herein.

In certain embodiments, the peptide comprises a sequence of: X$_4$X$_5$X$_6$X$_7$X$_8$X$_9$X$_{10}$KKRKX$_{15}$X$_{16}$X$_{17}$X$_{18}$X$_{19}$(SEQ ID NO: 66), wherein the X variables are defined herein.

In certain embodiments, the peptide comprises a sequence of: X$_4$X$_5$DX$_7$X$_8$X$_9$X$_{10}$X$_{11}$KX$_{13}$X$_{14}$X$_{15}$AIKX$_{19}$(SEQ ID NO: 67), wherein the X variables are defined herein.

In certain embodiments, the peptide comprises a sequence of: X$_4$LX$_6$X$_7$X$_8$SEX$_{11}$KX$_{13}$X$_{14}$X$_{15}$X$_{16}$IKX$_{19}$(SEQ ID NO: 68), wherein the X variables are defined herein.

In certain embodiments, a peptide comprising SEQ ID NO: 42-68 further comprises additional amino acid residues located at $X_1$, $X_2$, $X_3$, $X_{19}$, and/or $X_{20}$. In certain embodiments, a peptide comprising SEQ ID NO: 70 further comprises additional amino acid residues located at $X_{19}$, and/or $X_{20}$. In certain embodiments, the peptide further comprises $X_3$, which is located on the N-terminal side of $X_4$. In certain embodiments, the peptide further comprises $X_2X_3$. In certain embodiments, the peptide further comprises $X_1X_2X_3$. $X_1$, $X_2$, and $X_3$ are as defined further herein. In certain embodiments, the peptide does not comprise $X_{19}$ when $X_{20}$ is absent. $X_{19}$ is located on the C-terminal side of $X_{18}$. In certain embodiments, the peptide further comprises $X_{19}X_{20}$. $X_{19}$ and $X_{20}$ are as defined further herein.

In certain embodiments, the peptides comprise at least one insertion between any one of the amino acids positions. In certain embodiments, the peptides comprise at least two insertions between any one of the amino acids positions. In certain embodiments, the insertion is a P. In certain embodiments, the peptides comprise at least two P insertions between any one of the amino acids positions. In certain embodiments, the peptides comprise an insertion between amino acids $X_5$ and $X_6$; $X_{11}$ and $X_{12}$; or $X_{12}$ and $X_{13}$. In certain embodiments, the insertion is a P. In certain embodiments, the peptides comprise a P insertion between amino acids $X_5$ and $X_6$; $X_{11}$ and $X_{12}$; or $X_{12}$ and $X_{13}$.

As generally defined herein, $X_1$ is located on the N-terminal side of $X_2$ and can be R or K. In certain embodiments, $X_1$ is R.

As generally defined herein, $X_2$ is located on the N-terminal side of $X_3$ and can be S or T. In certain embodiments, $X_2$ is S.

As generally defined herein, $X_3$ is located on the N-terminal side of $X_4$ and can be S, G, P, an N-terminal linker, or a helix-breaker. In certain embodiments, $X_3$ is S, G, P. In certain embodiments, $X_3$ is an N-terminal linker is selected from the group consisting of eK and aminohexanoic acid (Ahx). In certain embodiments, $X_3$ is Ahx. In certain embodiments, $X_3$ is eK. In certain embodiments, $X_3$ is a helix-breaker as defined herein. In certain embodiments, $X_3$ is P. In certain embodiments, $X_3$ is G.

As generally defined herein, $X_4$ is an N-terminal linker, A, G, P, or absent. In certain embodiments, $X_4$ is eK or Ahx. In certain embodiments, $X_4$ is A, G, or P. In certain embodiments, $X_4$ is G. In certain embodiments, $X_4$ is A. In certain embodiments, $X_4$ is P. In certain embodiments, $X_4$ is absent.

As generally defined herein, $X_5$ is M, G, P, I, L, V, norleucine (J), methionine sulfoxide (M(SO)), or methionine sulfone (M(SO$_2$)), or absent. In certain embodiments, $X_5$ is M, G, P, I, L, or V. In certain embodiments, $X_4$ is absent and $X_5$ is M, G, P, I, L, V, norleucine (J), methionine sulfoxide (M(SO)), or methionine sulfone (M(SO$_2$)). In certain embodiments, $X_5$ is L or P (i.e., an insertion between $X_5$ and $X_6$). In certain embodiments, $X_5$ is L.

In certain embodiments, $X_4$ and $X_5$ are absent. In certain embodiments, $X_4$ and $X_5$ are both present. In certain embodiments, the peptide comprises the following amino acids: $X_4$ is P and $X_5$ is L. In certain embodiments, the peptide comprises the following amino acids: $X_4$ is eK, Ahx, G, or P; and $X_5$ is L. In certain embodiments, the peptide comprises the following amino acids: $X_4$ is G and $X_5$ is L or P. In certain embodiments, the peptide comprises the following amino acids: $X_4$ is G and $X_5$ is L. In certain embodiments, the peptide comprises the following amino acids: $X_4$ is A and $X_5$ is I. In certain embodiments, the peptide comprises the following amino acids: $X_4$ is A and $X_5$ is M. In certain embodiments, the peptide does not comprise $X_4$ and $X_5$ is M, G, P, I, L, or V.

As generally defined herein, $X_6$ is H, D, E, or absent when $X_4$ to $X_5$ are absent. In certain embodiments, $X_6$ is H. In certain embodiments, $X_6$ is D. In certain embodiments, $X_6$ is E.

As generally defined herein, $X_7$ is H, D, E, or absent when $X_4$ to $X_6$ are absent. In certain embodiments, $X_7$ is H. In certain embodiments, $X_7$ is D. In certain embodiments, $X_7$ is E.

In certain embodiments, the peptide does not comprise $X_1$ to $X_7$.

As generally defined herein, $X_8$ is D, E, or N. In certain embodiments, $X_8$ is N. In certain embodiments, $X_8$ is D. In certain embodiments, $X_8$ is E.

In certain embodiments, the peptide comprises the following amino acids: $X_6$ is H, D, or E, $X_7$ is H or E, and $X_8$ is D or E. In certain embodiments, $X_6$ is D, $X_7$ is H, and $X_8$ is N. In certain embodiments, the peptide comprises the following amino acids: $X_6$ is H, $X_7$ is H, and $X_8$ is D. In certain embodiments, $X_6$ is H, $X_7$ is H, and $X_8$ is E. In certain embodiments, $X_6$ is H, $X_7$ is H, and $X_8$ is N. In certain embodiments, $X_6$ is D, $X_7$ is E, and $X_8$ is N. In certain embodiments, $X_6$ is H, $X_7$ is E, and $X_8$ is N.

As generally defined herein, $X_9$ is any amino acid. In certain embodiments, $X_9$ is S, T, H, R, and K. In certain embodiments, $X_9$ is S or H. In certain embodiments, $X_9$ is S or T. In certain embodiments, $X_9$ is R or L.

As generally defined herein, $X_{10}$ is any amino acid. In certain embodiments, $X_{10}$ is E or D. In certain embodiments, $X_{10}$ is E. In certain embodiments, $X_{10}$ is D.

As generally defined herein, $X_{11}$ can be any amino acid or D-amino acid thereof, 2-aminoisobutyric acid (B), hydroxyproline (Hyp), P, a proline homolog, G, or rigidifier/helix-breaker moiety. In certain embodiments, $X_{11}$ is K. In certain embodiments, $X_{11}$ is 2-aminoisobutyric acid (B). In certain embodiments, $X_{11}$ is a rigidifier/helix-breaker moiety. In certain embodiments, $X_{11}$ is P or proline homolog. In certain embodiments, $X_{11}$ is P. In certain embodiments, $X_{11}$ is G. In certain embodiments, $X_{11}$ is dP or Hyp.

As generally defined herein, $X_{12}$ can be K, R, P, or absent. In certain embodiments, $X_{12}$ is K. In certain embodiments, $X_{12}$ is R. In certain embodiments, $X_{12}$ is P. In certain embodiments, $X_{12}$ is absent (i.e., a deletion).

In certain embodiments, the peptide comprises the following amino acids: $X_{11}$ is K and $X_{12}$ is K. In certain embodiments, the peptide comprises the following amino acids: $X_{11}$ is B; and $X_{12}$ is K. In certain embodiments, the peptide comprises the following amino acids: $X_{11}$ is P, dP, or Hyp; and $X_{12}$ is K. In certain embodiments, the peptide comprises the following amino acids: $X_{11}$ is K, P, dP, or Hyp; and $X_{12}$ is absent.

As generally defined herein, $X_{13}$ can be any amino acid or citrulline (Cit). In certain embodiments, $X_{13}$ is citrulline. In certain embodiments, $X_{13}$ is any neutral aromatic amino acid. In certain embodiments, $X_{13}$ is R. In certain embodiments, $X_{13}$ is F, W, or Y. In certain embodiments, $X_{13}$ is Y. In certain embodiments, $X_{13}$ is F. In certain embodiments, $X_{13}$ is W.

As generally defined herein, $X_{14}$ is K or any amino acid that makes the peptide bond between $X_{13}$ and $X_{14}$ uncleavable by proteases or any amino acid that reduces positive charge (i.e., neutral or negatively charged amino acids). In certain embodiments, $X_{14}$ is K. An amino acid that makes the peptide bonds uncleavable by proteases include D-amino acids or an amino acid with an N-methyl at the peptide bond. In certain embodiments, $X_{14}$ is any D-amino acid. In certain embodiments, $X_{14}$ is an amino acid with an N-methyl at the peptide bond. In certain embodiments, $X_{14}$ is any amino acid that reduces positive charge (i.e., neutral or negatively charged amino acids). In certain embodiments, $X_{14}$ is a dK. In certain embodiments, $X_{14}$ is a L, I, or V. In certain embodiments, $X_{14}$ is a dL, dI, or dV. In certain embodiments, $X_{14}$ is any amino acid that reduces positive charge (i.e., neutral or negatively charged amino acids). In certain embodiments, $X_{14}$ is a neutral amino acid. In certain embodiments, $X_{14}$ is a negatively charged amino acid. In certain embodiments, $X_{14}$ is a negatively charged side chain such as D and E. In certain embodiments, $X_{14}$ is a neutral charged side chain selected from A, S, V, L, I, P, F, W, M, G, T, C, Y, N, and Q.

As generally defined herein, $X_{15}$ is any amino acid, or beta-A. In certain embodiments, $X_{15}$ is a polar amino acid such as Q, N, H, S, T, Y, C, M, or W. In certain embodiments, $X_{15}$ is a polar amino acid such as Q or S. In certain embodiments, $X_{15}$ is W, Y, or F. In certain embodiments, $X_{15}$ is Q, S, or W. In certain embodiments, $X_{15}$ is beta-A.

As generally defined herein, $X_{16}$ is A, S, T, G, Q, N, beta-A, 2-aminoisobutyric acid (B), or absent (i.e., a deletion). In certain embodiments, $X_{16}$ is absent. In certain embodiments, $X_{16}$ is A, B, or Q. In certain embodiments, $X_{16}$ is A. In certain embodiments, $X_{16}$ is B. In certain embodiments, $X_{16}$ is Q.

As generally defined herein, $X_{17}$ is I, A, L, or V. In certain embodiments, $X_{17}$ is I or A. In certain embodiments, $X_{17}$ is A. In certain embodiments, $X_{17}$ is I.

As generally defined herein, $X_{18}$ is K, I, or F. In certain embodiments, $X_{18}$ is K or I. In certain embodiments, $X_{18}$ is I. In certain embodiments, $X_{18}$ is K. In certain embodiments, $X_{18}$ is F. In certain embodiments, $X_{18}$ is not F.

As generally defined herein, $X_{19}$ is a hydrophobic amino acid, a D-amino acid thereof, or any amino acid that makes the peptide bond between $X_{18}$ and $X_{19}$ uncleavable by a protease, or absent. In certain embodiments, $X_{19}$ is any amino acid that makes the peptide bond between $X_{18}$ and $X_{19}$ uncleavable by a protease. In certain embodiments, $X_{19}$ is G, P, A, I, L, V, F, or D-amino acids thereof. In certain embodiments, $X_{19}$ is L, I, V, dL, dI, or dV.

As generally defined herein, $X_{20}$ is on the C-terminal side of $X_{19}$ and is a hydrophobic amino acid, a D-amino acid thereof, any amino acid that makes the peptide bond between $X_{19}$ and $X_{20}$ uncleavable by a protease, or absent. In certain embodiments, $X_{20}$ is any amino acid that makes the peptide bond between $X_{19}$ and $X_{20}$ uncleavable by a protease. In certain embodiments, $X_{20}$ is G, P, A, I, L, V, F, or D-amino acids thereof. In certain embodiments, $X_{20}$ is L, I, V, dL, dI, or dV.

Any of the foregoing and subsequent embodiments and claimed embodiments recited for amino acids at positions $X_1$-$X_{20}$ are applicable to amino acids corresponding to positions 280 to 289 of the human PAR2 sequence and vice versa.

The wild-type PAR2 referred to herein can be from any source. In certain embodiments, the wild-type protease-activated receptor-2 (PAR2) is from primates or rodents. In certain embodiments, the wild-type PAR2 is from monkey. In certain embodiments, the wild-type PAR2 is from mouse or rat. In certain embodiments, the wild-type PAR2 is from human.

In certain embodiments, the peptide comprises an amino acid selected from SEQ ID NO: 1-68 and 70. Table 1 lists the exemplary peptide sequences. Positions $X_1$ to $X_{20}$ correspond to positions 270 to 289 of the human PAR2 sequence. Amino acids found at positions 274-287 of wild-type human PAR2 are shown as $X_5$ to $X_{18}$ of SEQ ID NO:41, which is provided in Table 1. As used herein, eK is epsilon lysine, Ahx is aminohexanoic acid, B is 2-aminoisobutyric acid, Hyp is hydroxyproline, Cit is citrulline, βA is beta-alanine, and J is norleucine. D-amino acids are indicated with a lower case d in front of the one-letter abbreviation (e.g., dK, dI, dP). A dash (-) indicates a deletion.

TABLE 1

| SEQ ID NO | Corresponding position in Human PAR2 | | | | | | | | | | | | | | | | | | | |
|---|---|---|---|---|---|---|---|---|---|---|---|---|---|---|---|---|---|---|---|---|
| | 270 $X_1$ | 271 $X_2$ | 272 $X_3$ | 273 $X_4$ | 274 $X_5$ | 275 $X_6$ | 276 $X_7$ | 277 $X_8$ | 278 $X_9$ | 279 $X_{10}$ | 280 $X_{11}$ | 281 $X_{12}$ | 282 $X_{13}$ | 283 $X_{14}$ | 284 $X_{15}$ | 285 $X_{16}$ | 286 $X_{17}$ | 287 $X_{18}$ | 288 $X_{19}$ | 289 $X_{20}$ |
| 1 | | | | | G | H | E | N | S | E | K | K | R | K | Q | A | I | K | | |
| 2 | | | | | G | D | H | N | S | E | K | K | R | K | Q | A | I | K | | |
| 3 | | | | | | | | D | S | E | K | K | R | K | Q | A | I | K | L | I |
| 4 | R | S | S | A | I | D | E | N | S | E | K | K | R | K | S | A | I | K | | |
| 5 | | | | | A | I | D | E | N | S | E | K | K | F | K | S | A | I | K | L |
| 6 | | | | | A | I | H | H | D | S | E | P | K | R | K | S | A | I | K | L |
| 7 | | | | | A | I | H | H | D | S | E | dP | K | R | K | S | A | I | K | L |
| 8 | | | | | A | I | H | H | D | S | E | dP | — | R | K | S | A | A | K | L |
| 9 | | | | | G | L | H | H | D | S | E | P | K | R | K | S | A | I | K | L | dI |
| 10 | | | | | G | L | H | H | D | S | E | P | K | R | dK | S | A | I | K | dV |
| 11 | | | | P | L | H | H | D | S | E | P | K | R | dK | S | A | I | K | dL |
| 12 | | eK | G | L | H | H | D | S | E | P | K | R | dK | S | A | I | K | L | dI |
| 13 | | eK | G | L | D | E | N | S | E | K | K | F | dK | S | A | I | K | L | dV |
| 14 | | | eK | L | D | E | N | S | E | K | K | F | dK | S | A | I | K | L | dV |
| 15 | | | | G | L | H | H | D | S | E | P | K | R | dK | S | B | I | K | dV |
| 16 | | | | G | L | H | H | D | S | E | P | K | R | dK | βA | — | I | K | dV |
| 17 | | | | Ahx | L | H | H | D | S | E | P | K | R | dK | S | A | I | K | dV |
| 18 | | | | G | L | H | H | D | S | E | P | K | R | dK | S | B | I | K | L | dV |
| 19 | | eK | G | L | D | E | N | S | E | K | K | F | dK | S | A | I | K | L | |
| 20 | | eK | A | I | D | E | N | S | E | K | K | F | K | S | A | I | K | L | | |
| 21 | | | | Ahx | L | H | H | D | S | E | P | K | R | dK | S | B | I | K | dV |
| 22 | | | | G | L | H | H | D | S | E | P | K | R | K | S | A | I | K | L | dV |
| 23 | | | eK | | L | H | H | D | S | E | P | K | R | K | S | A | I | K | L | dV |
| 24 | | | | | L | H | H | D | S | E | P | K | R | K | S | A | I | K | L | dV |
| 25 | | | | | A | M | D | E | N | S | E | K | K | Y | K | S | A | I | K | L |
| 26 | | | | | A | M | D | E | N | S | E | K | K | Cit | K | S | A | I | K | L |
| 27 | | | | | A | M | D | E | N | S | E | P | K | R | K | S | A | I | K | L |
| 28 | | | | | A | M | D | E | N | S | E | Hyp | K | R | K | S | A | I | K | L |

TABLE 1-continued

| SEQ ID NO | 270 $X_1$ | 271 $X_2$ | 272 $X_3$ | 273 $X_4$ | 274 $X_5$ | 275 $X_6$ | 276 $X_7$ | 277 $X_8$ | 278 $X_9$ | 279 $X_{10}$ | 280 $X_{11}$ | 281 $X_{12}$ | 282 $X_{13}$ | 283 $X_{14}$ | 284 $X_{15}$ | 285 $X_{16}$ | 286 $X_{17}$ | 287 $X_{18}$ | 288 $X_{19}$ | 289 $X_{20}$ |
|---|---|---|---|---|---|---|---|---|---|---|---|---|---|---|---|---|---|---|---|---|
| 29 | | | | G | L | H | H | D | S | E | P | K | R | K | S | A | I | K | L | I |
| 30 | | | | G | L | D | E | N | S | E | P | K | R | K | S | A | I | K | L | I |
| 31 | | | | | G | D | E | N | H | E | K | K | R | K | Q | A | I | K | | |
| 32 | | | | P | G | D | E | N | S | E | K | P | K | R | K | Q | A | I | K | |
| 33 | | | | G | P | D | E | N | S | E | K | K | P | R | K | Q | A | I | K | |
| 34 | | | | | G | D | E | N | S | E | K | K | Cit | K | Q | A | I | K | | |
| 35 | | | | | G | D | E | N | S | E | K | K | R | K | S | A | I | K | dA | |
| 36 | | | | | G | D | E | N | S | E | K | K | R | K | Q | A | I | K | L | |
| 37 | | | | | G | D | E | N | S | E | K | K | R | K | Q | A | I | K | L | I |
| 38 | | | | | G | D | E | N | S | E | K | K | R | K | Q | A | I | K | | |
| 39 | | | | | G | D | E | N | S | E | K | R | W | L | W | A | I | K | | |
| 40 | | | | | G | D | E | N | S | E | K | K | R | K | W | A | I | K | | |
| 41 | | | | | M | D | E | N | S | E | K | K | R | K | R | A | I | K | | |
| 70 | R | S | S | A | M | D | E | N | S | E | K | K | R | K | S | A | I | K | | |

In certain embodiments, the peptide comprises a sequence that is at least about 50%, 55%, 60%, 65%, 70%, 75%, 80%, 85%, 90%, 95%, or 99% homologous to any one of the amino acid sequences of SEQ ID NO: 1-68 and 70. In certain embodiments, the peptide comprises a sequence that is about 50% to about 99%, about 60% to about 99%, about 70% to about 99%, about 75% to about 99%, about 80% to about 99%, about 85% to about 99%, about 90% to about 99%, about 95% to about 99% homologous to any one of the amino acid sequences of SEQ ID NO: 1-68 and 70.

In certain embodiments, the peptide is at least 13 amino acids in length. In certain embodiments, the peptide is at least 15 amino acids in length. In certain embodiments, the peptide is at most 20 amino acids in length. In certain embodiments, the peptide is at most 25 amino acids in length. In certain embodiments, the peptide is 13-25 amino acids in length. In certain embodiments, the peptide is 13-20 amino acids in length. In certain embodiments, the peptide is 13-18 amino acids in length. In certain embodiments, the peptide is 15-25 amino acids in length. In certain embodiments, the peptide is 15-20 amino acids in length. In certain embodiments, the peptide is 15-18 amino acids in length. In certain embodiments, the peptide is 16-18 amino acids in length. In certain embodiments, the peptide is 15, 16, 17, 18, 19, 20, 21, 22, 23, 24, or 25 amino acids in length.

In certain embodiments, the peptide comprises at least one unnatural amino acid. In certain embodiments, the peptide comprises one or two unnatural amino acids. In certain embodiments, the peptide comprises at least one D-amino acid. In certain embodiments, the peptide comprises one or two D-amino acids. In certain embodiments, the peptide comprises 1-5 D-amino acids. In certain embodiments, the peptide comprises 1-10 D-amino acids. In certain embodiments, the peptide comprises all D-amino acids. In certain embodiments, the peptide comprises are at least 2000 Da in molecular weight.

In certain embodiments, the peptide comprises a sequence that is at least about 50%, 55%, 60%, 65%, 70%, 75%, 80%, 85%, 90%, 95%, or 99% identical to any one of the amino acid sequences of SEQ ID NO: 1-68 and 70. In certain embodiments, the peptide comprises a sequence that is about 50% to about 99%, about 60% to about 99%, about 70% to about 99%, about 75% to about 99%, about 80% to about 99%, about 85% to about 99%, about 90% to about 99%, about 95% to about 99% identical to any one of the amino acid sequences of SEQ ID NO: 1-68 and 70.

In certain embodiments, the peptide comprises the amino acid sequence of SEQ ID NO: 1-68 and 70 with 1, 2, 3, 4, 5, 6, 7, 8, 9, or 10 amino acid changes (e.g., amino acid substitutions, deletions, and/or additions). In certain embodiments, the amino acid change is an amino acid substitution in which 1, 2, 3, 4, 5, 6, 7, 8, 9, or 10 amino acids are mutated to another amino acid. In certain embodiments, the amino acid change is an addition or deletion, where the addition or deletion comprises adding or deleting up to 1, 2, 3, 4, 5, 6, 7, or 8 residues at the point of mutation in the wild type sequence. The residues being added or deleted can be consecutive or non-consecutive residues.

In another aspect, the peptides comprise a mutated fragment of a wild-type PAR2, wherein the peptide shares, in sequence, at least two sections of at least two contiguous amino acid residues with the wild-type PAR2 sequence. In certain embodiments, the at least two contiguous amino acid residues are found in amino acid positions of the wild-type PAR2 that correspond to amino acid positions 270-290 of a human PAR2 sequence, wherein at least one mutation in said mutated fragment of PAR2 is at the amino acid position corresponding to position 272, 273, 274, 275, 276, 277, 278, 279, 280, 281, 282, 283, 284, 285, 286, 287, 288, and/or 289 of the human PAR2 sequence. Additional sections of at least two contiguous amino acids are also contemplated. In certain embodiments, the peptide comprises 3 sections of at least 2 contiguous amino acids; a section of at least 2 and at least 3 contiguous amino acids; 2 sections of at least 3 contiguous amino acids; 3 sections of at least 3 contiguous amino acids; 2 sections of at least 3 contiguous amino acids and a section of at least 2 contiguous amino acids; a section of at least 3 contiguous amino acids and a section of at least 4 contiguous amino acids; a section of at least 3 contiguous amino acids, a section of at least 4 contiguous amino acids, and a section of at least 2 contiguous amino acids; 2 sections of at least 4 contiguous amino acids; or a section of at least 4 contiguous amino acids and a section of at least 6 contiguous amino acids with the wild-type PAR2 sequence. The sections of contiguous amino acids are separated by at least 1, 2, 3, 4, 5, 6, 7, 8, 9, 10, 11, or 12 amino acid residues. In certain embodiments, the amino acid residues which separate contiguous sections of amino acids are the same as those residues found at the corresponding position(s) of sequence of a wild-type PAR2 sequence. In certain embodiments, the amino acid residues which separate contiguous sections of amino acids are different from residues found at the corresponding position(s) of sequence of a wild-type PAR2 sequence.

In certain embodiments, the peptide comprises a mutated fragment of a wild-type protease-activated receptor-2 (PAR2), wherein the peptide shares, in sequence, at least three contiguous amino acid residues with the amino acids of the wild-type PAR2 at positions corresponding to positions 270-290 of a human PAR2 sequence, wherein at least one mutation in said mutated fragment of PAR2 is at the amino acid position corresponding to position 282 of the human PAR2 sequence.

In certain embodiments, the peptide comprises a mutated fragment of a wild-type protease-activated receptor-2 (PAR2), wherein the peptide shares, in sequence, at least three contiguous amino acid residues with the amino acids of the wild-type PAR2 at positions corresponding to positions 270-290 of a human PAR2 sequence, wherein at least one mutation in said mutated fragment of PAR2 is at the amino acid position corresponding to position 280 of the human PAR2 sequence.

In certain embodiments, the at least one mutation at an amino acid position is at the amino acid position corresponding to position 280 or 282 of the human PAR2 sequence but not at both positions 280 or 282. In certain embodiments, the at least one mutation at an amino acid position is at the amino acid positions corresponding to both position 280 and 282 of the human PAR2 sequence.

In certain embodiments, the least one mutation in said mutated fragment of PAR2 is at the amino acid position corresponding to position 273 of the human PAR2 sequence.

In certain embodiments, the least one mutation in said mutated fragment of PAR2 is at the amino acid position(s) corresponding to position 275, 276, and/or 277 of the human PAR2 sequence.

In certain embodiments, the least one mutation in said mutated fragment of PAR2 is at the amino acid position(s) corresponding to position 273, 274, 282, and/or 284 of the human PAR2 sequence.

In certain embodiments, the least one mutation in said mutated fragment of PAR2 is at the amino acid position(s) corresponding to position 274, 275, 276, 277, and/or 284 of the human PAR2 sequence. In certain embodiments, the peptide further comprises a mutation at an amino acid position corresponding to position 280 of the human PAR2 sequence.

In certain embodiments, the peptide described herein further comprises a mutation at the amino acid position corresponding to position 289 of the human PAR2 sequence.

In certain embodiments, the peptide described herein further comprises a mutation at the amino acid position corresponding to position 288 of the human PAR2 sequence.

In certain embodiments, the peptide described herein further comprises a mutation at the amino acid position corresponding to position 283 of the human PAR2 sequence.

In certain embodiments, the peptide described herein further comprises a mutation at the amino acid position corresponding to position 285 of the human PAR2 sequence.

In certain embodiments, the peptide described herein further comprises a mutation at the amino acid position corresponding to position 282 of the human PAR2 sequence.

In certain embodiments, the mutated fragment of PAR2 refers to the PAR2 sequence with amino acids corresponding to positions 270-290 of the human PAR2 sequence. In certain embodiments, the peptide described herein comprises at least one mutation in said mutated fragment of PAR2 at positions corresponding to position 273, 274, 275, 276, and/or 277 of the human PAR2 sequence. In certain embodiments, the peptide described herein comprises at least one mutation in said mutated fragment of PAR2 at positions corresponding to position 274, 284, or 287 of the human PAR2 sequence. In certain embodiments, the peptide comprises the sequence AIHHD (SEQ ID NO: 76) at the positions corresponding to positions 273-277 of the human PAR2 sequence. In certain embodiments, the peptide comprises the sequence AIDEN (SEQ ID NO: 77) at the positions corresponding to positions 273-277 of the human PAR2 sequence. In certain embodiments, the peptide comprises the sequence GLHHD (SEQ ID NO: 78) at the positions corresponding to positions 273-277 of the human PAR2 sequence. In certain embodiments, the peptide comprises the sequence GLDEN (SEQ ID NO: 79) at the positions corresponding to positions 273-277 of the human PAR2 sequence. In certain embodiments, the peptides described herein comprise at least one mutation in said mutated fragment of PAR2 at position corresponding to positions 273, 274, 282, and/or 284 of the human PAR2 sequence. In certain embodiments, the peptides described herein comprise at least one mutation in said mutated fragment of PAR2 at position corresponding to positions 274, 275, 276, 277, and/or 284 of the human PAR2 sequence. In certain embodiments, the peptide described herein comprises at least one mutation in said mutated fragment of PAR2 is at position corresponding to positions 275, 276, and/or 277 of the human PAR2 sequence. In certain embodiments, the peptide described herein comprises at least one mutation in said mutated fragment of PAR2 at the position corresponding to position 287 of the human PAR2 sequence. In certain embodiments, the peptide described herein comprises a mutation in said mutated fragment of PAR2 at the position corresponding to position 287 and a mutation at the position corresponding to position 274 or position 284 of the human PAR2 sequence. In certain embodiments, the peptide described herein further comprises a mutation at position corresponding to positions 289 of the human PAR2 sequence. In certain embodiments, the peptide described herein further comprises a mutation at position corresponding to positions 280 of the human PAR2 sequence.

In certain embodiments, the sections of contiguous amino acid residues of the peptides described are found in the third intracellular (i3) loop, the fifth transmembrane helix (TM5), and/or the sixth transmembrane helix (TM6) of PAR2. In certain embodiments, the sections of contiguous amino acid residues of the peptides described are located in positions of the wild-type PAR2 corresponding to amino acid residues within positions 270-290 of a human PAR2 sequence. In certain embodiments, the peptide shares, in sequence, three or more contiguous amino acid residues with the i3 loop of the wild type human PAR2. In certain embodiments, the peptide shares, in sequence, four or more contiguous amino acid residues, five or more contiguous amino acid residues, or six or more contiguous amino acid residues with the i3 loop of the wild type human PAR2. In certain embodiments, the peptide shares, in sequence, three or more contiguous amino acid residues with the TM6 of the wild type human PAR2. In certain embodiments, the peptide shares, in sequence, four or more contiguous amino acid residues, five or more contiguous amino acid residues, or six or more contiguous amino acid residues with the TM6 of the wild type human PAR2. In certain embodiments, the peptide shares, in sequence, two or more contiguous amino acid residues with the TM5 of the wild type human PAR2. In certain embodiments, the peptide shares, in sequence, three or more contiguous amino acid residues, four or more contiguous amino acid residues, five or more contiguous amino acid residues, or six or more contiguous amino acid residues with the TM5 of the wild type human PAR2.

In certain embodiments, the peptide shares, in sequence, at least 4, 5, 6, 7, 8, 9, or 10 contiguous amino acid residues with a human PAR2 sequence.

In certain embodiments, the peptide comprises 2-15 mutations compared to the wild-type PAR2 fragment from which the peptide is derived. In certain embodiments, the peptide has 2-10 mutations compared to the wild-type PAR2 fragment. In certain embodiments, the peptide has 5-10 mutations compared to the wild-type PAR2 fragment. In certain embodiments, the peptide has 5 mutations compared to the wild-type PAR2 fragment. In certain embodiments, the peptide has 6 mutations compared to the wild-type PAR2 fragment. In certain embodiments, the peptide has 7 mutations compared to the wild-type PAR2 fragment. In certain embodiments, the peptide has 8 mutations compared to the wild-type PAR2 fragment. In certain embodiments, the peptide has 9 mutations compared to the wild-type PAR2 fragment. In certain embodiments, the peptide has 10 mutations compared to the wild-type PAR2 fragment. In certain embodiments, the peptide has 11 mutations compared to the wild-type PAR2 fragment. In certain embodiments, the peptide has 12 mutations compared to the wild-type PAR2 fragment. In certain embodiments, the peptide has 6-12 mutations compared to the wild-type PAR2 fragment.

In certain embodiments, the peptides comprise S and E at the positions of the peptide corresponding to positions 278 and 279 of the human PAR2 sequence, respectively. In certain embodiments, the peptides comprise H and E at the positions of the peptide corresponding to positions 278 and 279 of the human PAR2 sequence, respectively. In certain embodiments, the peptides comprise K at the position of the peptide corresponding to positions 287 of the human PAR2 sequence. In certain embodiments, the peptides comprise S and E at the positions of the peptide corresponding to positions 278 and 279 of the human PAR2 sequence, respectively, and a K at the position of the peptide corresponding to positions 287 of the human PAR2 sequence.

In certain embodiments, the at least one mutation at the amino acid position corresponding to position 273 of the human PAR2 sequence is A, G, P, or an N-terminal linker. As used herein, an N-terminal linker includes, but is not limited to, eK, aminohexanoic acid (Ahx), proline, and glycine. In certain embodiments, the peptide does not include an amino acid that corresponds to position 273 when the starting residue on the N-terminus of the peptides is the amino acid corresponding to position 274 of the human PAR2 sequence.

In certain embodiments, the at least one mutation at the amino acid position corresponding to position 274 of the human PAR2 sequence is M, G, P, I, L, norleucine (J), methionine sulfoxide (M(SO)), or methionine sulfone (M(SO$_2$)). In certain embodiments, the peptide does not include an amino acid that corresponds to position 273 and 274 when the starting residue at the N-terminus of the peptide is the amino acid corresponding to position 275 of the human PAR2 sequence.

In certain embodiments, the at least one mutation at the amino acid position corresponding to position 275 of the human PAR2 sequence is D, E, H. In certain embodiments, the peptide does not comprise an amino acid that corresponds to positions 273, 274, and 275 when the starting residue at the N-terminus of the peptide is the amino acid corresponding to position 276 of the human PAR2 sequence.

In certain embodiments, the at least one mutation at the amino acid position corresponding to position 276 of the human PAR2 sequence is D, E, H. In certain embodiments, the N-terminus of the peptide is an amino acid corresponding to position 277. In certain embodiments, the peptide does not comprise an amino acid that corresponds to positions 273, 274, 275, and 276 when the starting residue at the N-terminus of the peptides is the amino acid corresponding to position 277 of the human PAR2 sequence.

In certain embodiments, the at least one mutation at the amino acid position corresponding to position 277 of the human PAR2 sequence is N, D, or E.

In certain embodiments, the at least one mutation at the amino acid position corresponding to position 278 of the human PAR2 sequence is any amino acid. In certain embodiments, the at least one mutation at the amino acid position corresponding to position 278 of the human PAR2 sequence is S, T, H, R, and K.

In certain embodiments, the at least one mutation at the amino acid position corresponding to position 279 of the human PAR2 sequence is any amino acid. In certain embodiments, the at least one mutation at the amino acid position corresponding to position 279 of the human PAR2 sequence is N, D, or E.

In certain embodiments, the at least one mutation at the amino acid position corresponding to position 280 of the human PAR2 sequence is any amino acid or D-amino acid thereof. In certain embodiments, the at least one mutation at the amino acid position corresponding to position 280 of the human PAR2 sequence is K, P, dP, 2-aminoisobutyric acid (B), hydroxyproline (Hyp), a proline homolog, G, or rigidifier/helix-breaker moiety.

In certain embodiments, the at least one mutation at the amino acid position corresponding to position 282 of the human PAR2 sequence is any amino acid or citrulline (Cit). In certain embodiments, the at least one mutation at the amino acid position corresponding to position 282 of the human PAR2 sequence is R, F, W, Y, or citrulline (Cit).

In certain embodiments, the at least one mutation at the amino acid position corresponding to position 284 of the human PAR2 sequence is any amino acid or beta-alanine (beta-A; β-A). In certain embodiments, the at least one mutation at the amino acid position corresponding to position 284 of the human PAR2 sequence is Q, S, or beta-alanine (beta-A; β-A).

In certain embodiments, the at least one mutation at the amino acid position corresponding to position 289 of the human PAR2 sequence is I, V, L, A, or a D-amino acid thereof.

In certain embodiments, the peptide described herein comprises at least one mutation in said mutated fragment of PAR2 at the position corresponding to positions 275, 276, and/or 277 of the human PAR2 sequence. In certain embodiments, the peptide comprises the sequence HHD corresponding to positions 275-277 of the human PAR2 sequence. In certain embodiments, the peptide comprises H at the positions corresponding to positions 275 and 276 of the human PAR2 sequence and a negatively charged amino acid (e.g., N, D, E) at the position corresponding to position 277 of the human PAR2 sequence. In certain embodiments, the peptide comprises the sequence DEN at positions corresponding to positions 275-277 of the human PAR2 sequence. In certain embodiments, the peptide comprises EN at positions corresponding to positions 276 and 277 and D or H at the position corresponding to position 275 of the human PAR2 sequence. In certain embodiments of any of the embodiments, the peptide further comprises SE at positions corresponding to 278 (i.e., $X_9$ of SEQ ID NO: 42) and 279 (i.e., $X_{10}$ of SEQ ID NO: 42) of the human PAR2 sequence.

In certain embodiments, the peptide does not comprise a K to F mutation at the position corresponding to position 287 (i.e., $X_{18}$ of SEQ ID NO: 42) of wild-type human PAR2. In certain embodiments, the peptide does not comprise a K to A mutation at the position corresponding to position 287 of wild-type human PAR2. In certain embodiments, the peptide does not comprise a M to A mutation at the position corresponding to position 274 (i.e., $X_5$ of SEQ ID NO: 42) of wild-type human PAR2. In certain embodiments, the peptide does not comprise a M to G mutation at the position corresponding to position 274 of wild-type human PAR2. In certain embodiments, the peptide does not comprise an R to S mutation at the position corresponding to position 284 (i.e., $X_{15}$ of SEQ ID NO: 42) of wild-type human PAR2. In certain embodiments, the peptide does not comprise an R to Q mutation at the position corresponding to position 284 of wild-type human PAR2.

As described herein, the peptide comprises amino acid additions, deletions, or substitutions compared to the corresponding wild-type PAR2. In certain embodiments, the peptide comprises a deletion at the position corresponding to position 281 (i.e., $X_{12}$ of SEQ ID NO: 42) of a human PAR2 sequence. In certain embodiments, the peptide comprises a deletion at the position corresponding to position 285 (i.e., $X_{16}$ of SEQ ID NO: 42) of a human PAR2 sequence. In certain embodiments, the peptide comprises a substitution or deletion of a methionine (M) with another residue at the position corresponding to position 274 of a human PAR2 sequence. In certain embodiments, the peptide comprises a substitution or deletion of an arginine (R) with another residue at the position corresponding to position 284 of a human PAR2 sequence. In certain embodiments, the peptide comprises a substitution of an arginine (R) with another residue with a shorter side chain at the position corresponding to position 284 of a human PAR2 sequence. In certain embodiments, the peptide comprises a substitution or deletion of a lysine (K) at the position corresponding to position 287 of a human PAR2 sequence.

In certain embodiments, the peptides comprise a sequence of SEQ ID NO: 41, wherein the amino acid sequence comprises a mutation at positions $X_5$ and $X_{15}$, wherein $X_5$ is M, G, P, I, L, norleucine (J), M(SO), M(SO$_2$), and wherein the peptide is at least 15 amino acids in length. In certain embodiments, the peptides comprise a sequence of SEQ ID NO: 41, wherein the amino acid sequence comprises a mutation at positions $X_5$ and $X_{15}$, wherein X5 is M, G, P, I, L, norleucine (J), M(SO), M(SO$_2$), wherein $X_{15}$ is S or Q, and wherein the peptide is at least 15 amino acids in length. In certain embodiments, the peptide is at most 20 amino acids in length. In certain embodiments, the peptide is at most 25 amino acids in length. In certain embodiments, the peptide is 15-25 amino acids in length. In certain embodiments, the peptide is 15-20 amino acids in length. In certain embodiments, the peptide is 15-18 amino acids in length. In certain embodiments, the peptide is 16-18 amino acids in length. In certain embodiments, the peptide is 15, 16, 17, 18, 19, 20, 21, 22, 23, 24, or 25 amino acids in length. In certain embodiments, the peptide comprises at least one unnatural amino acid. In certain embodiments, the peptide comprises one or two unnatural amino acids. In certain embodiments, the peptide comprises at least one D-amino acid. In certain embodiments, the peptide comprises one or two D-amino acids. In certain embodiments, the peptide comprises 1-5 D-amino acids. In certain embodiments, the peptide comprises 1-10 D-amino acids. In certain embodiments, the peptide comprises all D-amino acids. In certain embodiments, the peptide comprises are at least 2000 Da in molecular weight. In certain embodiments, the peptide exhibits at least 70% or at least 80% inhibition of PAR2 as assessed by calcium flux using 10 µM of the peptide and 8 µM SLIGRL (SEQ ID NO: 73) agonist in cells. In certain embodiments, the peptide exhibits at least 40% or at least 50% inhibition of PAR2 as assessed by calcium flux using 3 µM of the peptide and 8 µM SLIGRL (SEQ ID NO: 73) agonist in cells.

In certain embodiments, the peptides comprise a sequence of SEQ ID NO: 41, wherein the amino acid sequence comprises a mutation at positions $X_5$ and $X_{15}$, and further comprises an additional amino acid at position $X_4$ and $X_{19}$. In certain embodiments, the peptides comprise a sequence of SEQ ID NO: 41, wherein the amino acid sequence comprises a mutation at positions $X_5$ and $X_{15}$, and further comprises an additional amino acid at position $X_4$, $X_{19}$, and $X_{20}$. In certain embodiments, the additional amino acid position at $X_4$ is A. In certain embodiments, the additional amino acid position at $X_4$ is an N-terminal linker selected from the group consisting of eK, aminohexanoic acid (Ahx), proline, or glycine. In certain embodiments, the additional amino acid position at $X_4$ is eK. In certain embodiments, the additional amino acid position at $X_4$ is Ahx. In certain embodiments, the additional amino acid position at $X_4$ is proline. In certain embodiments, the additional amino acid position at $X_4$ is glycine. In certain embodiments, the additional amino acid position at $X_{19}$ is a hydrophobic amino acid, a D-amino acid thereof, or absent. In certain embodiments, the additional amino acid position at $X_{19}$ is a hydrophobic amino acid. In certain embodiments, the additional amino acid position at $X_{19}$ is A, I , L , F, V, P, or G. In certain embodiments, the additional amino acid position at $X_{19}$ is L. In certain embodiments, the additional amino acid position at $X_{19}$ is a D-amino acid of hydrophobic amino acid. In certain embodiments, the additional amino acid position at $X_{19}$ is a D-amino acid of L. In certain embodiments, the additional amino acid position at $X_{19}$ is a D-amino acid of V. Embodiments for $X_{19}$ are applicable to $X_{20}$. In certain embodiments, the peptides comprise a sequence of SEQ ID NO: 41, wherein the amino acid sequence comprises a mutation at positions $X_5$ and $X_{15}$, and further comprises an additional amino acid at position $X_4$ and $X_{19}$, wherein $X_4$ is G and $X_{19}$ is a hydrophobic amino acid or a D-amino acid thereof. In certain embodiments, the peptide is at most 20 amino acids in length. In certain embodiments, the peptide is at most 25 amino acids in length. In certain embodiments, the peptide is 15-25 amino acids in length. In certain embodiments, the peptide is 15-20 amino acids in length. In certain embodiments, the peptide is 15-18 amino acids in length. In certain embodiments, the peptide is 16-18 amino acids in length. In certain embodiments, the peptide is 15, 16, 17, 18, 19, 20, 21, 22, 23, 24, or 25 amino acids in length. In certain embodiments, the peptide comprises at least one unnatural amino acid. In certain embodiments, the peptide comprises one or two unnatural amino acids. In certain embodiments, the peptide comprises at least one D-amino acid. In certain embodiments, the peptide comprises one or two D-amino acids. In certain embodiments, the peptide comprises 1-5 D-amino acids. In certain embodiments, the peptide comprises 1-10 D-amino acids. In certain embodiments, the peptide comprises all D-amino acids. In certain embodiments, the peptide comprises are at least 2000 Da in molecular weight. In certain embodiments, the peptide exhibits at least 70% or at least 80% inhibition of PAR2 as assessed by calcium flux using 10 μM of the peptide.

In certain embodiments, the peptides comprise a sequence of SEQ ID NO: 41, wherein the amino acid sequence comprises a mutation at positions $X_5$ and $X_{15}$, and at least one mutation selected from: E or H at $X_6$; D or H at $X_7$; and D or E at $X_8$. In certain embodiments, the peptides comprise a sequence of SEQ ID NO: 41, wherein the amino acid sequence comprises a mutation at positions $X_5$ and $X_{15}$, and at least one mutation selected from: H at $X_6$; H at $X_7$; and D at $X_8$. In certain embodiments, the foregoing peptides comprise H at $X_6$; H at $X_7$; and D at $X_8$. In certain embodiments, the peptide is at most 20 amino acids in length. In certain embodiments, the peptide is at most 25 amino acids in length. In certain embodiments, the peptide is 15-25 amino acids in length. In certain embodiments, the peptide is 15-20 amino acids in length. In certain embodiments, the peptide is 15-18 amino acids in length. In certain embodiments, the peptide is 16-18 amino acids in length. In certain embodiments, the peptide is 15, 16, 17, 18, 19, 20, 21, 22, 23, 24, or 25 amino acids in length. In certain embodiments, the peptide comprises at least one unnatural amino acid. In certain embodiments, the peptide comprises one or two unnatural amino acids. In certain embodiments, the peptide comprises at least one D-amino acid. In certain embodiments, the peptide comprises one or two D-amino acids. In certain embodiments, the peptide comprises 1-5 D-amino acids. In certain embodiments, the peptide comprises 1-10 D-amino acids. In certain embodiments, the peptide comprises all D-amino acids. In certain embodiments, the peptide comprises are at least 2000 Da in molecular weight. In certain embodiments, the peptide exhibits at least 70% or at least 80% inhibition of PAR2 as assessed by calcium flux using 10 μM of the peptide.

In certain embodiments, the peptides comprise a sequence of SEQ ID NO: 41, wherein the amino acid sequence comprises a mutation at positions $X_5$ and $X_{15}$, and a D-amino acid at $X_{14}$. In certain embodiments, the peptides comprise a sequence of SEQ ID NO: 41, wherein the amino acid sequence comprises a mutation at positions $X_5$ and $X_{15}$, and an additional amino acid at $X_{19}$, wherein $X_{19}$ is a D-amino acid. In certain embodiments, the peptides comprise a sequence of SEQ ID NO: 41, wherein the amino acid sequence comprises a mutation at positions $X_5$ and $X_{15}$, and additional amino acids at $X_{19}$ and $X_{20}$, wherein $X_{20}$ is a hydrophobic amino acid or a D-amino acid. In certain embodiments, the peptides comprise a sequence of SEQ ID NO: 41, wherein the amino acid sequence comprises a mutation at positions $X_5$ and $X_{15}$, and additional amino acids at $X_{19}$, wherein $X_{14}$ and $X_{19}$ are D-amino acids. In certain embodiments, the peptides comprise a sequence of SEQ ID NO: 41, wherein the amino acid sequence comprises a mutation at positions $X_5$ and $X_{15}$, and additional amino acids at $X_{19}$ and $X_{20}$, wherein $X_{14}$ and $X_{20}$ are D-amino acids.

In certain embodiments, the peptides comprise a sequence of SEQ ID NO: 41, wherein the amino acid sequence comprises mutations at positions $X_5$ and $X_{15}$ and wherein the peptide is at least 15 amino acids in length. In certain embodiments, the foregoing peptides are at most 20 amino acids in length. In certain embodiments, the foregoing peptides are at least 2000 Da in length. In certain embodiments, the foregoing peptide exhibits at least 70% or at least 80% inhibition of PAR2 as assessed by calcium flux using 10 μM of the peptide and 8 μM SLIGRL (SEQ ID NO: 73) agonist in cells. In certain embodiments, the foregoing peptide exhibits at least 40% or at least 50% inhibition of PAR2 as assessed by calcium flux using 3 μM of the peptide and 8 μM SLIGRL (SEQ ID NO: 73) agonist in cells.

In certain embodiments, the peptide comprises at least one D-amino acid. In certain embodiments, the foregoing peptide comprises one or two D-amino acids. In certain embodiments, the peptide further comprises a mutation at position $X_{13}$. Embodiments for $X_{13}$ are described herein. In certain embodiments, the peptide further comprises a mutation at position X11. Embodiments for X11 are described herein. In certain embodiments, the foregoing peptides comprise a mutation at either X11 or X13 but not at both positions.

In certain embodiments, the peptide comprises a hydrophobic moiety. In certain embodiments, the peptide comprises at least two hydrophobic moieties. In certain embodiments, the peptide comprises at least three hydrophobic moieties. The hydrophobic moiety can be attached at the N-terminus, the C-terminus, and/or to an amino acid residue between the N- and C-terminus. The hydrophobic moiety enables the peptide to cross the cell membrane. In certain embodiments, the hydrophobic moiety is naturally occurring. In certain embodiments, the hydrophobic moiety is non-naturally occurring. In certain embodiments, the hydrophobic moiety comprises a lipid moiety, acyl moiety, steroid moiety, or an amino acid moiety. In certain embodiments, the hydrophobic moiety comprises a phospholipid, a cholesterol, a steroid, a sphingosine, a ceramide, an octylglycine, a 2-cyclohexylalanine, benzolylphenylalanine, or a C1 or C2 acyl group. In certain embodiments, the hydrophobic moiety comprises a steroid moiety. In certain embodiments, the steroid moiety is deoxycholic acid, lithocholic acid, or salts thereof. A steroid moiety can be coupled to a free amino group on the peptides such as one on the N-terminus or on an amino acid side chain.

The lipid moiety can be a straight chain fatty acid. In certain embodiments, the lipid moiety is selected from the group consisting of: capryloyl ($C_8$); nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phytanoyl (methyl substituted $C_{16}$); heptadecanoyl ($C_{17}$); stearoyl ($C_{18}$); nonadecanoyl ($C_{19}$); arachidoyl ($C_{20}$); heneicosanoyl ($C_{21}$); behenoyl ($C_{22}$); trucisanoyl ($C_{23}$); and lignoceroyl ($C_{24}$). In certain embodiments, the lipid moiety is myristoyl ($C_{14}$), pentadecanoyl ($C_{15}$), or palmitoyl ($C_{16}$). In certain embodiments, the hydrophobic moiety is palmitoyl.

The hydrophobic moiety may be attached to the peptide through amide bonds, ester bonds, ether bonds, carbon-carbon bonds, carbon-nitrogen bonds, carbon-oxygen bonds, or sulfur-sulfur bonds. The hydrophobic moiety may be attached to the peptide using groups on the peptide such as, but not limited to, sulfhydryls, amines, alcohols, and phenolic groups. Other peptide groups and types of bonds useful for attaching the hydrophobic moiety are known in the art. Other cell-penetrating and/or membrane-tethering hydrophobic moieties include cholesterol, phospholipids, steroids, sphingosine, ceramide, octyl-glycine, 2-cyclohexylalanine, benzoylphenylalanine, $C_1$ or $C_2$ acyl groups, or $C_3$-$C_8$ fatty acids.

In certain embodiments, the hydrophobic moiety is attached to the N-terminus, C-terminus, both the N-terminal and C-terminal ends of the peptide, or to an interior residue of the peptide (i.e., an amino acid between the C-terminal amino acid and the N-terminal amino acid).

In certain embodiments, the hydrophobic moiety is attached to the N-terminus of the peptide. In certain embodiments, the hydrophobic moiety is attached to the C-terminus of the peptide. In certain embodiments, the hydrophobic moiety is attached an interior residue of the peptide that is not located at the N-terminus or the C-terminus. In certain embodiments, the hydrophobic moiety is attached to a residue that is within 3 residues from the N-terminus. In certain embodiments, the hydrophobic moiety is attached to a residue that is within 5 residues of the N-terminus. In certain embodiments, the hydrophobic moiety is attached to a residue that is within 8 residues of the N-terminus. In certain embodiments, the hydrophobic moiety is attached to a residue that is within 3 residues of the C-terminus. In certain embodiments, the hydrophobic moiety is attached to a residue that is within 5 residues of the C-terminus. In certain embodiments, the hydrophobic moiety is attached to a residue that is within 8 residues of the C-terminus. The foregoing peptide locations of hydrophobic moiety are applicable to any of the peptides and various embodiments described herein.

In certain embodiments, the peptide is about 10-30 amino acids in length. In certain embodiments, the peptide is about 10-20 amino acids in length. In certain embodiments, the peptide is about 10-15 amino acids in length. In certain embodiments, the peptide is about 10, 11, 12, 13, 14, 15, 16, 17, 18, 19, 20, 21, 22, 23, 24, 25, 26, 27, 28, 29, or 30 amino acids in length. In certain embodiments, the peptide is at least 13 amino acids in length. In certain embodiments, the peptide is at least 15 amino acids in length. In certain embodiments, the peptide is at most 20 amino acids in length. In certain embodiments, the peptide is at most 25 amino acids in length. In certain embodiments, the peptide is 13-25 amino acids in length. In certain embodiments, the peptide is 13-20 amino acids in length. In certain embodiments, the peptide is 13-18 amino acids in length. In certain embodiments, the peptide is 15-25 amino acids in length. In certain embodiments, the peptide is 15-20 amino acids in length. In certain embodiments, the peptide is 15-18 amino acids in length. In certain embodiments, the peptide is 16-18 amino acids in length. In certain embodiments, the peptide is 15, 16, 17, 18, 19, 20, 21, 22, 23, 24, or 25 amino acids in length. The foregoing peptide lengths are applicable to any of the peptides and various embodiments described herein.

In certain embodiments, the peptide comprising a hydrophobic moiety has a molecular weight range of about 1500 Da to about 2500 Da. In certain embodiments, the peptide comprising a hydrophobic moiety has a molecular weight range of about 1700 Da to about 2300 Da. In certain embodiments, the peptide comprising a hydrophobic moiety has a molecular weight range of about 2000 Da to about 2300 Da. The foregoing molecular weight ranges are applicable to any of the peptides and various embodiments described herein.

In certain embodiments, the peptide has a solubility of up to about 30 mg/mL, about 40 mg/mL, about 50 mg/mL, about 60 mg/mL, about 100 mg/mL, or about 120 mg/mL in aqueous solution.

The peptides described herein can comprise L-amino acids, D-amino acids, or combinations thereof. In certain embodiments, all the residues in the peptide are L-amino acids. In certain embodiments, all the residues in the peptide are D-amino acids. In certain embodiments, the residues in the peptide are a combination of L-amino acids and D-amino acids. In certain embodiments, the peptides contain 1 to 5 residues that are D-amino acids. In certain embodiments, at least 5% of the peptide sequence comprises D-amino acids. In certain embodiments, at least 10% of the peptide sequence comprises D-amino acids. In certain embodiments, at least 20% of the peptide sequence comprises D-amino acids. In certain embodiments, at most 15% of the peptide sequence comprises D-amino acids. In certain embodiments, at most 20% of the peptide sequence comprises D-amino acids. In certain embodiments, at most 50% of the peptide sequence comprises D-amino acids. In certain embodiments, at most 60% of the peptide sequence comprises D-amino acids. In certain embodiments, at most 80% of the peptide sequence comprises D-amino acids. In certain embodiments, at most 90% of the peptide sequence comprises D-amino acids. In certain embodiments, about 5-15% of the peptide sequence comprises D-amino acids. In certain embodiments, about 5-20% of the peptide sequence comprises D-amino acids. In certain embodiments, about 5-50% of the peptide sequence comprises D-amino acids.

In certain embodiments, the peptide is a PAR2 antagonist. In certain embodiments, the peptide exhibits at least 30%, 40%, 50%, 60%, 70%, 80%, 85%, 90%, or 95% inhibition of PAR2. In certain embodiments, the peptide exhibits at least 70% inhibition of PAR2. In certain embodiments, the peptide exhibits at least 80% inhibition of PAR2. Various methods are known for measuring the antagonist activity. For example, antagonist activity can be measured with calcium flux experiments using, e.g., 3 µM or 10 µM of the peptide. A reduction of maximal calcium signal or slope of calcium influx indicates antagonist activity.

In certain embodiments, the peptides exhibits substantial antagonistic effect and no substantial agonistic effect. In certain embodiments, the peptides exhibit agonist activity that is less than about 30%, 25%, 20%, 15%, 10%, or 5%.

Methods of Use and Treatment

PAR2, a cell surface receptor for trypsin-like proteases, is widely expressed in inflammatory cells, mesenchymal cells (e.g. fibroblasts, myofibroblasts, smooth muscle cells), stromal cells, endothelium, hepatocytes, stellate cells, keratinocytes, pancreatic cells, nerve cells, cardiac cells, and epithelia including lung, intestinal, and hepatobiliary. PAR2 plays a key role in a number of acute and chronic inflammatory diseases of the skin, joints, lungs, brain, gastrointestinal tract and liver, and vascular systems, and has been implicated in the progression of liver, lung, kidney and other fibrotic diseases, atopic dermatitis, chronic and acute pain conditions, itch, and pulmonary arterial hypertension .

In addition to their well-recognized roles in vascular biology, PARs have also been proposed to be involved in the regulation of survival, apoptosis, and tumor growth (e.g., Yang et al., *Cancer Res* 2009, 69:6223-31). PAR2 is important in tumor cell biology in melanoma (Tellez C, et al., *Oncogene* 2003, 22:3130-37) and in hepatocellular carcinoma, and in the invasive and metastatic processes of breast, ovarian, colon, and pancreatic cancer.

PAR2 mediates a number of (patho)physiological pathways involved in acute and chronic inflammation, arthritis, allergic reactions, sepsis, inflammatory pain, as well as cancer cell invasion and metastasis. The pleiotropic downstream pathways activated by PAR2 include calcium mobilization, phospholipase C-β-dependent production of inositol phosphates and diacylglycerol, Rho and Rac activation, MAPK and beta-arrestin signaling and gene transcription (Ossovskaya et al., 2004, supra).

As a cell surface sensor of proteases, PAR2 endows the cell with the ability to respond or over-respond to the rapidly changing proteolytic microenvironment that occurs during inflammation. PAR2-deficient mice exhibit reduced granulocytic infiltration and tissue damage, and suppression of inflammatory cytokines in models of intestinal inflammation, autoimmunity, and encephalomyelitis (Noorbakhsh, et al., *J Exp Med* 2006, 203:425-35; Cenac et al., *Am J Pathol* 2002, 161:1903-15). Reduced cardiac ischemia/reperfusion injury was also observed in PAR2-deficient mice, which correlated with a decline in inflammatory mediators (Antoniak et al., *Arterioscler Thromb Vasc Biol.* 2010, 30: 2136-42). Conversely, overstimulation of PAR2 can lead to severe edema, granulocyte infiltration, increased tissue permeability, tissue damage and hypotension (Vergnolle et al., *Br J Pharmacol* 1999, 127: 1083-90; Cenac et al., 2002, supra). Agonists of PAR2 including trypsin and the synthetic SLIGRL (SEQ ID NO: 73) peptide also trigger the release of calcitonin and substance P from sensory neurons causing neutrophil infiltration, edema, hyperalgesia, and cancer pain (Vergnolle et al., *Nat Med* 2001, 7:821-26; Lam et al., *Pain* 2010, 149: 263-72). PAR2 has been linked to arthritis as evidenced by significant decreases in joint inflammation in PAR2-deficient mice (Ferrell et al. *J Clin Invest* 2003, 111: 35-41) and upregulated expression of the receptor in osteoarthritis and rheumatoid arthritis synovial tissues (Ferrell et al., *Ann Rheum Dis.* 2010, 69: 2051-2054). Sievert and colleagues (Knight V, Tchongue J, Lourensz D, Tipping P, Sievert W. Protease-activated receptor 2 promotes experimental liver fibrosis in mice and activates human hepatic stellate cells. *Hepatology* 2012; 55:879-87) showed that PAR2-deficient mice provide significant protection against liver fibrosis in mouse models. Recent reports by Ruf and Samad (Badeanlou L, Furlan-Freguia C, Yang G, Ruf W, Samad F. Tissue factor-protease-activated receptor 2 signaling promotes diet-induced obesity and adipose inflammation. Nat Med 2011; 17:1490-7) provide evidence for the role of macrophage derived tissue factor (TF) mediated PAR-2 signaling that leads to diet-induced obesity and adipose tissue inflammation.

Atopic Dermatitis (AD) or severe eczema is the most common chronic inflammatory skin disease present in about 18 million people in the US. Typical clinical manifestations include multiple inflamed lesions, erosions accompanied by lichenification, fibrotic papules, and severely dry skin with increased susceptibility to infection. A major uncontrolled symptom is intense itching and excessive scratching that can cause further excoriation, erosions and infections. Current prescription-based drug treatment consists of topical or systemic corticosteroids or calcineurin inhibitors for the most severely afflicted patients, which can exhibit severe side effects and are generally not suitable for long-term treatment. PAR2 has been identified as an important mediator in the pathogenesis of AD (Steinhoff, M., C. U. Corvera, M. S. Thoma, W. Kong, B. E. McAlpine, G. H. Caughey, J. C. Ansel, and N. W. Bunnett. Proteinase-activated receptor-2 in human skin: tissue distribution and activation of keratinocytes by mast cell tryptase. (1999) *Exp Dermatol* 8: 282-94; Lee, S. E., S. K. Jeong, and S. H. Lee. Protease and protease-activated receptor-2 signaling in the pathogenesis of atopic dermatitis. (2010) *Yonsei Med J* 51: 808-22). PAR2 is upregulated in multiple cell types in skin including keratinoctyes, inflammatory cells and sensory nerve endings during progression from acute to chronic dermatitis (Frateschi, S., E. Camerer, G. Crisante, S. Rieser, M. Membrez, R. P. Charles, F. Beermann, J. C. Stehle, B. Breiden, K. Sandhoff, S. Rotman, M. Haftek, A. Wilson, S. Ryser, M. Steinhoff, S. R. Coughlin, and E. Hummler. PAR2 absence completely rescues inflammation and ichthyosis caused by altered CAP1/Prss8 expression in mouse skin. (2011) *Nat Commun* 2: 161; Seeliger, S., C. K. Derian, N. Vergnolle, N. W. Bunnett, R. Nawroth, M. Schmelz, P. Y. Von Der Weid, J. Buddenkotte, C. Sunderkotter, D. Metze, P. Andrade-Gordon, E. Harms, D. Vestweber, T. A. Luger, and M. Steinhoff. Proinflammatory role of proteinase-activated receptor-2 in humans and mice during cutaneous inflammation in vivo. (2003) *FASEB J* 17: 1871-85; Rattenholl, A. and M. Steinhoff. Proteinase-activated receptor-2 in the skin: receptor expression, activation and function during health and disease. (2008) *Drug News Perspect* 21: 369-81; Buddenkotte, J., C. Stroh, I. H. Engels, C. Moormann, V. M. Shpacovitch, S. Seeliger, N. Vergnolle, D. Vestweber, T. A. Luger, K. Schulze-Osthoff, and M. Steinhoff. Agonists of proteinase-activated receptor-2 stimulate upregulation of intercellular cell adhesion molecule-1 in primary human keratinocytes via activation of NF-kappa B. (2005) *J Invest Dermatol* 124: 38-45). Increased protease activity in the skin from environmental sources (e.g. DerP/F from dust mites) and local inflammatory proteases such as mast cell tryptase (Kawakami, T., T. Ando, M. Kimura, B. S. Wilson, and Y. Kawakami. Mast cells in atopic dermatitis. (2009) *Curr Opin Immunol* 21: 666-78), kallikrein-5 and cathepsin S (Viode, C., O. Lejeune, V. Turlier, A. Rouquier, C. Casas, V. Mengeaud, D. Redoules, and A. M. Schmitt. Cathepsin S, a new pruritus biomarker in clinical dandruff/seborrhoeic dermatitis evaluation. (2014) *Exp Dermatol* 23: 274-5) contribute to aberrant PAR2 signaling and activation of the inflammatory response and itching (Briot, A., C. Deraison, M. Lacroix, C. Bonnart, A. Robin, C. Besson, P. Dubus, and A. Hovnanian. Kallikrein 5 induces atopic dermatitis-like lesions through PAR2-mediated thymic stromal lymphopoietin expression in Netherton syndrome. (2009) *J Exp Med* 206: 1135-47; de Veer, S. J., L. Furio, J. M. Harris, and A. Hovnanian. Proteases: common culprits in human skin disorders. (2014) *Trends Mol Med* 20: 166-178). Cleavage of PAR2 stimulates overexpression of the thymic stromal lymphopoietin (TSLP) (Duchatelet, S. and A. Hovnanian. Genetics of Atopic Dermatitis: Beyond Filaggrin-the Role of Thymic Stromal Lymphopoietin in Disease Persistence. (2014) *JAMA Dermatol* 150: 248-50) to trigger AD lesion formation and itch through a subset of C-fibers (Wilson, S. R., L. The, L. M. Batia, K. Beattie, G. E. Katibah, S. P. McClain, M. Pellegrino, D. M. Estandian, and D. M. Bautista. The epithelial cell-derived atopic dermatitis cytokine TSLP activates neurons to induce itch. (2013) *Cell* 155: 285-95).

Idiopathic pulmonary fibrosis (IPF), the most common of the interstitial lung diseases (ILDs), occurs in about 128,000 people, with 48,000 new cases diagnosed annually in the United States. The typical clinical course is a progressive fibrotic disease characterized by scarring and 'honeycombing' of the lungs causing an irreversible loss of the tissue's ability to transport oxygen. Co-morbid pulmonary hypertension is commonly seen in patients with IPF and contributes to a worsening clinical prognosis. IPF ultimately robs a patient of the ability to breathe leading to a mortality rate of 66% at 5 years following diagnosis. This corresponds to an unappreciated large number of deaths per year (n=40,000), about the same yearly rate as deaths due to breast cancer. Current treatments have mainly focused on blocking proliferation of lung fibroblasts. The pan-tyrosine kinase inhibitor, nintedanib, appears to have some benefit in patient-important outcomes (slower disease progression), although no significant effect on mortality was detected in 3 clinical trials. Pirfenidone, an IPF drug with an unknown mechanism of action, showed both a slight reduction in mortality and a reduced rate of forced vital capacity (FVC) decline. Despite the appearance of these two-newly approved drugs, there still remains no truly effective treatment for IPF—especially for subjects with more advanced disease—and significant GI and hepatic toxicity occurs with both drugs and pirfenidone induces rash/photosensitivity. PAR2 has recently been identified as an important mediator in the pathogenesis of IPF (Wygrecka, M., G. Kwapiszewska, E. Jablonska, S. von Gerlach, I. Henneke, D. Zakrzewicz, A. Guenther, K. T. Preissner, and P. Markart. Role of protease-activated receptor-2 in idiopathic pulmonary fibrosis. (2011) *Am J Respir Crit Care Med* 183: 1703-14; Wygrecka, M., B. K. Dahal, D. Kosanovic, F. Petersen, B. Taborski, S. von Gerlach, M. Didiasova, D. Zakrzewicz, K. T. Preissner, R. T. Schermuly, and P. Markart. Mast cells and fibroblasts work in concert to aggravate pulmonary fibrosis: role of transmembrane SCF and the PAR-2/PKC-alpha/Raf-1/p44/42 signaling pathway. (2013) *Am J Pathol* 182: 2094-108; Park, Y. S., C. M. Park, H. J. Lee, J. M. Goo, D. H. Chung, S. M. Lee, J. J. Yim, Y. W. Kim, S. K. Han, and C. G. Yoo. Clinical implication of protease-activated receptor-2 in idiopathic pulmonary fibrosis. (2012) *Respir Med* 107: 256-62). PAR2 is upregulated in lung epithelium, fibroblasts, and inflammatory cells during progression of IPF, and IPF patients with high expression of PAR2 in lung have worse over-all survival and lung honeycombing. Increased pro-coagulant protease (factors VIIa/Xa/TF) activity in the lung and local inflammatory proteases such as mast cell tryptase trigger aberrant PAR2 signaling and activation of the fibrotic response. Mast cell numbers in the lungs of patients with fibrotic lung disease are also increased and correlate with fibrosis severity. Proteolytic cleavage of PAR2 stimulates overexpression of TGF-β to trigger fibroblast lesion formation and αSMA production through ERK1/2 pathways. Thus, effective blockade of PAR2 would interrupt a chronic positive feedback mechanism driven by tryptase and procoagulant protease activation of PAR2 on lung epithelium, fibroblasts and inflammatory cells, and suppress the fibrotic response in IPF patients to act as a unique disease-modifying agent.

Increased PAR2 expression was also documented in pancreatic and experimental rat liver fibrosis and was shown to correlate with the extent of interstitial fibrosis in IgA nephropathy (Michael, E. S., A. Kuliopulos, L. Covic, M. L. Steer, and G. Perides. Pharmacological inhibition of PAR2 with the pepducin P2pal-18S protects mice against acute experimental biliary pancreatitis. (2013) *Am J Physiol Gastrointest Liver Physiol* 304: G516-26; Grandaliano, G., P. Pontrelli, G. Cerullo, R. Monno, E. Ranieri, M. Ursi, A. Loverre, L. Gesualdo, and F. P. Schena. Protease-activated receptor-2 expression in IgA nephropathy: a potential role in the pathogenesis of interstitial fibrosis. (2003) *J Am Soc Nephrol* 14: 2072-83; Ikeda, O., H. Egami, T. Ishiko, S. Ishikawa, H. Kamohara, H. Hidaka, S. Mita, and M. Ogawa. Expression of proteinase-activated receptor-2 in human pancreatic cancer: a possible relation to cancer invasion and induction of fibrosis. (2003) *Int J Oncol* 22: 295-300). In pulmonary diseases, high expression of PAR2 has been observed in PAH (Kwapiszewska, G., P. Markart, B. K. Dahal, B. Kojonazarov, L. M. Marsh, R. T. Schermuly, C. Taube, A. Meinhardt, H. A. Ghofrani, M. Steinhoff, W. Seeger, K. T. Preissner, A. Olschewski, N. Weissmann, and M. Wygrecka. PAR-2 inhibition reverses experimental pulmonary hypertension. (2012) *Circ Res* 110: 1179-91), bronchopulmonary dysplasia and infant respiratory distress syndrome (Cederqvist, K., C. Haglund, P. Heikkila, M. D. Hollenberg, R. Karikoski, and S. Andersson. High expression of pulmonary proteinase-activated receptor 2 in acute and chronic lung injury in preterm infants. (2005) *Pediatr Res* 57: 831-6). PAR2 was localized to hyperplastic ATII cells and fibroblasts/myofibroblasts in fibrotic lungs. In addition, fibroblasts isolated from IPF lungs showed significantly higher PAR2 levels than did fibroblasts extracted from donor lungs. TGF-β, a cytokine known to be crucially involved in the pathogenesis of IPF, strongly induced PAR2 synthesis in donor lung fibroblasts. Although quiescent tissue fibroblasts constitutively express lower levels of PAR2, conditions that promote fibroblast activation considerably increase PAR2 expression. Thus, transformation of PAR2-low to PAR2-high positive fibroblasts occurs in wound models as well as in normal and hypertrophic scars of humans (Materazzi, S., S. Pellerito, C. Di Serio, M. Paglierani, A. Naldini, C. Ardinghi, F. Carraro, P. Geppetti, G. Cirino, M. Santucci, F. Tarantini, and D. Massi. Analysis of protease-activated receptor-1 and -2 in human scar formation. (2007) *J Pathol* 212: 440-9). Taken together, these data support a mechanism whereby tissue injury/damage triggers PAR2 induction and activation by extracellular proteases that drives physiological tissue repair to a pathological tissue response culminating in fibrosis in patients.

Tryptase, a major pro-inflammatory serine protease, can also cleave and activate PAR2. Local or systemic release of high levels of mast cell-derived tryptase can have life-threatening consequences including acute asthma, systemic mastocytosis, and anaphylaxis (Caughey, *Immunol Rev* 2007, 217: 141-54) and contribute to idiopathic pulmonary fibrosis. A specific and effective pharmacological inhibitor of PAR2 therefore has the potential to provide beneficial anti-inflammatory effects and reduce the detrimental activity of mast cells, neutrophils, monocytes/macrophages, T cells, and other PAR2-expressing leukocytes that contribute to tissue damage.

The new peptides, which include the lipopeptide versions, are useful for targeting the signaling events regulated by PAR2s as well as its upstream or downstream effects. For example, the peptides, lipopeptides, and compositions herein are used to treat diseases or conditions associated with increased or aberrant PAR2 activity or signaling or associated with increased or aberrant PAR2 protease activity. The peptides and compositions herein can also be used to treat constitutive PAR2 activity. Provided herein are methods of treating a disease or condition associated with PAR2 in a subject in need thereof comprising administering an effective amount of a peptide or lipopeptides, as described herein to the subject. Provided herein are methods of treating a disease or condition associated with PAR2 in a subject in need thereof comprising instructing the subject to take an effective amount of a peptide as described herein to the subject. Also provided herein are peptides for use in treating a disease or condition associated with PAR2 in a subject in need thereof.

In certain embodiments, the peptides and lipopeptides herein are useful in methods of treatment for various PAR2 disorders which include, but are not limited to, non-alcoholic steatohepatitis (NASH), idiopathic pulmonary fibrosis (IPF), atopic dermatitis (AD, eczema), kidney fibrosis, alcoholic steatohepatitis, organ fibrosis, kidney fibrosis, bone marrow fibrosis, pulmonary arterial hypertension (PAH), lung fibrosis, pruritis (itch), pancreatitis, chronic kidney disease, nephritis, multiple sclerosis, cancer, leukemia, melanoma, inflammatory disorders and conditions, sepsis, inflammation-related CNS disorders, bronchitis, asthma, diabetes, complications of diabetes and NASH, obesity, metabolic syndrome, fibrotic diseases, cardiac fibrosis, pulmonary fibrosis, inflammatory bowel disease, Crohn's disease, irritable bowel syndrome, cirrhosis, arthritis, arthrofibrosis, keloids, myelofibrosis, systemic fibrosis, scleroderma, psorasis, hives, impetigo, rashes, and rosacea. In certain embodiments, the disorder is alcoholic steatohepatitis (NASH), idiopathic pulmonary fibrosis (IPF), atopic dermatitis (AD, eczema), kidney fibrosis, alcoholic steatohepatitis, organ fibrosis, kidney fibrosis, bone marrow fibrosis, pulmonary arterial hypertension (PAH), lung fibrosis, pruritis (itch), pancreatitis, chronic kidney disease, nephritis, multiple sclerosis, cancer, leukemia, melanoma, inflammatory disorders and conditions, sepsis, inflammation-related CNS disorders, bronchitis, asthma, diabetes, complications of diabetes and NASH, obesity, metabolic syndrome, fibrotic diseases, cardiac fibrosis, pulmonary fibrosis, inflammatory bowel disease, Crohn's disease, irritable bowel syndrome, cirrhosis, arthritis, arthrofibrosis, keloids, myelofibrosis, systemic fibrosis, scleroderma, psoriasis, hives, impetigo, rashes, or rosacea. In certain embodiments, the PAR2 disorder is NASH. In certain embodiments, the disorder is NASH. In certain embodiments, the disorder is diabetes. In certain embodiments, the PAR2 disorder is a cancer is selected from the group consisting of cancers of the colon, skin, melanocytes, breast, prostate, central nervous system, brain, immune system, pancreas, head and neck, esophagus, kidney, reproductive system, ovary, endometrium, and cervix. In certain embodiments, the disorder is a cancer is selected from the group consisting of cancers of the colon, skin, melanocytes, breast, prostate, central nervous system, brain, immune system, pancreas, head and neck, esophagus, kidney, reproductive system, ovary, endometrium, and cervix.

In certain embodiments, the peptides and lipopeptides herein are useful in methods of treatment for conditions that involve inflammation. In certain embodiments, the peptides and lipopeptides herein are useful in methods of treatment for pancreatitis, asthma, rheumatoid arthritis, osteoarthritis, cancer, chronic pain, visceral pain, cancer pain, multiple sclerosis, inflammatory bowel disease, irritable bowel syndrome, mast-cell diseases, mastocytosis, Gout, sepsis, arterial restenosis, atherosclerosis, inflammatory diseases of the airways and gastrointestinal tract, itching, ichthyoses, pruritis, inflammatory skin diseases, psoriasis, and Alzheimer's Disease.

In certain embodiments, the peptides and lipopeptides herein are useful in methods of treatment for decreasing glycosylated hemoglobin (HbA1c) levels by about 0.5% to about 1.0% in a subject treated with peptides and lipopeptides, in comparison with a vehicle control group not treated with the peptides and lipopeptides. In certain embodiments, the peptides and lipopeptides herein are useful for decreasing HbA1c levels by about 0.4% to about 1.0%, about 0.5% to about 1.0%, about 0.6% to about 1.0%, about 0.8% to about 1.0%, or about 0.9% to about 1.0%. In certain embodiments, the peptides and lipopeptides herein are useful for decreasing HbA1c levels by about 0.4%, 0.5%, 0.6%, 0.7%, 0.8%, or 0.9%. In certain embodiments, the peptides and lipopeptides herein are useful in methods of treatment for decreasing insulin levels by about 40% to about 60% in a subject treated with peptides and lipopeptides, in comparison with a vehicle control group not treated with the peptides and lipopeptides. In certain embodiments, the peptides and lipopeptides herein are useful for decreasing insulin levels by about 40% to about 60%, about 45% to about 60%, about 45% to about 50%, about 50% to about 60%, about 50% to about 55%, or about 55% to about 60%. In certain embodiments, the peptides and lipopeptides herein are useful for decreasing insulin levels by about 40%, about 45%, about 50%, about 55%, or about 60%. In certain embodiments, the subject is a mammal. In certain embodiments, the subject is a human. In certain embodiments, the subject is a non-human animal.

Pharmaceutical Compositions

Provided herein are pharmaceutical compositions comprising a peptide as described herein and a pharmaceutically acceptable excipient. Pharmaceutical compositions comprise compositions for therapeutic use. Such compositions may optionally comprise one or more additional therapeutically active agents. The antagonist peptides may be administered to mammals in need of treatment, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration. The phrase "active ingredient" or "agent" generally refers to a peptide as described herein.

Although the descriptions of pharmaceutical compositions provided herein are principally directed to pharmaceutical compositions for administration to humans, it will be understood by the skilled artisan that such compositions are generally suitable for administration to animals of all sorts. Modification of pharmaceutical compositions for administration to various animals is well understood, and the ordinarily skilled veterinary pharmacologist can design and/or perform such modification with merely ordinary, if any, experimentation.

Pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable excipient, and/or any additional ingredients in a pharmaceutical composition of the invention will vary, depending upon the identity, size, and/or disorder of the subject treated and further depending upon the route by which the composition is to be administered. By way of example, the composition may comprise between 0.1% and 100% (w/w) active ingredient.

As used herein, a pharmaceutically acceptable excipient includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy,* $21^{st}$ Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional carrier medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by the United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the Formulator.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxy-anisol or alpha-tocopherol.

Dispersible powders and granules suitable for preparation of an aqueous suspension by the addition of water provide the active ingredient in admixture with a dispersing or wetting agent, suspending "agent" and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol. The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

When a composition according to this invention is administered into a human subject, the prescribing physician will normally determine the daily dosage with the dosage generally varying according to the age, weight, and response of the individual patient, as well as the severity of the patient's symptoms. In an embodiment, a suitable amount of an "agent" is administered to a mammal undergoing treatment for thrombosis. Administration occurs in an amount of "agent" of between about 0.1 mg/kg of body weight to about 60 mg/kg of body weight per day, or between 0.5 mg/kg of body weight to about 40 mg/kg of body weight per day. Another therapeutic dosage that comprises the instant composition includes from about 0.01 mg to about 1000 mg of agent. In another embodiment, the dosage comprises from about 1 mg to about 5000 mg of agent.

Kits

According to another aspect, kits comprising one or more of the compositions (e.g., those comprising a provided peptide or composition for producing same). A "kit," as used herein, typically defines a package or an assembly including one or more of the compositions of the invention, and/or other compositions associated with the invention, for example, as described herein. The kit may include isolated or purified peptides, lipopeptides, polynucleotides, vectors encoding provided peptides, and/or cells expressing or capable of expressing provided peptides, and combinations thereof. Each of the compositions of the kit may be provided in liquid form (e.g., in solution), in solid form (e.g., a dried powder), or may be in a suspension, such as a frozen suspension of cells. In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, and the like, for example, for using, administering, modifying, assembling, storing, packaging, preparing, mixing, diluting, and/or preserving the compositions components for a particular use, for example, to a sample and/or a subject.

A kit may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, activation, mixing, diluting, preserving, administering, assembly, storage, packaging, and/or preparation of the composition and/or other compositions associated with the kit. In some cases, the instructions may also include instructions for the delivery and/or administration of the compositions, for example, for a particular use, e.g., to a material and/or a subject.

EXAMPLES

In order that the invention described herein may be more fully understood, the following examples are set forth. It should be understood that these examples are for illustrative purposes only and are not to be construed as limiting this invention in any manner.

Peptides found in Table 1 were prepared with an acyl-chain fatty acid. In particular, N-palmitoylated peptides were synthesized by standard fmoc solid phase synthetic methods with C-terminal amides as previously described (see Covic, et al. (2002) Pepducin-based intervention of thrombin-receptor signaling and systemic platelet activation. Nat. Med. 8:1161-1165).

Palmitic acid was dissolved in 50% N-methyl pyrolidone/50% methylene chloride and coupled overnight to the deprotected N-terminal amine of the peptide. After cleavage from the resin, palmitoylated peptides were purified to >95% purity by C18, C5 or C4 reverse phase chromatography.

Table 2 provides the antagonist activity for the resulting palmitoylated peptides (SEQ ID NO: 1-11, 13-41, and 70) of Table 1. Table 2 also provides the antagonist activity for the resulting myristoylated peptide SEQ ID NO: 12 of Table 1. Antagonist activity of the peptides were measured using calcium flux assays with SW620 human colon adenocarcinoma cells that endogenously express PAR2. The calcium signal of 100 μM SLIGRL (SEQ ID NO: 73) following 1 min pretreatment with 3 μM or 10 μM of palmitoylated peptides. Final concentration of DMSO vehicle was 0.2%. Antagonist activity of 3 μM and 10 μM peptides against 8 μM SLIGRL (SEQ ID NO: 73; a known PAR2 agonist) was measured by maximal calcium flux. Experiments were repeated at least 2-3 times each and gave similar results.

TABLE 2

| SEQ ID NO | 3 uM peptide Max (% Inh) | ± | SD | 10 uM peptide Max (% Inh) | ± | SD | Expected Mass Da | Actual Mass Da |
|---|---|---|---|---|---|---|---|---|
| 1 | 33 | ± | 22 | 85 | ± | 8 | 1890.8 | 1891.4 |
| 2 | 23 | ± | 2 | 78 | ± | 7 | 1876.8 | 1877.4 |
| 3 | 49 | ± | 23 | 89 | ± | 0 | 1794.8 | 1792.4 |
| 4 | 24 | ± | 8 | 82 | ± | 7 | 2284.3 | 2284.3 |
| 5 | 18 | ± | 0 | 32 | ± | 22 | 2059.1 | 2057.6 |
| 6 | 11 | ± | 16 | 5 | ± | 5 | 2068.1 | 2067.8 |
| 7 | 50 | ± | 3 | 84 | ± | 5 | 2068.1 | 2068.4 |
| 8 | 16 | ± | 5 | 18 | ± | 0 | 1897.9 | 1899.0 |
| 9 | 75 | ± | 29 | 95 | ± | 0 | 2167.3 | 2167.6 |
| 10 | 38 | ± | 1 | 75 | ± | 2 | 2040.1 | 2042.1 |
| 11 | 31 | ± | 8 | 95 | ± | 4 | 2094.2 | 2095.4 |
| 12 | 53 | ± | 43 | 98 | ± | 0 | 2295.4 | 2296.3 |
| 13 | 44 | ± | 9 | 52 | ± | 6 | 2272.4 | 2273.0 |
| 14 | 8 | ± | 14 | 26 | ± | 11 | 2215.3 | 2215.8 |
| 15 | 17 | ± | 0 | 88 | ± | 3 | 2054.1 | 2055.4 |
| 16 | 17 | ± | 2 | 60 | ± | 7 | 1952.4 | 1953.4 |
| 17 | 10 | ± | 29 | 66 | ± | 29 | 2096.2 | 2097.4 |
| 18 | 6 | ± | 1 | 78 | ± | 17 | 2167.2 | 2168.4 |
| 19 | 8 | ± | 6 | 85 | ± | 12 | 2173.3 | 2173.4 |
| 20 | 17 | ± | 5 | 86 | ± | 18 | 2187.3 | 2187.6 |
| 21 | 44 | ± | 2 | 71 | ± | 23 | 2110.1 | 2111.4 |
| 22 | 11 | ± | 3 | 80 | ± | 12 | 2153.2 | 2153.6 |
| 23 | 14 | ± | 0 | 89 | ± | 6 | 2224.3 | 2225.4 |
| 24 | 0 | ± | 12 | 72 | ± | 14 | 2096.2 | 2097.4 |
| 25 | 23 | ± | 9 | 29 | ± | 8 | 2093.2 | 2094.2 |
| 26 | −2 | ± | 1 | 8 | ± | 2 | 2087.2 | 2087.6 |
| 27 | 0 | ± | 4 | 6 | ± | 4 | 2055.1 | 2055.6 |
| 28 | −1 | ± | 4 | −3 | ± | 10 | 2071.6 | 2072.2 |
| 29 | 4 | ± | 15 | 93 | ± | 1 | 2167.3 | 2167.6 |
| 30 | 6 | ± | 13 | 0 | ± | 3 | 2136.2 | 2136.6 |
| 31 | 38 | ± | 8 | 65 | ± | 20 | 1916.9 | — |
| 32 | — | | — | 93 | ± | 7 | 2061.1 | — |
| 33 | 23 | ± | 7 | 93 | ± | 7 | 2061.1 | — |
| 34 | 23 | ± | 7 | 93 | ± | 7 | 1868.7 | — |
| 35 | 23 | ± | 7 | 65 | ± | 20 | 1896.9 | — |
| 36 | 65 | ± | 20 | 65 | ± | 20 | 1980.0 | — |
| 37 | 0 | ± | 0 | 65 | ± | 20 | 2093.1 | — |
| 38 | 23 | ± | 7 | 65 | ± | 20 | 1866.8 | — |
| 39 | 23 | ± | 7 | 93 | ± | 7 | 1967.9 | — |
| 40 | 38 | ± | 8 | 93 | ± | 7 | 1924.9 | — |
| 41 | 38 | ± | 8 | 65 | ± | 20 | 1916.9 | — |
| 70 | 30 | | | 85 | | | 2302.7 | 2302.2 |

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material.

What is claimed is:

1. A method of treating a disorder comprising administering a peptide to a subject in need thereof; wherein the peptide comprises the sequence of:

(SEQ ID NO: 42)
$X_4X_5X_6X_7X_8X_9X_{10}X_{11}X_{12}X_{13}X_{14}X_{15}X_{16}X_{17}X_{18}X_{19}X_{20}$, wherein:
$X_4$ is absent, A, G, P, eK, or aminohexanoic acid (AhX);
$X_5$ is M, G, P, I, L, V, norleucine (J), methionine sulfoxide (M(SO)), methionine sulfone (M(SO$_2$)), or absent when $X_4$ is absent;
$X_6$ is D, E, H, or absent when $X_4$ to $X_5$ are absent;
$X_7$ is D, E, H, or absent when $X_4$ to $X_6$ are absent;
$X_8$ is N, D, or E;
$X_9$ is any amino acid;
$X_{10}$ is any amino acid;
$X_{11}$ is any amino acid or D-amino acid thereof;
$X_{12}$ is K, R, P, or absent;
$X_{13}$ is any amino acid;
$X_{14}$ is K or any amino acid that makes the peptide bond between $X_{13}$ and $X_{14}$ uncleavable by a protease, D, E, A, S, V, L, I, P, F, W, M, G, T, C, Y, N, or Q;
$X_{15}$ is Q, N, H, S, T, Y, C, M, W, or beta-A;
$X_{16}$ is A, S, T, G, Q, beta-A, 2-aminoisobutyric acid (B), or absent;
$X_{17}$ is I, A, L, or V;
$X_{18}$ is K, I, or F; and
$X_{19}$ is a hydrophobic amino acid or a D-amino acid thereof; and
$X_{20}$ is a hydrophobic amino acid, a D-amino acid thereof, any amino acid that makes the peptide bond between $X_{19}$ and $X_{20}$ uncleavable by a protease, or absent; and wherein the disorder is obesity, non-alcoholic steatohepatitis (NASH), alcoholic steatohepatitis, liver fibrosis, or pancreatitis.

2. The method of claim 1, wherein the peptide further comprises $X_3$ at the N-terminus, wherein $X_3$ is S, G, P, eK, aminohexanoic acid (Ahx), W, N, an amino acid with a methyl-amino group at the peptide bond, 1-aminocyclopropanecarboxylic acid (ACC), para-aminobenzoic acid (Paba), or an alpha-substituted tyrosine analog.

3. The method of claim 1, wherein $X_6$ is D, E, or H.
4. The method of claim 1, wherein $X_7$ is E or H.
5. The method of claim 1, wherein $X_8$ is N or D.
6. The method of claim 1, wherein $X_9$ is S or H.
7. The method of claim 1, wherein $X_{10}$ is E.
8. The method of claim 1, wherein $X_{11}$ is K, 2-aminoisobutyric acid (B), hydroxyproline (Hyp), P, dP, G, W, or N.
9. The method of claim 1, wherein $X_{14}$ is a D-amino acid, an amino acid with an N-methyl at the peptide bond, K, A, S, V, L, I, P, F, W, M, G, T, C, Y, N, Q, D, or E.
10. The method of claim 1, wherein $X_4$ is selected from the group consisting of eK, aminohexanoic acid (Ahx), P, and G.
11. The method of claim 1, wherein $X_{20}$ is G, P, A, I, L, V, F, or a D-amino acid thereof.
12. The method of claim 1, wherein $X_{20}$ is a D-amino acid of a hydrophobic amino acid.
13. The method of claim 1, wherein $X_5$ is M, G, P, I, L, V, norleucine (J), M(SO), or M(SO$_2$).
14. The method of claim 1, wherein $X_{15}$ is S or Q.
15. The method of claim 1, wherein the peptide comprises a hydrophobic moiety.
16. The method of claim 1, wherein the peptide is 13-30 amino acids in length.
17. The method of claim 1, wherein the disorder is non-alcoholic steatohepatitis (NASH).
18. The method of claim 1, wherein the liver fibrosis is cirrhosis.
19. The method of claim 1, wherein $X_{11}$ is 2-aminoisobutyric acid (B), hydroxyproline (Hyp), P, a proline homolog, G, W, N, an amino acid with a methyl-amino group at the peptide bond, 1-aminocyclopropanecarboxylic acid (ACC), para-aminobenzoic acid (Paba), or an alpha-substituted tyrosine analog.
20. The method of claim 1, wherein $X_{13}$ is citrulline (Cit).
21. The method of claim 15, wherein the hydrophobic moiety comprises a lipid moiety, acyl moiety, steroid moiety, or amino acid moiety.
22. The method of claim 21, wherein the lipid moiety is selected from the group consisting of: capryloyl ($C_8$); nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phytanoyl (methyl substituted $C_{16}$); heptadecanoyl ($C_{17}$); stearoyl ($C_{18}$); nonadecanoyl ($C_{19}$); arachidoyl ($C_{20}$); heneicosanoyl ($C_{21}$); behenoyl ($C_{22}$); trucisanoyl ($C_{23}$); and lignoceroyl ($C_{24}$).
23. The method of claim 21, wherein the lipid moiety is myristoyl ($C_{14}$) or palmitoyl ($C_{16}$).
24. The method of claim 1, wherein the peptide comprises the sequence of SEQ ID NO: 9.
25. The method of claim 1, wherein the peptide comprises the sequence of SEQ ID NO: 13.
26. The method of claim 1, wherein the disorder is liver fibrosis.
27. The method of claim 1, wherein the disorder is diabetes.
28. The method of claim 1, wherein the disorder is obesity.
29. The method of claim 1, wherein the disorder is pancreatitis.
30. The method of claim 1, wherein the disorder is alcoholic steatohepatitis.
31. The method of claim 1, wherein $X_{12}$ is K or P.
32. The method of claim 1, wherein $X_{16}$ is A, 2-aminoisobutyric acid (B), Q, or absent.
33. The method of claim 1, wherein $X1_{17}$ is I or A.
34. The method of claim 1, wherein $X_{18}$ is K or I.
35. The method of claim 1, wherein $X_{19}$ is G, P, I, L, V, F, K, or a D-amino acid thereof.

* * * * *

SEQUENCE LISTING

<160> NUMBER OF SEQ ID NOS: 80

<210> SEQ ID NO 1
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1

Gly His Glu Asn Ser Glu Lys Lys Arg Lys Gln Ala Ile Lys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 2

Gly Asp His Asn Ser Glu Lys Lys Arg Lys Gln Ala Ile Lys
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 3

Asp Ser Glu Lys Lys Arg Lys Gln Ala Ile Lys Leu Ile
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 4

Arg Ser Ser Ala Ile Asp Glu Asn Ser Glu Lys Lys Arg Lys Ser Ala
1               5                   10                  15

Ile Lys

<210> SEQ ID NO 5
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 5

Ala Ile Asp Glu Asn Ser Glu Lys Lys Phe Lys Ser Ala Ile Lys Leu
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 6

Ala Ile His His Asp Ser Glu Pro Lys Arg Lys Ser Ala Ile Lys Leu
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (8)..(8)
<223> OTHER INFORMATION: Pro is D-Proline

<400> SEQUENCE: 7

Ala Ile His His Asp Ser Glu Pro Lys Arg Lys Ser Ala Ile Lys Leu
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (8)..(8)
<223> OTHER INFORMATION: Pro is D-Proline

<400> SEQUENCE: 8

Ala Ile His His Asp Ser Glu Pro Arg Lys Ser Ala Ala Lys Leu
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (17)..(17)
<223> OTHER INFORMATION: Ile is D-Isoleucine

<400> SEQUENCE: 9

Gly Leu His His Asp Ser Glu Pro Lys Arg Lys Ser Ala Ile Lys Leu
1               5                   10                  15

Ile

<210> SEQ ID NO 10
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (11)..(11)
<223> OTHER INFORMATION: Lys is D-Lysine
<220> FEATURE:
<221> NAME/KEY: MOD_RES
<222> LOCATION: (16)..(16)
<223> OTHER INFORMATION: Val is D-Valine

<400> SEQUENCE: 10

Gly Leu His His Asp Ser Glu Pro Lys Arg Lys Ser Ala Ile Lys Val
1               5                   10                  15

<210> SEQ ID NO 11

```
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (11)..(11)
<223> OTHER INFORMATION: Lys is D-Lysine
<220> FEATURE:
<221> NAME/KEY: MOD_RES
<222> LOCATION: (16)..(16)
<223> OTHER INFORMATION: Leu is D-Leucine

<400> SEQUENCE: 11

Pro Leu His His Asp Ser Glu Pro Lys Arg Lys Ser Ala Ile Lys Leu
1               5                   10                  15

<210> SEQ ID NO 12
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Lys is epsilon Lysine
<220> FEATURE:
<221> NAME/KEY: MOD_RES
<222> LOCATION: (12)..(12)
<223> OTHER INFORMATION: Lys is D-Lysine
<220> FEATURE:
<221> NAME/KEY: MOD_RES
<222> LOCATION: (18)..(18)
<223> OTHER INFORMATION: Ile is D-Isoleucine

<400> SEQUENCE: 12

Lys Gly Leu His His Asp Ser Glu Pro Lys Arg Lys Ser Ala Ile Lys
1               5                   10                  15

Leu Ile

<210> SEQ ID NO 13
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Lys is epsilon Lysine
<220> FEATURE:
<221> NAME/KEY: MOD_RES
<222> LOCATION: (12)..(12)
<223> OTHER INFORMATION: Lys is D-Lysine
<220> FEATURE:
<221> NAME/KEY: MOD_RES
<222> LOCATION: (18)..(18)
<223> OTHER INFORMATION: Val is D-Valine

<400> SEQUENCE: 13

Lys Gly Leu Asp Glu Asn Ser Glu Lys Lys Phe Lys Ser Ala Ile Lys
1               5                   10                  15

Leu Val

<210> SEQ ID NO 14
<211> LENGTH: 17
<212> TYPE: PRT
<213> ORGANISM: Artificial Sequence
<220> FEATURE:
```

```
<223> OTHER INFORMATION: Synthetic Polypeptide
<220> FEATURE:
<221> NAME/KEY: MOD_RES
<222> LOCATION: (1)..(1)
<223> OTHER INFORMATION: Lys is epsilon Lysine
<220> FEATURE:
<221> NAME/KEY: MOD_RES
<222> LOCATION: (11)..(11)
<223> OTHER INFORMATION: Lys is D-Lysine
<220> FEATURE:
<221> NAME/KEY: MOD_RES
<222> LOCATION: (17)..(17)
<223> OTHER INFORMATION: Val is D-Valine

<400> SEQUENCE: 14

Lys Leu Asp Glu Asn Ser Glu Lys Lys Phe Lys Ser Ala Ile Lys Leu
1               5                   10                  15
Val

<210> SEQ ID NO 15
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (11)..(11)
<223> OTHER INFORMATION: Lys is D-Lysine
<220> FEATURE:
<221> NAME/KEY: MOD_RES
<222> LOCATION: (13)..(13)
<223> OTHER INFORMATION: Xaa is Aib
<220> FEATURE:
<221> NAME/KEY: MOD_RES
<222> LOCATION: (16)..(16)
<223> OTHER INFORMATION: Val is D-Valine

<400> SEQUENCE: 15

Gly Leu His His Asp Ser Glu Pro Lys Arg Lys Ser Xaa Ile Lys Val
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (11)..(11)
<223> OTHER INFORMATION: Lys is D-Lysine
<220> FEATURE:
<221> NAME/KEY: MOD_RES
<222> LOCATION: (12)..(12)
<223> OTHER INFORMATION: Ala is bAla
<220> FEATURE:
<221> NAME/KEY: MOD_RES
<222> LOCATION: (15)..(15)
<223> OTHER INFORMATION: Val is D-Valine

<400> SEQUENCE: 16

Gly Leu His His Asp Ser Glu Pro Lys Arg Lys Ala Ile Lys Val
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
```

```
<221> NAME/KEY: MISC_FEATURE
<222> LOCATION: (1)..(1)
<223> OTHER INFORMATION: Xaa is aminohexanoic acid
<220> FEATURE:
<221> NAME/KEY: MOD_RES
<222> LOCATION: (11)..(11)
<223> OTHER INFORMATION: Lys is D-Lysine
<220> FEATURE:
<221> NAME/KEY: MOD_RES
<222> LOCATION: (16)..(16)
<223> OTHER INFORMATION: Val is D-Valine

<400> SEQUENCE: 17

Xaa Leu His His Asp Ser Glu Pro Lys Arg Lys Ser Ala Ile Lys Val
1               5                   10                  15

<210> SEQ ID NO 18
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (11)..(11)
<223> OTHER INFORMATION: Lys is D-Lysine
<220> FEATURE:
<221> NAME/KEY: MOD_RES
<222> LOCATION: (13)..(13)
<223> OTHER INFORMATION: Xaa is Aib
<220> FEATURE:
<221> NAME/KEY: MOD_RES
<222> LOCATION: (17)..(17)
<223> OTHER INFORMATION: Val is D-Valine

<400> SEQUENCE: 18

Gly Leu His His Asp Ser Glu Pro Lys Arg Lys Ser Xaa Ile Lys Leu
1               5                   10                  15

Val

<210> SEQ ID NO 19
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Lys is epsilon Lysine
<220> FEATURE:
<221> NAME/KEY: MOD_RES
<222> LOCATION: (12)..(12)
<223> OTHER INFORMATION: Lys is D-Lysine

<400> SEQUENCE: 19

Lys Gly Leu Asp Glu Asn Ser Glu Lys Lys Phe Lys Ser Ala Ile Lys
1               5                   10                  15

Leu

<210> SEQ ID NO 20
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Lys is epsilon Lysine
```

<400> SEQUENCE: 20

Lys Ala Ile Asp Glu Asn Ser Glu Lys Lys Phe Lys Ser Ala Ile Lys
1               5                   10                  15

Leu

<210> SEQ ID NO 21
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is aminohexanoic acid
<220> FEATURE:
<221> NAME/KEY: MOD_RES
<222> LOCATION: (11)..(11)
<223> OTHER INFORMATION: Lys is D-Lysine
<220> FEATURE:
<221> NAME/KEY: MOD_RES
<222> LOCATION: (13)..(13)
<223> OTHER INFORMATION: Xaa is Aib
<220> FEATURE:
<221> NAME/KEY: MOD_RES
<222> LOCATION: (16)..(16)
<223> OTHER INFORMATION: Val is D-Valine

<400> SEQUENCE: 21

Xaa Leu His His Asp Ser Glu Pro Lys Arg Lys Ser Xaa Ile Lys Val
1               5                   10                  15

<210> SEQ ID NO 22
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (17)..(17)
<223> OTHER INFORMATION: Val is D-Valine

<400> SEQUENCE: 22

Gly Leu His His Asp Ser Glu Pro Lys Arg Lys Ser Ala Ile Lys Leu
1               5                   10                  15

Val

<210> SEQ ID NO 23
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: Lys is epsilon Lysine
<220> FEATURE:
<221> NAME/KEY: MOD_RES
<222> LOCATION: (17)..(17)
<223> OTHER INFORMATION: Val is D-Valine

<400> SEQUENCE: 23

Lys Leu His His Asp Ser Glu Pro Lys Arg Lys Ser Ala Ile Lys Leu
1               5                   10                  15

Val

```
<210> SEQ ID NO 24
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (16)..(16)
<223> OTHER INFORMATION: Val is D-Valine

<400> SEQUENCE: 24

Leu His His Asp Ser Glu Pro Lys Arg Lys Ser Ala Ile Lys Leu Val
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 25

Ala Met Asp Glu Asn Ser Glu Lys Lys Tyr Lys Ser Ala Ile Lys Leu
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (10)..(10)
<223> OTHER INFORMATION: Xaa is citrulline

<400> SEQUENCE: 26

Ala Met Asp Glu Asn Ser Glu Lys Lys Xaa Lys Ser Ala Ile Lys Leu
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 27

Ala Met Asp Glu Asn Ser Glu Pro Lys Arg Lys Ser Ala Ile Lys Leu
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (8)..(8)
<223> OTHER INFORMATION: Pro is hydroxyproline

<400> SEQUENCE: 28

Ala Met Asp Glu Asn Ser Glu Pro Lys Arg Lys Ser Ala Ile Lys Leu
1               5                   10                  15

<210> SEQ ID NO 29
<211> LENGTH: 17
```

```
<212> TYPE: PRT
<213> ORGANISM: Artificial Sequence
<220> FEATURE:
<223> OTHER INFORMATION: Synthetic Polypeptide

<400> SEQUENCE: 29

Gly Leu His His Asp Ser Glu Pro Lys Arg Lys Ser Ala Ile Lys Leu
1               5                   10                  15

Ile

<210> SEQ ID NO 30
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 30

Gly Leu Asp Glu Asn Ser Glu Pro Lys Arg Lys Ser Ala Ile Lys Leu
1               5                   10                  15

Ile

<210> SEQ ID NO 31
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 31

Gly Asp Glu Asn His Glu Lys Lys Arg Lys Gln Ala Ile Lys
1               5                   10

<210> SEQ ID NO 32
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 32

Pro Gly Asp Glu Asn Ser Glu Lys Pro Lys Arg Lys Gln Ala Ile Lys
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 33

Gly Pro Asp Glu Asn Ser Glu Lys Lys Pro Arg Lys Gln Ala Ile Lys
1               5                   10                  15

<210> SEQ ID NO 34
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (9)..(9)
<223> OTHER INFORMATION: Xaa is citrulline

<400> SEQUENCE: 34
```

```
Gly Asp Glu Asn Ser Glu Lys Lys Xaa Lys Gln Ala Ile Lys
1               5                   10
```

<210> SEQ ID NO 35
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (15)..(15)
<223> OTHER INFORMATION: Ala is D-Alanine

<400> SEQUENCE: 35

```
Gly Asp Glu Asn Ser Glu Lys Lys Arg Lys Ser Ala Ile Lys Ala
1               5                   10                  15
```

<210> SEQ ID NO 36
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 36

```
Gly Asp Glu Asn Ser Glu Lys Lys Arg Lys Gln Ala Ile Lys Leu
1               5                   10                  15
```

<210> SEQ ID NO 37
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 37

```
Gly Asp Glu Asn Ser Glu Lys Lys Arg Lys Gln Ala Ile Lys Leu Ile
1               5                   10                  15
```

<210> SEQ ID NO 38
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 38

```
Gly Asp Glu Asn Ser Glu Lys Lys Arg Lys Gln Ala Ile Lys
1               5                   10
```

<210> SEQ ID NO 39
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 39

```
Gly Asp Glu Asn Ser Glu Lys Arg Trp Leu Trp Ala Ile Lys
1               5                   10
```

<210> SEQ ID NO 40
<211> LENGTH: 14
<212> TYPE: PRT
<213> ORGANISM: Artificial Sequence
<220> FEATURE:

```
<223> OTHER INFORMATION: Synthetic Polypeptide

<400> SEQUENCE: 40

Gly Asp Glu Asn Ser Glu Lys Lys Arg Lys Trp Ala Ile Lys
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 41

Met Asp Glu Asn Ser Glu Lys Lys Arg Lys Arg Ala Ile Lys
1               5                   10

<210> SEQ ID NO 42
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is absent, A, G, P, or an N-terminal linker
<220> FEATURE:
<221> NAME/KEY: MISC_FEATURE
<222> LOCATION: (2)..(2)
<223> OTHER INFORMATION: Xaa is M, G, P, I, L, V, Nle, methionine
      sulfoxide (M(SO)), or methionine sulfone (M(SO2)), or absent when
      X1 is absent
<220> FEATURE:
<221> NAME/KEY: MISC_FEATURE
<222> LOCATION: (3)..(3)
<223> OTHER INFORMATION: Xaa is D, E, H, or absent when X1 to X2 are
      absent
<220> FEATURE:
<221> NAME/KEY: MISC_FEATURE
<222> LOCATION: (4)..(4)
<223> OTHER INFORMATION: Xaa is D, E, H, or absent when X1 to X3 are
      absent
<220> FEATURE:
<221> NAME/KEY: MISC_FEATURE
<222> LOCATION: (5)..(5)
<223> OTHER INFORMATION: Xaa is N, D, or E
<220> FEATURE:
<221> NAME/KEY: MISC_FEATURE
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa is any naturally occurring amino acid,
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (9)..(9)
<223> OTHER INFORMATION: Xaa is K, R, P or absent
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
```

```
<223> OTHER INFORMATION: Xaa is any naturally occurring amino acid or or
      bAla
<220> FEATURE:
<221> NAME/KEY: MISC_FEATURE
<222> LOCATION: (13)..(13)
<223> OTHER INFORMATION: Xaa is A, S, T, G, Q, bAla, Aib, or absent
<220> FEATURE:
<221> NAME/KEY: MISC_FEATURE
<222> LOCATION: (14)..(14)
<223> OTHER INFORMATION: Xaa is I, A, L, or V
<220> FEATURE:
<221> NAME/KEY: MISC_FEATURE
<222> LOCATION: (15)..(15)
<223> OTHER INFORMATION: Xaa is K, I, or F
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or absent
<220> FEATURE:
<221> NAME/KEY: MISC_FEATURE
<222> LOCATION: (17)..(17)
<223> OTHER INFORMATION: Xaa is a hydrophobic amino acid, a D-amino acid
      thereof, any amino acid that makes the peptide bond between X16
      and X17 uncleavable by a protease, or absent

<400> SEQUENCE: 42

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 43
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is absent, A, G, P, or an N-terminal linker
<220> FEATURE:
<221> NAME/KEY: MISC_FEATURE
<222> LOCATION: (2)..(2)
<223> OTHER INFORMATION: Xaa is M, G, P, I, L, V, Nle, methionine
      sulfoxide (M(SO)), or methionine sulfone (M(SO2)), or absent when
      X1 is absent
<220> FEATURE:
<221> NAME/KEY: MISC_FEATURE
<222> LOCATION: (3)..(3)
<223> OTHER INFORMATION: Xaa is D, E, H, or absent when X1 to X2 are
      absent
<220> FEATURE:
<221> NAME/KEY: MISC_FEATURE
<222> LOCATION: (4)..(4)
<223> OTHER INFORMATION: Xaa is D, E, H, or absent when X1 to X3 are
      absent
<220> FEATURE:
<221> NAME/KEY: MISC_FEATURE
<222> LOCATION: (5)..(5)
<223> OTHER INFORMATION: Xaa is N, D, or E
<220> FEATURE:
<221> NAME/KEY: MISC_FEATURE
<222> LOCATION: (8)..(8)
<223> OTHER INFORMATION: Xaa is any naturally occurring amino acid, or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (9)..(9)
<223> OTHER INFORMATION: Xaa is K, R, P or absent
<220> FEATURE:
<221> NAME/KEY: MISC_FEATURE
<222> LOCATION: (10)..(10)
<223> OTHER INFORMATION: Xaa is any naturally occurring amino acid or
      citrulline
```

```
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (13)..(13)
<223> OTHER INFORMATION: Xaa is A, S, T, G, Q, bAla, Aib, or absent
<220> FEATURE:
<221> NAME/KEY: MISC_FEATURE
<222> LOCATION: (14)..(14)
<223> OTHER INFORMATION: Xaa is I, A, L, or V
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or absent

<400> SEQUENCE: 43

Xaa Xaa Xaa Xaa Xaa Ser Glu Xaa Xaa Xaa Xaa Xaa Xaa Xaa Lys Xaa
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is H, D, E, or absent when X1 to X2 are
      absent
<220> FEATURE:
<221> NAME/KEY: MISC_FEATURE
<222> LOCATION: (4)..(4)
<223> OTHER INFORMATION: Xaa is H, D, E, or absent when X1 to X3 are
      absent
<220> FEATURE:
<221> NAME/KEY: MISC_FEATURE
<222> LOCATION: (5)..(5)
<223> OTHER INFORMATION: Xaa is D, E, or N
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (13)..(13)
<223> OTHER INFORMATION: Xaa is A, S, T, G, Q, N, bAla, Aib, or absent
<220> FEATURE:
<221> NAME/KEY: MISC_FEATURE
```

<222> LOCATION: (14)..(14)
<223> OTHER INFORMATION: Xaa is I, A, L, or V
<220> FEATURE:
<221> NAME/KEY: MISC_FEATURE
<222> LOCATION: (15)..(15)
<223> OTHER INFORMATION: Xaa is K, I, or F
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 44

Ala Ile Xaa Xaa Xaa Ser Glu Xaa Lys Xaa Xaa Xaa Xaa Xaa Xaa Xaa
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is H, D, E, or absent when X1 to X2 are
      absent
<220> FEATURE:
<221> NAME/KEY: MISC_FEATURE
<222> LOCATION: (4)..(4)
<223> OTHER INFORMATION: Xaa is H, D, E, or absent when X1 to X3 are
      absent
<220> FEATURE:
<221> NAME/KEY: MISC_FEATURE
<222> LOCATION: (5)..(5)
<223> OTHER INFORMATION: Xaa is D, E, or N
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (13)..(13)
<223> OTHER INFORMATION: Xaa is A, S, T, G, Q, N, bAla, Aib, or absent
<220> FEATURE:
<221> NAME/KEY: MISC_FEATURE
<222> LOCATION: (14)..(14)
<223> OTHER INFORMATION: Xaa is I, A, L, or V
<220> FEATURE:
<221> NAME/KEY: MISC_FEATURE
<222> LOCATION: (15)..(15)
<223> OTHER INFORMATION: Xaa is K, I, or F
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 45

Ala Met Xaa Xaa Xaa Ser Glu Xaa Lys Xaa Xaa Xaa Xaa Xaa Xaa
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is H, D, E, or absent when X1 to X2 are
      absent
<220> FEATURE:
<221> NAME/KEY: MISC_FEATURE
<222> LOCATION: (4)..(4)
<223> OTHER INFORMATION: Xaa is H, D, E, or absent when X1 to X3 are
      absent
<220> FEATURE:
<221> NAME/KEY: MISC_FEATURE
<222> LOCATION: (5)..(5)
<223> OTHER INFORMATION: Xaa is D, E, or N
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (13)..(13)
<223> OTHER INFORMATION: Xaa is A, S, T, G, Q, N, bAla, Aib, or absent
<220> FEATURE:
<221> NAME/KEY: MISC_FEATURE
<222> LOCATION: (14)..(14)
<223> OTHER INFORMATION: Xaa is I, A, L, or V
<220> FEATURE:
<221> NAME/KEY: MISC_FEATURE
<222> LOCATION: (15)..(15)
<223> OTHER INFORMATION: Xaa is K, I, or F
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 46

Gly Leu Xaa Xaa Xaa Ser Glu Xaa Lys Xaa Xaa Xaa Xaa Xaa Xaa
1               5                   10                  15

<210> SEQ ID NO 47
<211> LENGTH: 15
<212> TYPE: PRT
<213> ORGANISM: Artificial Sequence
<220> FEATURE:

```
-continued

<223> OTHER INFORMATION: Synthetic Polypeptide
<220> FEATURE:
<221> NAME/KEY: MISC_FEATURE
<222> LOCATION: (7)..(7)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (9)..(9)
<223> OTHER INFORMATION: Xaa is any naturally occurring amino acid or
      citrulline
<220> FEATURE:
<221> NAME/KEY: MISC_FEATURE
<222> LOCATION: (10)..(10)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (11)..(11)
<223> OTHER INFORMATION: Xaa is any naturally occurring amino acid or
      bAla
<220> FEATURE:
<221> NAME/KEY: MISC_FEATURE
<222> LOCATION: (12)..(12)
<223> OTHER INFORMATION: Xaa is A, S, T, G, Q, N, bAla, Aib, or absent
<220> FEATURE:
<221> NAME/KEY: MISC_FEATURE
<222> LOCATION: (13)..(13)
<223> OTHER INFORMATION: Xaa is I, A, L, or V
<220> FEATURE:
<221> NAME/KEY: MISC_FEATURE
<222> LOCATION: (14)..(14)
<223> OTHER INFORMATION: Xaa is K, I, or F
<220> FEATURE:
<221> NAME/KEY: MISC_FEATURE
<222> LOCATION: (15)..(15)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 47

Gly Asp Glu Asn Ser Glu Xaa Lys Xaa Xaa Xaa Xaa Xaa Xaa Xaa
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (9)..(9)
<223> OTHER INFORMATION: Xaa is any naturally occurring amino acid or
      citrulline
<220> FEATURE:
<221> NAME/KEY: MISC_FEATURE
<222> LOCATION: (10)..(10)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (11)..(11)
<223> OTHER INFORMATION: Xaa is any naturally occurring amino acid or
```

```
            bAla
<220> FEATURE:
<221> NAME/KEY: MISC_FEATURE
<222> LOCATION: (12)..(12)
<223> OTHER INFORMATION: Xaa is A, S, T, G, Q, N, bAla, Aib, or absent
<220> FEATURE:
<221> NAME/KEY: MISC_FEATURE
<222> LOCATION: (13)..(13)
<223> OTHER INFORMATION: Xaa is I, A, L, or V
<220> FEATURE:
<221> NAME/KEY: MISC_FEATURE
<222> LOCATION: (14)..(14)
<223> OTHER INFORMATION: Xaa is K, I, or F
<220> FEATURE:
<221> NAME/KEY: MISC_FEATURE
<222> LOCATION: (15)..(15)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 48

Gly Asp Glu Asn Xaa Glu Xaa Lys Xaa Xaa Xaa Xaa Xaa Xaa Xaa
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (13)..(13)
<223> OTHER INFORMATION: Xaa is A, S, T, G, Q, N, bAla, Aib, or absent
<220> FEATURE:
<221> NAME/KEY: MISC_FEATURE
<222> LOCATION: (14)..(14)
<223> OTHER INFORMATION: Xaa is I, A, L, or V
<220> FEATURE:
<221> NAME/KEY: MISC_FEATURE
<222> LOCATION: (15)..(15)
<223> OTHER INFORMATION: Xaa is K, I, or F
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 49
```

```
Gly Leu His His Asp Xaa Glu Xaa Lys Xaa Xaa Xaa Xaa Xaa Xaa Xaa
1               5                   10                  15
```

<210> SEQ ID NO 50
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (13)..(13)
<223> OTHER INFORMATION: Xaa is A, S, T, G, Q, N, bAla, Aib, or absent
<220> FEATURE:
<221> NAME/KEY: MISC_FEATURE
<222> LOCATION: (14)..(14)
<223> OTHER INFORMATION: Xaa is I, A, L, or V
<220> FEATURE:
<221> NAME/KEY: MISC_FEATURE
<222> LOCATION: (15)..(15)
<223> OTHER INFORMATION: Xaa is K, I, or F
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 50

```
Gly Leu Asp Glu Asn Xaa Glu Xaa Lys Xaa Xaa Xaa Xaa Xaa Xaa Xaa
1               5                   10                  15
```

<210> SEQ ID NO 51
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is H, D, E, or absent when X1 to X2 are
      absent
<220> FEATURE:
<221> NAME/KEY: MISC_FEATURE
<222> LOCATION: (4)..(4)
<223> OTHER INFORMATION: Xaa is H, D, E, or absent when X1 to X3 are
      absent
<220> FEATURE:
<221> NAME/KEY: MISC_FEATURE

```
<222> LOCATION: (5)..(5)
<223> OTHER INFORMATION: Xaa is D, E, or N
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 51

Gly Leu Xaa Xaa Xaa Xaa Glu Xaa Lys Xaa Xaa Xaa Ala Ile Lys Xaa
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent
```

<400> SEQUENCE: 52

Gly Leu His His Asp Xaa Glu Xaa Lys Xaa Xaa Xaa Ala Ile Lys Xaa
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 53

Gly Leu Asp Glu Asn Xaa Glu Xaa Lys Xaa Xaa Xaa Ala Ile Lys Xaa
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or

```
                              bAla
<220> FEATURE:
<221> NAME/KEY: MISC_FEATURE
<222> LOCATION: (13)..(13)
<223> OTHER INFORMATION: Xaa is A, S, T, G, Q, N, bAla, Aib, or absent
<220> FEATURE:
<221> NAME/KEY: MISC_FEATURE
<222> LOCATION: (14)..(14)
<223> OTHER INFORMATION: Xaa is I, A, L, or V
<220> FEATURE:
<221> NAME/KEY: MISC_FEATURE
<222> LOCATION: (15)..(15)
<223> OTHER INFORMATION: Xaa is K, I, or F
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 54

Gly Leu His His Asp Ser Glu Xaa Lys Xaa Xaa Xaa Xaa Xaa Xaa
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (13)..(13)
<223> OTHER INFORMATION: Xaa is A, S, T, G, Q, N, bAla, Aib, or absent
<220> FEATURE:
<221> NAME/KEY: MISC_FEATURE
<222> LOCATION: (14)..(14)
<223> OTHER INFORMATION: Xaa is I, A, L, or V
<220> FEATURE:
<221> NAME/KEY: MISC_FEATURE
<222> LOCATION: (15)..(15)
<223> OTHER INFORMATION: Xaa is K, I, or F
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 55

Gly Leu Asp Glu Asn Ser Glu Xaa Lys Xaa Xaa Xaa Xaa Xaa Xaa
1               5                   10                  15
```

```
<210> SEQ ID NO 56
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is H, D, E, or absent when X1 to X2 are
      absent
<220> FEATURE:
<221> NAME/KEY: MISC_FEATURE
<222> LOCATION: (4)..(4)
<223> OTHER INFORMATION: Xaa is H, D, E, or absent when X1 to X3 are
      absent
<220> FEATURE:
<221> NAME/KEY: MISC_FEATURE
<222> LOCATION: (5)..(5)
<223> OTHER INFORMATION: Xaa is D, E, or N
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 56

Gly Leu Xaa Xaa Xaa Ser Glu Xaa Lys Xaa Xaa Xaa Ala Ile Lys Xaa
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
```

```
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 57

Gly Leu His His Asp Ser Glu Xaa Lys Xaa Xaa Xaa Ala Ile Lys Xaa
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 58

Gly Leu Asp Glu Asn Ser Glu Xaa Lys Xaa Xaa Xaa Ala Ile Lys Xaa
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is an N-terminal linker, A, G, P, or absent
<220> FEATURE:
<221> NAME/KEY: MISC_FEATURE
<222> LOCATION: (2)..(2)
<223> OTHER INFORMATION: Xaa is M, G, P, I, L, V, Nle, methionine
      sulfoxide (M(SO)), or methionine sulfone (M(SO2)), or absent
<220> FEATURE:
<221> NAME/KEY: MISC_FEATURE
<222> LOCATION: (6)..(7)
<223> OTHER INFORMATION: Xaa can be any naturally occurring amino acid
<220> FEATURE:
<221> NAME/KEY: MISC_FEATURE
```

```
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (9)..(9)
<223> OTHER INFORMATION: Xaa is K, R, P, or absent
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 59

Xaa Xaa His His Asp Xaa Xaa Xaa Xaa Xaa Xaa Xaa Ala Ile Lys Xaa
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is an N-terminal linker, A, G, P, or absent
<220> FEATURE:
<221> NAME/KEY: MISC_FEATURE
<222> LOCATION: (2)..(2)
<223> OTHER INFORMATION: Xaa is M, G, P, I, L, V, Nle, methionine
      sulfoxide (M(SO)), or methionine sulfone (M(SO2)), or absent
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (13)..(13)
<223> OTHER INFORMATION: Xaa is A, S, T, G, Q, N, bAla, Aib, or absent
<220> FEATURE:
```

```
<221> NAME/KEY: MISC_FEATURE
<222> LOCATION: (14)..(14)
<223> OTHER INFORMATION: Xaa is I, A, L, or V
<220> FEATURE:
<221> NAME/KEY: MISC_FEATURE
<222> LOCATION: (15)..(15)
<223> OTHER INFORMATION: Xaa is K, I, or F
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 60

Xaa Xaa His His Asp Ser Glu Xaa Lys Xaa Xaa Xaa Xaa Xaa Xaa Xaa
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is an N-terminal linker, A, G, P, or absent
<220> FEATURE:
<221> NAME/KEY: MISC_FEATURE
<222> LOCATION: (2)..(2)
<223> OTHER INFORMATION: Xaa is M, G, P, I, L, V, Nle, methionine
      sulfoxide (M(SO)), or methionine sulfone (M(SO2)), or absent
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (9)..(9)
<223> OTHER INFORMATION: Xaa is K, R, P, or absent
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (13)..(13)
<223> OTHER INFORMATION: Xaa is A, S, T, G, Q, N, bAla, Aib, or absent
<220> FEATURE:
<221> NAME/KEY: MISC_FEATURE
<222> LOCATION: (14)..(14)
<223> OTHER INFORMATION: Xaa is I, A, L, or V
<220> FEATURE:
<221> NAME/KEY: MISC_FEATURE
<222> LOCATION: (15)..(15)
<223> OTHER INFORMATION: Xaa is K, I, or F
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent
```

<400> SEQUENCE: 61

Xaa Xaa Asp Glu Asn Ser Glu Xaa Xaa Xaa Xaa Xaa Xaa Xaa Xaa
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is an N-terminal linker, A, G, P, or absent
<220> FEATURE:
<221> NAME/KEY: MISC_FEATURE
<222> LOCATION: (2)..(2)
<223> OTHER INFORMATION: Xaa is M, G, P, I, L, V, Nle, methionine
      sulfoxide (M(SO)), or methionine sulfone (M(SO2)), or absent
<220> FEATURE:
<221> NAME/KEY: MISC_FEATURE
<222> LOCATION: (9)..(9)
<223> OTHER INFORMATION: Xaa is K, R, P, or absent
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (13)..(13)
<223> OTHER INFORMATION: Xaa is A, S, T, G, Q, N, bAla, Aib, or absent
<220> FEATURE:
<221> NAME/KEY: MISC_FEATURE
<222> LOCATION: (14)..(14)
<223> OTHER INFORMATION: Xaa is I, A, L, or V
<220> FEATURE:
<221> NAME/KEY: MISC_FEATURE
<222> LOCATION: (15)..(15)
<223> OTHER INFORMATION: Xaa is K, I, or F
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 62

Xaa Xaa Asp Glu Asn Ser Glu Lys Xaa Xaa Xaa Xaa Xaa Xaa Xaa
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is an N-terminal linker, A, G, P, or absent
<220> FEATURE:
<221> NAME/KEY: MISC_FEATURE

```
<222> LOCATION: (2)..(2)
<223> OTHER INFORMATION: Xaa is M, G, P, I, L, V, Nle, methionine
      sulfoxide (M(SO)), or methionine sulfone (M(SO2)), or absent
<220> FEATURE:
<221> NAME/KEY: MISC_FEATURE
<222> LOCATION: (3)..(3)
<223> OTHER INFORMATION: Xaa is H, D, E, or absent when X1 to X2 are
      absent
<220> FEATURE:
<221> NAME/KEY: MISC_FEATURE
<222> LOCATION: (4)..(4)
<223> OTHER INFORMATION: Xaa is H, D, E, or absent when X1 to X3 are
      absent
<220> FEATURE:
<221> NAME/KEY: MISC_FEATURE
<222> LOCATION: (5)..(5)
<223> OTHER INFORMATION: Xaa is D, E, or N
<220> FEATURE:
<221> NAME/KEY: MISC_FEATURE
<222> LOCATION: (6)..(7)
<223> OTHER INFORMATION: Xaa is any naturally occurring amino acid
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (9)..(9)
<223> OTHER INFORMATION: Xaa is K, R, P, or absent
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 63

Xaa Xaa Xaa Xaa Xaa Xaa Xaa Xaa Xaa Xaa Xaa Xaa Ala Ile Lys Xaa
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is an N-terminal linker, A, G, P, or absent
<220> FEATURE:
<221> NAME/KEY: MISC_FEATURE
<222> LOCATION: (2)..(2)
<223> OTHER INFORMATION: Xaa is M, G, P, I, L, V, Nle, methionine
      sulfoxide (M(SO)), or methionine sulfone (M(SO2)), or absent
<220> FEATURE:
<221> NAME/KEY: MISC_FEATURE
<222> LOCATION: (3)..(3)
<223> OTHER INFORMATION: Xaa is H, D, E, or absent when X1 to X2 are
```

```
            absent
<220> FEATURE:
<221> NAME/KEY: MISC_FEATURE
<222> LOCATION: (4)..(4)
<223> OTHER INFORMATION: Xaa is H, D, E, or absent when X1 to X3 are
      absent
<220> FEATURE:
<221> NAME/KEY: MISC_FEATURE
<222> LOCATION: (5)..(5)
<223> OTHER INFORMATION: Xaa is D, E, or N
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (9)..(9)
<223> OTHER INFORMATION: Xaa is K, R, P, or absent
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 64

Xaa Xaa Xaa Xaa Xaa Ser Glu Xaa Xaa Xaa Xaa Xaa Ala Ile Lys Xaa
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is an N-terminal linker, A, G, P, or absent
<220> FEATURE:
<221> NAME/KEY: MISC_FEATURE
<222> LOCATION: (2)..(2)
<223> OTHER INFORMATION: Xaa is M, G, P, I, L, V, Nle, methionine
      sulfoxide (M(SO)), or methionine sulfone (M(SO2)), or absent
<220> FEATURE:
<221> NAME/KEY: MISC_FEATURE
<222> LOCATION: (3)..(3)
<223> OTHER INFORMATION: Xaa is H, D, E, or absent when X1 to X2 are
      absent
<220> FEATURE:
<221> NAME/KEY: MISC_FEATURE
<222> LOCATION: (4)..(4)
<223> OTHER INFORMATION: Xaa is H, D, E, or absent when X1 to X3 are
      absent
<220> FEATURE:
<221> NAME/KEY: MISC_FEATURE
<222> LOCATION: (5)..(5)
<223> OTHER INFORMATION: Xaa is D, E, or N
<220> FEATURE:
```

```
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (9)..(9)
<223> OTHER INFORMATION: Xaa is K, R, P, or absent
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (13)..(13)
<223> OTHER INFORMATION: Xaa is A, S, T, G, Q, N, bAla, Aib, or absent
<220> FEATURE:
<221> NAME/KEY: MISC_FEATURE
<222> LOCATION: (14)..(14)
<223> OTHER INFORMATION: Xaa is I, A, L, or V
<220> FEATURE:
<221> NAME/KEY: MISC_FEATURE
<222> LOCATION: (15)..(15)
<223> OTHER INFORMATION: Xaa is K, I, or F
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 65

Xaa Xaa Xaa Xaa Xaa Ser Glu Xaa Xaa Xaa Xaa Xaa Xaa Xaa Xaa Xaa
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is an N-terminal linker, A, G, P, or absent
<220> FEATURE:
<221> NAME/KEY: MISC_FEATURE
<222> LOCATION: (2)..(2)
<223> OTHER INFORMATION: Xaa is M, G, P, I, L, V, Nle, methionine
      sulfoxide (M(SO)), or methionine sulfone (M(SO2)), or absent
<220> FEATURE:
<221> NAME/KEY: MISC_FEATURE
<222> LOCATION: (3)..(3)
<223> OTHER INFORMATION: Xaa is H, D, E, or absent when X1 to X2 are
      absent
<220> FEATURE:
<221> NAME/KEY: MISC_FEATURE
<222> LOCATION: (4)..(4)
<223> OTHER INFORMATION: Xaa is H, D, E, or absent when X1 to X3 are
      absent
<220> FEATURE:
<221> NAME/KEY: MISC_FEATURE
<222> LOCATION: (5)..(5)
<223> OTHER INFORMATION: Xaa is D, E, or N
```

```
<220> FEATURE:
<221> NAME/KEY: MISC_FEATURE
<222> LOCATION: (6)..(7)
<223> OTHER INFORMATION: Xaa is any naturally occurring amino acid
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (13)..(13)
<223> OTHER INFORMATION: Xaa is A, S, T, G, Q, N, bAla, Aib, or absent
<220> FEATURE:
<221> NAME/KEY: MISC_FEATURE
<222> LOCATION: (14)..(14)
<223> OTHER INFORMATION: Xaa is I, A, L, or V
<220> FEATURE:
<221> NAME/KEY: MISC_FEATURE
<222> LOCATION: (15)..(15)
<223> OTHER INFORMATION: Xaa is K, I, or F
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 66

Xaa Xaa Xaa Xaa Xaa Xaa Xaa Lys Lys Arg Lys Xaa Xaa Xaa Xaa Xaa
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is an N-terminal linker, A, G, P, or absent
<220> FEATURE:
<221> NAME/KEY: MISC_FEATURE
<222> LOCATION: (2)..(2)
<223> OTHER INFORMATION: Xaa is M, G, P, I, L, V, Nle, methionine
      sulfoxide (M(SO)), or methionine sulfone (M(SO2)), or absent
<220> FEATURE:
<221> NAME/KEY: MISC_FEATURE
<222> LOCATION: (4)..(4)
<223> OTHER INFORMATION: Xaa is H, D, E, or absent when X1 to X3 are
      absent
<220> FEATURE:
<221> NAME/KEY: MISC_FEATURE
<222> LOCATION: (5)..(5)
<223> OTHER INFORMATION: Xaa is D, E, or N
<220> FEATURE:
<221> NAME/KEY: MISC_FEATURE
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
```

```
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 67

Xaa Xaa Asp Xaa Xaa Xaa Xaa Xaa Lys Xaa Xaa Xaa Xaa Ala Ile Lys Xaa
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is an N-terminal linker, A, G, P, or absent
<220> FEATURE:
<221> NAME/KEY: MISC_FEATURE
<222> LOCATION: (3)..(3)
<223> OTHER INFORMATION: Xaa is H, D, E, or absent when X1 to X2 are
      absent
<220> FEATURE:
<221> NAME/KEY: MISC_FEATURE
<222> LOCATION: (4)..(4)
<223> OTHER INFORMATION: Xaa is H, D, E, or absent when X1 to X3 are
      absent
<220> FEATURE:
<221> NAME/KEY: MISC_FEATURE
<222> LOCATION: (5)..(5)
<223> OTHER INFORMATION: Xaa is D, E, or N
<220> FEATURE:
<221> NAME/KEY: MISC_FEATURE
<222> LOCATION: (8)..(8)
<223> OTHER INFORMATION: Xaa is any naturally occurring amino acid or
      D-amino acid thereof, Aib, hydroxyproline (Hyp), P, a proline
      homolog, G, or rigidifier/helix breaker moiety
<220> FEATURE:
<221> NAME/KEY: MISC_FEATURE
<222> LOCATION: (10)..(10)
<223> OTHER INFORMATION: Xaa is any naturally occurring amino acid or
      citrulline
<220> FEATURE:
<221> NAME/KEY: MISC_FEATURE
<222> LOCATION: (11)..(11)
<223> OTHER INFORMATION: Xaa is K or any amino acid that makes the
      peptide bond between X10 and X11 uncleavable, or any amino acid
      that reduces positive charge
<220> FEATURE:
<221> NAME/KEY: MISC_FEATURE
<222> LOCATION: (12)..(12)
<223> OTHER INFORMATION: Xaa is any naturally occurring amino acid or
      bAla
<220> FEATURE:
<221> NAME/KEY: MISC_FEATURE
<222> LOCATION: (13)..(13)
<223> OTHER INFORMATION: Xaa is A, S, T, G, Q, N, bAla, Aib, or absent
<220> FEATURE:
<221> NAME/KEY: MISC_FEATURE
<222> LOCATION: (16)..(16)
<223> OTHER INFORMATION: Xaa is a hydrophobic amino acid, a D-amino acid
      thereof, or any amino acid that makes the peptide bond between X15
      and X16 uncleavable by a protease, or absent

<400> SEQUENCE: 68

Xaa Leu Xaa Xaa Xaa Ser Glu Xaa Lys Xaa Xaa Xaa Xaa Xaa Ile Lys Xaa
1               5                   10                  15
```

<210> SEQ ID NO 69
<211> LENGTH: 397
<212> TYPE: PRT
<213> ORGANISM: Homo sapiens

<400> SEQUENCE: 69

Met Arg Ser Pro Ser Ala Ala Trp Leu Leu Gly Ala Ala Ile Leu Leu
1               5                   10                  15

Ala Ala Ser Leu Ser Cys Ser Gly Thr Ile Gln Gly Thr Asn Arg Ser
            20                  25                  30

Ser Lys Gly Arg Ser Leu Ile Gly Lys Val Asp Gly Thr Ser His Val
        35                  40                  45

Thr Gly Lys Gly Val Thr Val Glu Thr Val Phe Ser Val Asp Glu Phe
    50                  55                  60

Ser Ala Ser Val Leu Thr Gly Lys Leu Thr Thr Val Phe Leu Pro Ile
65                  70                  75                  80

Val Tyr Thr Ile Val Phe Val Val Gly Leu Pro Ser Asn Gly Met Ala
                85                  90                  95

Leu Trp Val Phe Leu Phe Arg Thr Lys Lys Lys His Pro Ala Val Ile
            100                 105                 110

Tyr Met Ala Asn Leu Ala Leu Ala Asp Leu Leu Ser Val Ile Trp Phe
        115                 120                 125

Pro Leu Lys Ile Ala Tyr His Ile His Gly Asn Asn Trp Ile Tyr Gly
    130                 135                 140

Glu Ala Leu Cys Asn Val Leu Ile Gly Phe Phe Tyr Gly Asn Met Tyr
145                 150                 155                 160

Cys Ser Ile Leu Phe Met Thr Cys Leu Ser Val Gln Arg Tyr Trp Val
                165                 170                 175

Ile Val Asn Pro Met Gly His Ser Arg Lys Lys Ala Asn Ile Ala Ile
            180                 185                 190

Gly Ile Ser Leu Ala Ile Trp Leu Leu Ile Leu Val Thr Ile Pro
        195                 200                 205

Leu Tyr Val Val Lys Gln Thr Ile Phe Ile Pro Ala Leu Asn Ile Thr
    210                 215                 220

Thr Cys His Asp Val Leu Pro Glu Gln Leu Leu Val Gly Asp Met Phe
225                 230                 235                 240

Asn Tyr Phe Leu Ser Leu Ala Ile Gly Val Phe Leu Phe Pro Ala Phe
                245                 250                 255

Leu Thr Ala Ser Ala Tyr Val Leu Met Ile Arg Met Leu Arg Ser Ser
            260                 265                 270

Ala Met Asp Glu Asn Ser Glu Lys Lys Arg Lys Arg Ala Ile Lys Leu
        275                 280                 285

Ile Val Thr Val Leu Ala Met Tyr Leu Ile Cys Phe Thr Pro Ser Asn
    290                 295                 300

Leu Leu Leu Val Val His Tyr Phe Leu Ile Lys Ser Gln Gly Gln Ser
305                 310                 315                 320

His Val Tyr Ala Leu Tyr Ile Val Ala Leu Cys Leu Ser Thr Leu Asn
                325                 330                 335

Ser Cys Ile Asp Pro Phe Val Tyr Tyr Phe Val Ser His Asp Phe Arg
            340                 345                 350

Asp His Ala Lys Asn Ala Leu Leu Cys Arg Ser Val Arg Thr Val Lys
        355                 360                 365

Gln Met Gln Val Ser Leu Thr Ser Lys Lys His Ser Arg Lys Ser Ser

```
              370                 375                 380
Ser Tyr Ser Ser Ser Thr Thr Val Lys Thr Ser Tyr
385                 390                 395

<210> SEQ ID NO 70
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 70

Arg Ser Ser Ala Met Asp Glu Asn Ser Glu Lys Lys Arg Lys Ser Ala
1               5                   10                  15

Ile Lys

<210> SEQ ID NO 71
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 71

Thr Phe Leu Leu Arg Asn
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 72

Pro Arg Ser Phe Leu Leu Arg Asn
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 73

Ser Leu Ile Gly Arg Leu
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 74

Ala Tyr Pro Gly Lys Phe
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic Polypeptide
```

```
<400> SEQUENCE: 75

Thr Phe Arg Gly Ala Pro
1               5

<210> SEQ ID NO 76
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 76

Ala Ile His His Asp
1               5

<210> SEQ ID NO 77
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 77

Ala Ile Asp Glu Asn
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 78

Gly Leu His His Asp
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 79

Gly Leu Asp Glu Asn
1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 80

Ser Phe Leu Leu Arg Asn
1               5
```